US006136581A

United States Patent [19]
Joho et al.

[11] Patent Number: 6,136,581
[45] Date of Patent: Oct. 24, 2000

[54] KINASE GENES AND USES

[75] Inventors: Keith E. Joho, San Jose; Gregory D. Plowman, San Carlos, both of Calif.

[73] Assignee: Sugen, Inc., So. San Francisco, Calif.

[21] Appl. No.: 08/976,255

[22] Filed: Nov. 21, 1997

Related U.S. Application Data

[60] Provisional application No. 60/031,675, Nov. 22, 1996.

[51] Int. Cl.$^7$ .............................. C12N 9/12; C12N 15/00; C12Q 1/68; C07H 21/02
[52] U.S. Cl. ...................... 435/194; 435/320.1; 435/325; 435/252.3; 435/6; 536/23.2; 536/23.1
[58] Field of Search ........................... 435/6, 194, 320.1, 435/325, 252.3; 536/23.1, 23.2

[56] References Cited

U.S. PATENT DOCUMENTS 4,945,050  7/1990  Sanford et al. ...................... 435/172.1

FOREIGN PATENT DOCUMENTS

| 4239817 A1 | 11/1992 | Germany . |
| 93/09236 | 5/1993 | WIPO . |
| 95/25795 | 9/1995 | WIPO . |
| 96/01837 | 1/1996 | WIPO . |

OTHER PUBLICATIONS

Aaronson, "Growth Factors and Cancer," *Science* 254:1146–1153 (1991).
Adams M D et al: "Initial Assessment of Human Gene Diversity and Expression Patterns Based Upon 83 Million Nucleotides of cDNA Sequence," *Nature*, London, GB, 377:3–7 Sep. 28, 1995).
Adams, et al., EMBL Sequence Database, Heidelberg DE, XP002062967, accession nr.: AA322346, Apr. 1997.
Atshul et al., "Basic Local Alignment Search Tool," *J. Mol. Biol.* 215:403–410 (1990).
Anostario, M. Jr. et al., "Immunochemical Detection of Adenine Nucleotide–Binding Proteins with Antibodies to 5'–p–Fluorosulfonylbenzoyladenosine," *Anal. Biochem.* 190, 60–65, 1990.
Ausubel et al., *Current Protocols in Molecular Biology (Index)*, John Wiley and Sons, (1994).
Bayer et al., "The Avidin—Biotin Complex in Affinity Cytochemistry," *Meth. Enzym.* 62:308 (1979).
Benoist and Chambon, "In Vivo Sequence Requirements of the SV40 Early Promoter Region," *Nature* 290:304–310 (1981).
Bishop, "Molecular Themes in Oncogenesis," *Cell* 64:235–248 (1991).
Bollon, et al., "DNA Transformation Efficiency on Various Bacterial and Yeast Host–Vector Systems," *J. Clin. Hematol. Oncol.* 10:39–48 (1980).
Botstein, et al., "Making Mutations In Vitro and Putting Them Back Into Yeast," *From Gene to Protein: Translation Into Biochemistry*, Miami Wntr. Symp. 19:265–274 (1982).
Brinster et al., "Factors Affecting the Efficiency of Introducing Foreign DNA into Mice by Microinjecting Eggs," *Proc. Natl. Acad. Sci. USA* 82:4438–4442 (1985).

Broach, "The Yeast Plasmid 2u Circle," *Cell* 28:203–204 (1982).
Broach, In: *The Molecular Biology of the Yeast Saccharomyces: Life Cycle and Inheritance*, Cold Spring Harbor Laboratory, Cold Spring Harbor, NY, p. 445–470 (1981).
Bullock et al., *Techniques in Immunocytochemistry*, Academic Press, Orlando, FL vol. 1 (1982), vol. 2 (1983), vol. 3 (1985).
Campbell, "Monoclonal Antibody Technology: Laboratory Techniques in Biochemistry and Molecular Biology", Elsevier Science Publishers, Amsterdam, The Netherlands (1984).
Capecchi, "Altering the Genome by Homologous Recombination," *Science* 244:1288–1292 (1989).
Capecchi, MR, "High Efficiency Transformation by Direct Microinjection of DNA into Cultured Mammalian Cells," *Cell* 22:479–88 (1980).
Carraway and Cantley, "A Neu Acquaintance for ErbB3 and ErbB4: A Role for Receptor Heterodimerization in Growth Signaling," *Cell* 78:5–8 (1994).
Cenatiempo, "Prokaryotic Gene Expression In Vitro: Transcription–Translation Coupled Systems," *Biochimie* 68:505–516 (1986).
Chard, "An Introduction to Radioimmunoassay and Related Techniques" Elsevier Science Pulishers, Amsterdam, The Netherlands (1986).
Chater et al, In: Sixth International Symposium on Actinomycetales Biology, Akademiai Kaido, Budapest, Hungary (1986), pp. 45–54.
Chen and Okayama, "High–Efficiency Transformation of Mammalian Cells by Plasmid DNA," *Molecular and Cellular Biology* 7(8):2745–2752 (1987).
Chomczynski and Sacchi, "Single–Step Method of RNA Isolation by Acid Guanidinium Thiocyanate–Phenol–Chloroform Extraction," *Analytical Biochemistry* 162:156–159 (1987).
Chu G. et al., "Electroporation for the Efficient Transfection of Mammalian Cells with DNA," *Nucleic Acids Res.*, 15:1311–26 (1987).
Curiel et al., "Gene Transfer to Respiratory Epithelial Cells via the Receptor–mediated Endocytosis Pathway," *Am J. Respir. Cell. Mol. Biol.* 6:247–252 (1992).
Felgner and Ringold, "Cationic liposome–mediated transfection," *Nature* 337:387–388 (1989).

(List continued on next page.)

*Primary Examiner*—Rebecca E. Pronty
*Assistant Examiner*—M. Monshipouri

[57] ABSTRACT

The specification describes isolated, purified, or enriched nucleic acid molecules which correspond to particular genes encoding kinases, and to fragments of such genes, as well as the polypeptides encoded by such nucleic acids and antibodies specific for those polypeptides. Also disclosed are methods using such nucleic acid molecules, polypeptides, or antibodies for isolating the full coding sequences for those kinases, for determining the expression patterns and levels for those genes, for screening for agents which modulate the activity of one of the kinases, and for diagnosing or treating a disease associated with one of the kinases.

19 Claims, 20 Drawing Sheets

OTHER PUBLICATIONS

Felgner et al., "Lipofection: A Highly Efficient, Lipid–mediated DNA–transfection Procedure," *Proc. Natl. Acad. Sci. USA* 84:7413–7417 (1987).

Gaozza E et al.: "AATYK: A novel tyrosine kinase induced during growth arrest and aptosis of meyloid cells," EMBL Sequence Database, Oct. 3, 1997, Heidelberg DE.

Gerard, GF et al., (1989), *FOCUS* 11, 66–69.

Gilman et al., "Isolation of Sigma–28–Specific Promoters from *Bacillus Subtilis* DNA," *Gene* 32:11–20 (1984).

Glick, "Factors Affecting the Expression of Foreign Proteins in *Escherichia Coli,*" *J. Ind. Microbiol.* 1:277–282 (1987).

Goding, J., "Conjugation of Antibodies with Fluorochromes: Modifications to the Standard Methods," *J. Immunol. Meth.* 13:215–226 (1976).

Gold, et al, "Translational Initiation in Prokaryotes," *Ann. Rev. Microbiol.* 35:365–404 (1981).

Gottesman, "Bacterial Regulation: Global Regulatory Networks," *Ann. Rev. Genet.* 18:415–441 (1984).

Gryczan, In: *The Molecular Biology of the Bacilli,* Academic Press, Inc. NY (1982).

Hamer, et al., "Regulation In Vivo of a Cloned Mammalian Gene: Cadmium Induces the Transcription of a Mouse Metallothionein Gene in SV 40 Vectors," *J. Mol. Appl. Gen.* 1:273–288 (1982).

Hammer et al., "Spontaneous Inflammatory Disease in Transgenic Rats Expressing HLA–B27 and Human β2m: An Animal Model of HLA–B27–Associated Human Disorders," *Cell* 63:1099–1112 (1990).

Hanks and Hunter, "The Eukaryotic Protein Kinase Superfamily: Kinase (Catalytic) Domain Structure and Classification," *FASEB Journal* 9:576–595 (May 1995).

Hardie, "Roles of Protein Kinases and Phosphatases in Signal Transduction," *Symp. Soc. Exp. Bio.* 44:241–255 (1990).

Hida, et al., "Ectopic Expression of c–kit In Small–Cell Lung Cancer," *Int. J. Can.* (*supp 8*):108–109 (1994).

Hillier L et al.: "Human cDNA clone 265618," EMBL Sequence Database, Dec. 30, 1995, Heidelberg DE.

Hillier L et al.: "Human cDNA clone 270151," EMBL Sequence Database, Jan. 27, 1996, Heidelberg DE.

Hillier L et al.: "Human cDNA clone 308512," EMBL Sequence Database, Apr. 19, 1996, Heidelberg DE.

Hillier L et al.: "Human cDNA clone 32217," EMBL Sequence Database, Apr. 22, 1995, Heidelberg DE.

Houdebine and Chourrout, "Transgenesis in Fish," *Experientia* 47:891–897 (1991).

Hurby et al., "Application of Synthetic Peptides: Antisense Peptides", In *Synthetic Peptides, A User's Guide,* W.H. Freeman, NY, pp. 289–307 (1992).

Innis, et al., "A Guide to Methods and Applications", Academic Press, 1990.

Izaki, *Jpn. J. Bacteriol.* 33:729–742 (1978).

Jakoby et al., *Meth. Enzym.* 34:Index (1974).

Jasny, "Insect Viruses Invade Biotechnology," *Science* 238:1653 (1987).

John, et al., "Plasmids as Epidemiologic Markers in Nosocomial Gram–Negative Bacilli: Experience at a University and Review of Literature," *Rev. Infect. Dis.* 8:693–704 (1986).

Johnston and Hopper, "Isolation of the Yeast Regulatory Gene GAL4 and Analysis of its Dosage Effects on the Galactose/Melibiose Regulon," *Proc. Natl. Acad. Sci. USA* 79:6971–6975 (1982).

Joyner et al., "Production of a mutation in mouse En–2 gene by homologous recombination in embryonic stem cells," *Nature* 338:153–156 (1989).

Kaplan et al., "The trk Proto–Oncogene Product: A Signal Transducing Receptor for Nerve Growth Factor," *Science* 252:554–558 (1991).

Kasprzak et al., "Location of a Contact Site between Actin and Myosin in the Three–Dimensional Structure of the Acto–S1 Complex" *Biochemistry* 28:9230–8 (1989).

Kendall, et al, "Plasmid Transfer in *Streptomyces Lividans:* Identification of a kil–kor System Associated with the Transfer Region of pIJ101," *J. Bacteriol.* 169:4177–4183 (1987).

Klein, et al , "The trkB Tyrosine Protein Kinase Is a Receptor for Brain–Derived Neutrophic Factor and Neurotrophin–3," *Cell* 66:395–403 (1991).

Klein, et al., "Expression of the Tyrosine Kinase Receptor Gene trkB is Confined to the Murine Embryonic and Adult Nervous System," *Development* 109:845–850 (1990).

Klein, M. Kanehisa and C. DeLisi, "The Detection and Classification of Membrane–Spanning Proteins," *Biochim. Biophys. Acta,* 815, 468–476, 1985.

Krystal, et al, "Autocrine Growth," *Can. Res.* 56(2):370–376 (1996).

Lee n h et al: "Comparative Expressed–Sequence Tag Analysis of Differential Gene Expression Profiles in PC–12 Cells Before and After Nerve Growth Factor Treatment," Proceedings of the National Academy of Sciences of USA., 92:8303–8307 (Aug. 1995).

Lee, et al., EMBL Sequence Database, Heidelberg DE, XP002062968, accession No. AA351400, Sep. 1995.

Lee, et al., EMBL Sequence Database, Heidelberg DE, XP002062969, accession No. H31142, Sep. 1997.

Lutz et al., "The Distribution of Two hnRNA–Associated Proteins Defined by a Monoclonal Antibody Is Altered in Heat–Shocked HeLa Cells," *Experimental Cell Research* 175:109–124 (1988).

Maniatis, In: Cell Biology: A Comprehensive Treatise, vol. 3, *Gene Sequence Expression,* Academic Press, NY, pp. 563–608 (1980).

McGeoch, "On the Predictive Recognition of Signal Peptide Sequences," *Virus Research* 3:271 (1985).

McKnight, "Functional Relationships between Transcriptional Control Signals of the Thymidine Kinase Gene of Herpes Simplex Virus," *Cell* 31:355–365 (1982).

Miller et al., *Genetic Engineering,* Setlow, J. K., et al., eds., Plenum, vol. 8, pp. 277–297 (1986).

Miller, "Human gene therapy comes of age," *Nature* 357:455–460 (1992).

Moody, "Peptides and Growth Factors in Non–Small Cell Lung Cancer," *Peptides* 17(3):545–555 (1996).

Mulligan, "The Basic Science of Gene Therapy," *Science* 260:926–932 (1993).

Oelmann, et al, "Nerve Growth Factor Stimulates Clonal Growth of Human Lung Cancer Cell Lines and a Human Glioblastoma Cell Line Expressine High–Affinity Nerve Growth Factor Binding Sites Involving Tyrosine Kinase Signaling," *Can. Res.* 55(10):2212–2219 (1995).

Okayama, "A cDNA Cloning Vector That Permits Expression of cDNA Inserts in Mammalian Cells," *Molec. Cell. Bio.* 3:280–289 (1980).

Posada and Cooper, "Molecular Signal Integration. Interplay Between Serine, Threonine and Tyrosine Phosphorylation," *Molecular Biology of the Cell* 3:583–592 (1992).

Pursel et al., "Genetic Engineering of Livestock," *Science* 244:1281–1288 (1989).

Robertson, ed., *Teratocarcinomas and Embryonic Stem Cells, A Practical Approach,* IRL Press (1987).

Rubin, "*Drosophila Melanogaster* as an Experimental Organism," *Science* 240:1453–1459 (1988).

Sambrook, J. et al, *Molecular Cloning: A Laboratory Manual,* Cold Spring Harbor Laboratory (1989).

Simons et al., "Gene Transfer into Sheep," *Bio/Technology* 6:179–183 (1988).

Slamon et al., "Human Breast Cancer: Correlation of Relapse and Survival with Amplification of the HEr–2/neu Oncogene," *Science* 235:177–185 (1987).

St. Groth et al., "Production of Monoclonal Antibodies: Strategy and Tactics," *J. Immunol. Methods,* 35:1–21 (1980).

Stemberger et al., "The Unlabeled Antibody Enzyme Method of Immunohistochemistry," *J. Histochem. Cytochem.* 18:315–332 (1970).

Tijssen, "Practice and Theory of Enzyme Immunoassays: Laboratory Techniques in Biochemistry and Molecular Biology", Elsevier Science Publishers, Amsterdam, The Netherlands (1985).

Tsai, et al, "Enhancement of Chemosensitivity by Tyrphostin AG825 in High–p185neu Expressing Non–Small Cell Lung Cancer Cells," *Can. Res.* 56 (5): 1068–1074 (1996).

Ulmanen et al., "Transcription and Translation of Foreign Genes in *Bacillus Subtilis* by the Aid of a Secretion Vector," *J. Bacteriol.* 162:176–182 (1985).

von Heijne, "A New Method for Predicting Signal Sequence Cleavage Sites," *Nucleic Acids Research* 14(11):4683–4691 (1986).

Ward et al., "Construction and Characterisation of a Series of Multi–copy Promoter–probe Plasmid Vectors for Streptomyces Using the Aminoglycoside Phosphotransferase Gene From Tn5 as Indicator," *Mol. Gen. Genet.* 203:468–478 (1986).

Weir et al., *Handbook of Experimental Immunology,* 4$^{th}$ Ed., Blackwell Scientific Publications, Oxford, England, Chapter 10 (1986).

Yan, et al., "Chimeric NGF–EGF Receptors Define Domains Responsible for Neuronal Differentiation," *Science* 252:561–563 (1991).

Yang et al., "In Vivo and In Vitro Gene Transfer into Mammalian Somatic Cells by Particle Bombardment," *Proc. Natl. Acad. Sci. USA* 87:9568–9572 (1990).

Hillier et al., EST Dtabase, Accession No. R17441.

Adams et al., EST Database, Accession No. T31187.

FIG. 1A

HUMAN LMR1, LMR2, AND LMR3 ALIGNMENT

FIG. 1B-1

HUMAN LMR1, LMR2, AND LMR3 ALIGNMENT

FIG. 1B-2

HUMAN LMR1, LMR2, AND LMR3 ALIGNMENT

```
LMR1_h  SGPGEVLPPLLQLEGSS-PEPSTCPSGLVPEPPEPQGPAKVRPGPSPSCSQFFLLT--PV      1116
LMR2_h  CLSALHNSSDLELLRATPEPAQTGVPQQVHPTEDEASSPWSVLNAELSSGDDFEETQDDRPQ    1223

LMR1_h  PLRSEGNSSE----FQGPP--GLLSGPAPQKRMGGPGTPRAPLI-RLALPGLPAALEGRPE     1169
LMR2_h  TLASTGTNTNELLAYTNSALDKSLSSHSEGPKLKEPDIEGKYLGKLGVSGM-LDLSEDGM      1282

LMR1_h  EEEEDSEDSDESDEELRCYSVQEPSEDSEEEAPAVPVVVAESQSARNLRSLLK-MPSLLS      1228
LMR2_h  DADEEDENSDDSDEDLRAFNLHSLSSESEDETEHPVPIILSNEDGRHLRSLLKPTAANAP     1342
                                    ★

LMR1_h  ETFCEDLERKKKAVSFFDDVTVYLFDQESPTRELGEPFPGAKESPPTFLRGSPGSPSAPN     1288
LMR2_h  DPLPEDWKKEKKAVTFFDDVTVYLFDQETPTKELGP--CGGEACGPD-LSGPAPASGSPY    1399

LMR1_h  RPQQADGSPNGSTAEEGGGFAWDDDFP-------LMTAKAAFAMA--LDPAAPAPA         1335
LMR2_h  LSRCINS--ESSTDEEGGGFEWDDDFSPDPFMSKTTSNLLSSKPSLQTSKYFSPPPARS     1457

LMR1_h  APT--PTPAPFSRFTVSPAPTSRFSITHVSDSDAESKRGPEAGAGGESKEA              1384
LMR2_h  TEQSWPHSAPYSRFSISPANIASFSLTHLTDSDIEQGGSSEDGE----KD               1504
```

| * | Oligo | bp | 5'/3' | Degenerate nucleotide sequence | Targetted aa sequence motif |
|---|---|---|---|---|---|
| | TRKa | 25 | 5 | GAAAGCTTGGNGCNTTYGGNAARGT | GAFGKV |
| | TRKb | 24 | 3 | GCCAAGCTTYTCNGGNGGCATCCA | WMPPE |
| 1 | TEK1 | 31 | 5 | CTGAATTCGGNGARGGNAAYTTYGGNCARGT | GEGNFGQV |
| 2 | ROS1 | 23 | 5 | GCNTTYGGNGARGTNTAYGARGG | AFGEVYEG |
| 3 | HRDRTK | 36 | 5 | CCGGGATCCACAAGCTTCCCTNCAYMRDGAYNTNGC | HRD(LIV)A |
| 4 | IROSD3 | 26 | 5 | GGCCACGGCTGGTTYGGNAARGTNTT | GHGWFGKV |
| 5 | IROSD1 | 24 | 3 | ATGCARTTYCTGGARGARGCNCAY | WYAPE |
| 6 | IROSD2 | 24 | 3 | ATGTAGRTRCARNAYNCCRCANGC | WTAPE |
| 7 | IROSD4 | 27 | 3 | GCTCCGTAGRTANCCYTTNARRTCNCC | ACG(MV)L(YH)LH |
| 8 | IROSD5 | 27 | 3 | GATTGTNACNCCNARNSWCCANACRTT | NVWXXGVTI |
| 9 | IROSD6 | 26 | 3 | TTCAGRTCNCCNARNGGRCARAAYTC | EFCPXGDL |

Fig. 2

Human LMR1, LMR2, and LMR3 Northern Blot Expression

| Cell type | Origin | LMR1_h | LMR2_h | LMR3_h |
|---|---|---|---|---|
| Brain | Normal tissue | 4 | 3 | 4 |
| Cortex | Normal tissue | 2 | 0 | 2 |
| Cerebellum | Normal tissue | 3 | 0 | 2 |
| Thymus | Normal tissue | 0 | 0 | 0 |
| Salivary Gland | Normal tissue | 0 | 0 | 0 |
| Lung | Normal tissue | 0 | 0 | 0 |
| Heart | Normal tissue | 0 | 0 | 0 |
| Liver | Normal tissue | 0 | 0 | 0 |
| Pancreas | Normal tissue | 0 | 0 | 0 |
| Kidney | Normal tissue | 0 | 0 | 0 |
| Stomach | Normal tissue | 0 | 0 | 0 |
| Duodenum | Normal tissue | 0 | 0 | 0 |
| Uterus | Normal tissue | 0 | 0 | 0 |
| Prostate | Normal tissue | 0 | 0 | 0 |
| Skeletal Muscle | Normal tissue | 0 | 0 | 0 |
| Placenta | Normal tissue | 0 | 0 | 0 |
| Fetal Brain | Normal tissue | 0 | 0 | 2 |
| Mammary Gland | Normal tissue | 0 | 0 | 0 |
| Testis | Normal tissue | 0 | 0 | 0 |
| Bladder | Normal tissue | 0 | 0 | 0 |
| Lymph Node | Normal tissue | 0 | 0 | 0 |
| Colon | Normal tissue | 0 | 0 | 0 |
| Adipose Tissue | Normal tissue | 0 | 0 | 0 |
| Spleen | Normal tissue | 0 | 0 | 0 |
| Fetal Liver | Normal tissue | 0 | 0 | 0 |
| | | | | |
| HOP-92 | Lung tumor | 1 | 3 | 0 |
| EKVX | Lung tumor | 1 | 2 | 0 |
| NCI-H23 | Lung tumor | 1 | 3 | 0 |
| NCI-H226 | Lung tumor | 0 | 2 | 0 |
| NCI-H322M | Lung tumor | 0 | 4 | 0 |
| NCI-H460 | Lung tumor | 0 | 2 | 0 |
| NCI-H522 | Lung tumor | 0 | 1 | 0 |
| A549 | Lung tumor | 0 | 2 | 0 |
| HOP-62 | Lung tumor | 0 | 1 | 0 |
| OVCAR-3 | Ovarian tumor | 0 | 1 | 0 |
| OVCAR-4 | Ovarian tumor | 0 | 1 | 0 |
| OVCAR-5 | Ovarian tumor | 0 | 2 | 0 |
| OVCAR-8 | Ovarian tumor | 0 | 1 | 0 |
| IGROV1 | Ovarian tumor | 0 | 1 | 0 |
| SK-OV-3 | Ovarian tumor | 0 | 1 | 0 |
| SNB-19 | CNS tumor | 0 | 1 | 0 |
| SNB-75 | CNS tumor | 2 | 1 | 0 |
| U251 | CNS tumor | 0 | 1 | 0 |
| SF-268 | CNS tumor | 0 | 1 | 0 |

*Fig. 3A*

| Cell type | Origin | LMR1_h | LMR2_h | LMR3_h |
|---|---|---|---|---|
| SF-295 | CNS tumor | 0 | 1 | 0 |
| SF-539 | CNS tumor | 0 | 1 | 0 |
| CCRF-CEM | Leukemia | 0 | 1 | 0 |
| K-562 | Leukemia | 0 | 1 | 0 |
| MOLT-4 | Leukemia | 0 | 1 | 0 |
| HL-60 | Leukemia | 0 | 0 | 0 |
| RPMI 8226 | Leukemia | 0 | 3 | 0 |
| SR | Leukemia | 0 | 1 | 0 |
| DU-145 | Prostate tumor | 0 | 2 | 0 |
| PC-3 | Prostate tumor | 0 | 1 | 0 |
| HT-29 | Colon tumor | 0 | 0 | 0 |
| HCC-2998 | Colon tumor | 1 | 1 | 0 |
| HCT-116 | Colon tumor | 0 | 0 | 0 |
| SW620 | Colon tumor | 0 | 1 | 0 |
| Colo 205 | Colon tumor | 0 | 4 | 0 |
| HTC15 | Colon tumor | 0 | 2 | 0 |
| KM-12 | Colon tumor | 0 | 1 | 0 |
| UO-31 | Colon tumor | 0 | 1 | 0 |
| SN12C | Kidney tumor | 0 | 1 | 0 |
| A498 | Kidney tumor | 0 | 1 | 0 |
| CaKi1 | Kidney tumor | 0 | 1 | 0 |
| RXF-393 | Kidney tumor | 0 | 1 | 0 |
| ACHN | Kidney tumor | 0 | 1 | 0 |
| 786-0 | Kidney tumor | 0 | 1 | 0 |
| TK-10 | Kidney tumor | 0 | 2 | 0 |
| LOX IMVI | Melanoma | 0 | 1 | 0 |
| Malme-3M | Melanoma | 1 | 1 | 0 |
| SK-MEL-2 | Melanoma | 0 | 1 | 0 |
| SK-MEL-5 | Melanoma | 0 | 1 | 0 |
| SK-MEL-28 | Melanoma | 0 | 1 | 0 |
| UACC-62 | Melanoma | 1 | 2 | 0 |
| UACC-257 | Melanoma | 1 | 1 | 0 |
| M14 | Melanoma | 0 | 2 | 0 |
| MCF-7 | Breast tumor | 0 | 3 | 0 |
| MCF-7/ADR RES | Breast tumor | 0 | 1 | 0 |
| Hs578T | Breast tumor | 0 | 1 | 0 |
| MDA-MB-231 | Breast tumor | 0 | 1 | 0 |
| MDA-MB-435 | Breast tumor | 0 | 1 | 0 |
| MDA-N | Breast tumor | 0 | 1 | 0 |
| BT-549 | Breast tumor | 0 | 1 | 0 |
| T47D | Breast tumor | 0 | 2 | 0 |

*Fig. 3B*

| Rat Embryo (E16) *In Situ* Hybridization |||||
|---|---|---|---|---|
| Tissue Region | Sub-region | LMR1_r | LMR2_r | LMR3_r |
| embryonic brain | cortex | 1 | 4 | 3 |
| | corpus striatum | 1 | 4 | 2 |
| | roof of midbrain | 2 | 4 | 2 |
| | thalamus | 2 | 3 | 4 |
| | pons | 1 | 3 | 4 |
| | medulla oblongata | 2 | 4 | 4 |
| | vestibulochoclear (VIII) | 0 | 3 | 3 |
| | trigeminal (V) ganglion | 0 | 4 | 0 |
| dorsal root ganglion | | 4 | 4 | 4 |
| spinal cord | | 4 | 4 | 4 |
| neural layer of the retina | | 0 | 4 | 0 |
| olfactory epithelium | | 0 | 3 | 0 |
| spine (cartilage) | | 0 | 4 | 1 |
| heart | | 0 | 2 | 0 |
| lung | | 0 | 2 | 1 |
| liver | | 0 | 4 | 0 |
| pancreas | | 0 | 3 | 0 |
| stomach | | 0 | 4 | 3 |
| midgut and colon | | 0 | 4 | 3 |
| kidney | | 0 | 3 | 0 |
| pituitary | | 0 | 2 | 0 |

*Fig. 4*

| Adult Rat Brain *in situ* hybridization | | | | |
|---|---|---|---|---|
| *Tissue Region* | *Sub-region* | *LMR1_r* | *LMR2_r* | *LMR3_r* |
| Cerebellum | Purkinje layer | 2 | 4 | 2 |
| Cortex | Anterior | 1.0 | 4 | 3 |
| Cortex | Piriform | 0 | 3.5 | 1 |
| Substantia nigra | | 0 | 2 | 0 |
| Zona incerta | | 0 | 3 | 1 |
| Hippocampus | CA1 | 1 | 4 | 4 |
| | CA2 | 0 | 4 | 4 |
| | CA3 | 0 | 4 | 4 |
| | Dentate gyrus | 0 | 4 | 4 |
| | Subiculum | 0 | 4 | 0 |
| Thalamic nucleus | | 1 | 2 | 1 |
| Caudate/Putamen | | 0 | 2 | 1 |
| Inferior colliculus | | 0 | 2 | 0 |
| Subthalamus | | 0 | 3 | 1 |
| Cerebellum | Purkinje layer | 2 | 4 | 2 |
| Amygdaloid nucleus | | 2 | 2.0 | 2 |
| Supramammilary nucleus | | 0 | 0 | 2 |
| medial mammillary nucleus | | 0 | 0 | 2 |
| Brain stem | Trigeminal nucleus (V) | 1.5 | 2.5 | 0 |
| | Facial nucleus (VII) | 1.5 | 4 | 2 |
| | Nucleus K | 1.5 | 0 | |

*Fig. 5*

Nucleotide sequences of LMRs

```
>>LMR1_r (SEQ ID NO. 1)
cccgccccgggGATGCCCATCGCGCTGCTGGCCCTGGCCATGTCGTCGTCCTTCTTCAAC
CCCAGCTTTGCCTTCAGCTCCCACTTCGACCCGGACGGTGCCCCGCTCAGTGAGCTATCC
TGGTCCTCGTCCCTTGCAGTGGTTGCTGTGTCCTTCTCTGGGATCTTCACTGTCATTGTC
CTCATGCTGGCCTGCCTGTGCTGTAAGAAGGGCGGCATTGGGTTCAAGGAGTTTGAGAAT
GCTGAAGGGGAAGAGTATGTGGCCGACTTCTCGGAGCAGGGCTCCCCGGCTGCTACTGTA
CAGAACGGCCCCGATGTGTATGTCCTGCCTCTCACTGAGGTCTCCCTGCCCATGGcTAAg
CAGCCGGGTCGCTCAGTGCAACTCCTCAAGTCCACGGACCTGGGCCGCCACAGCCTCCTG
TACTTGAAGGAGATTGGCCACgGTTGGTTTGGGAAGGTGTTCTTGGGGAGGTGCACTCG
GGTGTCAGTGGCACGCAGGTGGTGGTGAAGGAGCTGAAGGCCAGCGCCAGTGTGCAGGAG
CAGATGCAGTTCCTGGAGGAGGCGCAGCCCTACAGGGCCCTGCAGCACAGCAACCTGCTT
CAGTGCCTGGCCCAGTGTGCTGAgGTGACCCCCTATTTGCTGGTTATGGAGTTCTGTCCC
CTGGGGGACCTCAAAGGTTATCTACGGAGCTGCCGGGTGACAGAGTCCATGGCGCCTGAC
CCCCTTACCTTGCAGCGCATGGCGTGCGAGGTGGCGTGTGGTGTCTTGCATCTACATCGT
CACAACTATGTGCACAGTGACCTGGCCCTGAGGAACTGCCTGCTGACGGCTGACCTGACA
GTGAAGGTTGGCGACTATGGCCTGGCCCATTGCAAATACAGGGAAGACTACCTCGTGACG
GCCGACCAGTTGTGGGTGCCGCTGCGTTGGATCGCGCCAGAGCTGGTGGATGAGGTGCAT
GGCAACCTACTGGTGGTGGACCAGACTAAGACCAGCAATGTGTGGTCCCTGGGTGTGACC
ATCTGGGAGCTTTTCGAGTTGGGCGCGCAGCCCTACCCCCAGCACTCGGACCGGCAGGTG
CTGGCTTACGCCGTCCGAGAACAGCAACTTAAGTTGCCCAAGCCCCAGCTACAGCTGACT
CTGTCTGATCGATGGTACGAGGTGATGCAGTTCTGCTGGCTTCAGCCAGAACAGAGGCCT
ACGGCTGAGGAGGTTCATCTGCTGCTGTCCTACTTGTGCGCCAAGGGCACCACGGAGCTG
GAGGAGGAGTTCGAGCGGCGCTGGCGCTCCCTGCGGCCGGGGGGCAGCGCGGGGCTGGGC
TCAGCTTCCACAGTCCCGGCAGCTGCCGCATCTGAACTCACTGCTGCTTCATCTTTCCCG
CTGCTGGAGCAGTTCACCAGTGACGGCTTCCACGTGGACAGCGACGACGTGCTGACAGTC
ACTGAGACGAGCCACGGCCTCAACTTCGAATACAAGTGGGAGGCTGGCTGTGGCGCTGAG
GCTTACCCGCCCCCAGGCGCTGCTTTCAGCCCAGGTTCCGCAGGGCGCCTGCAGGAGCTG
TGTGCACCCGACAGCTCGCCGCCGGGTGTGGTGCCGGTCCTCAGTGCCCACAGCCCCTCA
GTGGGTAGCGAGTACTTCATCCGCCTGGAGGGGGCAGTGCCGGCTGCTGGCCATGACCCA
GACTGTGCCGGCTGTGCTCCCAGCCCCCAAGCTGTGTCCGAGCAGGACAATAACTCTGAG
GAGAGCACCGCTGCATCCCTTGTCATGGAGCCGCTTcTGGGCCACGCACCACCCACTGGG
GGCCTGTGGGGCCCTGCGACCATCATTCTCGAAGGAGGCAAGAGCCACCCTGCCCCTCA
CGCTCACCCTCTCCTGGGACCCCGATGTTGCCAGCTGAAGACATAGACTGGGGTGTAGCT
ACCTTCTGCCCACCCtttttGATGACCCACTGGGCACATCTCCCTCTGGGAGTCCTGGG
GCCCAGCCATCCCCCAGTGATGAGGAGCTGGAGGAGGGAAAGACTGGGAGGGCTGCTCAG
TGTGGACACTGGAGCTCTAACATGTCTGCCAACAATAACAGTGGCAGTCGAGACCCAGAA
TCCTGGGATCCTGGCTATGTGAGCAGCTTCACAGACAGCTACAGGGACGACTGCTCCAGC
TTAGAGCAGACCCCTCGGGCCTCCCTGAGCTGGGCCATCCCCTGTCCCAGGAGGATTCC
AGAGATTTTTTACCTGGGCTAGTAGCAGCTTCCCCTGGCCAGGAGTCAAGCCGTTGcTTC
AACCTGCTCCCTcTGTGTCCTGCCAAAGGCCTGGCACCTGcTGCTTGCCTCGTCCCACCC
CCCTGGACAGAGGCAGCTGTAgGTGGGGCTGAGAACCCCATTGTCGAACCCAAACTTGCC
CAGGAGGCTGAGGGCTCTGCTGAACCCCAGCTACCCCTTCCTTCTGTCCCCTCCCCATCC
CACGAAGGAGCCTCGCTTCCTCGGAGGAGGCAAGCGCTCCTGACATCCAGCCTGCCTCT
CCTACACCCGCTGCTGGCAGCTGGGTGACCGTCCTGAGGTCGAcgcggccgc
>
```

*Fig. 6A*

Nucleotide Sequences of LMRs

>>LMR1_h (SEQ ID NO. 2)
gaattcCCCAGCTTCGCCTTCAGCTCGCACTTCGACCCCGACGGCGCCCCGCTCAGCGAGC
TGTCCTGGGCATCCTCCCTCGCCGTGGTGGCTGTGTCTTTCTCCGGGCTCTTCGCCGTCAT
CGTCCTCATGCTGGCCTGCCTGTGCTGTAAGAAGGGCGGTATCGGGTTCAAGGAGTTTGAG
AATGCGGAGGGGACGAGTACGCAGCCGACCTGGCGCAGGGCTCCCCGGCCACGGCAGCAC
AGAACGGGCCCGACGTGTACGTCCTGCCACTCACGGAGGTCTCCTTGCCCATGGCCAAGCA
GCCTGGGCGCTCAGTGCAGCTCCTCAAGTCCACAGACGTGGGCCGGCACAGCCTCCTGTAC
CTGAAGGAAATCGGCCGTGGCTGGTTCGGGAAGGGAAATCGGCCGTGGCTGGTTCGGGAAG
GTGTTCCTGGGGGAGGTGAACTCTGGCATCAGCAGTGCCCAGGTGGTGGTGAAGGAGCTGC
AGGCTAGTGCCAGCGTGCAGGAGCAGATGCAGTTCCTGGAGGAGGTGCAGCCCTACAGGGC
CCTGAAGCACAGCAACCTGCTCCAGTGCCTGGCCCAGTGCGCCGAGGTGACGCCCTACCTG
CTGGTGATGGAGTTCTGCCCACTGGGGGACCTCAAGGGCTACCTGCGGAGCTGCCGGGTGG
CGGAGTCCATGGCTCCCGACCCCGGACCCTGCAGCGCATGGCCTGTGAGGTGGCCTGTGG
CGTCCTGCACCTTCATCGCAACAATTTCGTGCACAGCGACCTGGCCCTGCGGAACTGCCTG
CTCACGGCTGACCTGACGGTGAAGATTGGTGACTATGGCCTGGCTCACTGCAAGTACAGAG
AGGACTACTTCGTGACTGCCGACCAGCTGTGGGTGCCTCTGCGCTGGATCGCGCCAGAGCT
GGTGGACGAGGTGCATAGCAACCTGCTCGTCGTGGACCAGACCAAGAGCGGGAATGTGTGG
TCCCTGGGCGTGACCATCTGGGAGCTCTTTGAGCTGGGCACGCAGCCCTATCCCCAGCACT
CGGACCAGCAGGTGCTGGCGTACACGGTCCGGGAGCAGCAGCTCAAGCTGCCCAAGCCCCA
GCTGCAGCTGACCCTGTCGGACCGCTGGTACGAGGTGATGCAGTTCTGCTGGCTGCAGCCC
GAGCAGCGGCCCACAGCCGAGGAGGTGCACCTGCTGCTGTCCTACCTGTGTGCCAAGGGCG
CCACCGAAGCAGAGGAGGAGTTTGAACGGCGCTGGCGCTCTCTGCGGCCCGGCGGGGGCGG
CGTGGGGCCCGGGCCCGGTGCGGCGGGGCCCATGCTGGGCGGCGTGGTGGAGCTCGCCGCT
GCCTCGTCCTTCCCGCTGCTGGAGCAGTTCGCGGGCGACGGCTTCCACGCGGACGGCGACG
ACGTGCTGACGGTGACCGAGACCAGCCGAGGCCTCAATTTTGAGTACAAGTGGGAGGCGGG
CCGCGGCGCGGAGGCCTTCCCGGCCACGCTGAGCCCTGGCCGCACCGCACGCCTGCAGGAG
CTGTGCGCCCCCGACGGCGCGCCCCGGGCGTGGTTCCGGTGCTCAGCGCGCACAGCCCGT
CGCTGGGCAGCGAGTACTTCATCCGCCTAGAGGAGGCCGCACCCGCCGCCGGCCACGACCC
TGACTGCGCCGGCTGCGCCCCCAGTCCACCTGCCACCGCGGACCAGGACGACGACTCTGAC
GGCAGCACCGCCGCCTCGCTGGCCATGGAGCCGCTGCTGGGCCACGGGCCACCCGTCGACG
TCCCCTGGGGCCGCGGCGACCACTACCCTCGCAGAAGCTTGGCGCGGGACCCGCTCTGCCC
CTCACGCTCTCCCTCGCCCTCGGCGGGGCCCCTGAGTCTGGCGGAGGGAGGAGCGGAGGAT
GCAGACTGGGGCGTGGCCGCCTTCTGTCCTGCCTTCTTCGAGGACCCACTGGGCACGTCCC
CTTTGGGGAGCTCAGGGGCGCCCCGCTGCCGCTGACTGGCGAGGATGAGCTAGAGGAGGT
GGGAGCGCGGAGGGCCGCCCAGCGCGGGCACTGGCGCTCCAACGTGTCAGCCAACAACAAC
AGCGGCAGCCGCTGTCCAGAGTCCTGGGACCCCGTCTCTGCGGGCTGCCACGCTGAGGGCT
GCCCCAGTCCAAAGCAGACCCCACGGGCCTCCCCGAGCCGGGGTACCCTGGAGAGCCTCT
GCTTGGGCTCCAGGCAGCCTCTGCCCAGGAGCCAGGCTGCTGCCCCGGCCTCCCTCATCTA
TGCTCTGCCCAGGGCCTGGCACCTGCTCCCTGCCTGGTTACACCCTCCTGGACAGAGACAG
CCAGTAGTGGGGGTGACCACCCGCAGGCAGAGCCCAAGCTTGCCACGGAGGCTGAGGGCAC
TACCGGACCCCGCCTGCCCCTTCCTTCCGTCCCCTCCCCATCCCAGGAGGGAGCCCCACT
TCCCTCGGAGGAGGCCAGTGCCCCGACGCCCTGATGCCCTGCCTGACTCTCCCACGCC
TGCTACTGGTGGCGAGGTGTCTGCCATCAAGCTGGCTTCTGCCCTGAATGGCAGCAGCAG
CTCTCCCGAGGTGGAGGCACCCAGCAGTGAGGATGAGGACACGGCCGAGGCCACCTCAGG
CATCTTCACCGACACGTCCAGCGACGGCCTGCAGGCCAGGAGGCCGGATGTGGTGCCAGC
CTTCCGCTCTCTGCAGAAGCAGGTGGGGACCCCCGACTCCCTGGACTCCCTGGACATCCC

*Fig. 6B*

Nucleotide Sequences of LMRs

```
GTCCTCAGCCAGTGATGGTGGCTATGAGGTCTTCAGCCCGTCGGCCACTGGCCCCTCTGG
AGGGCAGCCGCGAGCGCTGGACAGTGGCTATGACACCGAGAACTATGAGTCCCCTGAGTT
TGTGCTCAAGGAGGCGCAGGAAGGGTGTGAGCCCCAGGCCTTTGCGGAGCTGGCCTCAGA
GGGTGAGGGCCCCGGGCCCGAGACACGGCTCTCCACCTCCCTCAGTGGCCTCAACGAGAA
GAATCCCTACCGAGACTCTGCCTACTTCTCAGACCTCGAGGCTGAGGCCGAGGCCACCTC
AGGCCCAGAGAAGAAGTGCGGCGGGGACCGAGCCCCCGGGCCAGAGCTGGGCCTGCCGAG
CACTGGGCAGCCGTCTGAGCAGGTCTGTCTCAGGCCTGGGGTTTCCGGGGAGGCACAAGG
CTCTGGCCCCGGGGAGGTGCTGCCCCACTGCTGCAGCTTGAAGGGTCCTCCCCAGAGCC
CAGCACCTGCCCCTCGGGCCTGGTCCCAGAGCCTCCGGAGCCCCAAGGCCCAGCCAAGGT
GCGGCCTGGGCCCAGCCCCAGCTGCTCCCAGTTTTTCCTGCTGACCCCGGTTCCGCTGAG
ATCAGAAGGCAACAGCTCTGAGTTCCAGGGGCCCCAGGACTGTTGTCAGGGCCGGCCCC
ACAAAAGCGGATGGGGGCCCAGGCACCCCAGAGCCCCACTCCGCCTGGCTCTGCCCGG
CCTCCCTGCGGCCTTGGAGGGCCGGCCGGAGGAGGAGGAGGAGGACAGTGAGGACAGCGA
CGAGTCTGACGAGGAGCTCCGCTGCTACAGCGTCCAGGAGCCTAGCGAGGACAGCGAAGA
GGAGGCGCCGGCGGTGCCCGTGGTGGTGGCTGAGAGCCAGAGCGCGCGCAACCTGCGCAG
CCTGCTCAAGATGCCCAGCCTGCTGTCCGAGACCTTCTGCGAGGACCTGGAACGCAAGAA
GAAGGCCGTGTCCTTCTTCGACGACGTCACCGTCTACCTCTTTGACCAGGAAAGCCCCAC
CCGGGAGCTCGGGGAGCCCTTCCCGGGCGCCAAGGAATCGCCCCTACGTTCCTTAGGGG
GAGCCCCGGCTCTCCCAGCGCCCCCAACCGGCCGCAGCAGGCTGATGGCTCCCCAAATGG
CTCCACAGCGGAAGAGGGTGGTGGGTTCGCGTGGGACGACGACTTCCCGCTGATGACGGC
CAAGGCAGCCTTCGCCATGGCCCTAGACCCGGCCGCACCCGCCCCGGCTGCGCCCACGCC
CACGCCCGCTCCCTTCTCGCGCTTCACGGTGTCGCCCGCGCCCACGTCCCGCTTCTCCAT
CACGCACGTGTCTGACTCGGACGCCGAGTCCAAGAGAGGACCTGAAGCTGGTGCCGGGGG
TGAGAGTAAAGAGGCTTGAGACCTGGGCAGCTCCTGCCCCTCAAGGCTGGCGTCACCGGA
GCCCCTGCCAGGCAGCAGCGAGGATGGTGACCGAGAAGGTGGGGACCACGTCCTGGTGGC
TGTTGGCAGCAGATTCAGGTGCCTCTGCCCCACGCGGTGTCCTGGAGAAGCCCGTGGGAT
GAGAGGCCCTGGATGGTAGATCGGCCATGCTCCGCCCCAGAGGCAGAATTCGTCTGGGCT
TTTAGGCTTGCTGCTAGCCCCTGGGGGCGCCTGGAGCCACAGTGGGTGTCTGTACACACA
TACACACTCAAAAGGGGCCAGTGCCCCTGGGCACGGCGGCCCCCACCCTCTGCCCTGCCT
GCCTGGCCTCGGAGGACCCGCATGCCCCATCCGGCAGCTCCTCCGGTGTGCTCACAGGAC
ACTTAAACCAGGACGAGGCATGGCCCCGAGACACTGGCAGGTTTGTGAGCCTCTTCCCAC
CCCCTGTGCCCCCACCCTTGCCTGGTTCCTGGTGGCTCAGGGCAAGGAGTGGCCCTGGGC
GCCCGTGTCGGTCCTGTTTCCGCTGCCCTTATCTCAAAGTCCGTGGCTGTTTCCCCTTCA
CTGACTCAGCTAGACCCGTAAGCCCACCCTTCCCACAGGGAACAGGCTGCTCCCACCTGG
GTCCCGCTGTGGCCACGGTGGGCAGCCCAAAAGATCAGGGGTGGAGGGGCTTCCAGGCTG
TACTCCTGCCCCGTGGGCCCCGTTCTAGAGGTGCCCTTGGCAGGACCGTGCAGGCAGCTC
CCCTCTGTGGGGCAGTATCTGGTCCTGTGCCCCAGCTGCCAAAGGAGAGTGGGGCCATG
CCCCGCAGTCAGTGTTGGGGGCTCCTACCTACAGGGAGAGGGATGGTGGGAAGGGGTG
GAGCTGGGGCAGGGCAGCACAGGGAATATTTTGTAACTAACTAACTGCTGTGGTTGGA
GCGAATGGAAGTTGGGTGATTTTAAGTTATTGTTGCCAAAGAGATGTAAAGTTTATTGTT
GCTTCGCAGGGGATTTGTTTTGTGTTTTGTTTGAGGCTTAGAACGCTGGTGCAATGTTT
TCTTGTTCCTTGTTTTTTAAGAGAAATGAAGCTAAGACAAAAGAAAAAAAAAAAAAAAA
Aactcgag
>
```

Fig. 6C

Nucleotide Sequences of LMRs

```
>>LMR1_m R25-39-10 (SEQ ID NO. 3)
gatGGCCACGGCTGGTTCGGAAAGGTATTTTTGGGGGAGGTACACTCGGGCGTCAGTGGC
ACGCAGGTGGTGGTGAAGGAGCTGAAGGTGAGCGCCAGCGTGCAGGAGCAGATGCAGTTC
CTGGAGGAGGCGCAGCCCTACAGGGCCCTGCAGCACAGCAACCTGCTCCAGTGCCTGGCC
CAGTGTGCTGAAGTGACCCCCTACCTGCTGGTTATGGAGTTCTGCCCATTCGGCGACCTg
aaatc
>

>>LMR2_r 2R22-7-13 (SEQ ID NO. 4)
gatGAGATCGGCTTTAAGGAGTTTGAAGATAATTTTGATGATGAGATAGACTTCACACCA
CCAGCAGAAGACACCCCCTCTGTCCAGTCCCCAGCAGAGGTCTTCACACTCTCAGTGCCA
AACATTTCACTTCCAGCCCCATCCCAGTTCCAGTCTTCTGTGGGTTTGAAGTCTCAGGTC
GCTCGCCACAGTCTAAACTATATACAGGAGATTGGGAATGGCTGGTTTGGGAAGGTGCTC
CTGGGAGAGACTTACACAGGCACCAGCGTCACAAGAGTCATAGTGAAGGAGTTAAAAGTC
AGTGCAAGCCCAAAGGAACAAGATACTTTCCTGAACAGTGGAGAGCCTTACTACATTCTT
CAGCATCCGAATGTTCTTCAGTGTGTCGGGCAGTGCGTGGAAGCCATTCCCTACCTTCTG
GTGTTTGAGTTCTGCGACCTGGGTGACCTGAAGGCTTACCTGCACAATGAACAAGAGCAC
GTGCGCAGCGAGTCACAGACCATGCTGCTGCAGAGGATGGCGTGCGAGATTGCCGCAGGG
CTGGCAGCCATGCACAAGCTGCACTTCCTGCACAGTGATCTGGCCCTACGGAACTGTTAT
CTCACCTCCGACCTAAACGTCAAAGTGGGTGACTATGGGATAGGCTTCAGCAGATATAAG
GAGGATTACATAGAGACGGATGACAAAAAAATTTTCCCCCTGAGATGGACTGCTCCAGAA
TTAGTGACCAGCTTTCAAGACAGACTCTTGACCGCAGATCAGACTAAGTACAGTAACATA
TGGACGCTAGGCGTGACAATC
>

>>LMR2_h (SEQ ID NO. 5)
gaattcggcacgagTCATGGCGGCGGGAGCGCGGCTTCCCAGGCCCGCCGCTCCGCAGGG
CTGCTGGCGTTGCTGCTGTTGAGAGGCGGCGGCGGCGGCGCAGGCGGGCGGGAAGGATGG
TGTTTCTGCGACTGGAGCGGCAGGTGCGGACCGGGAGCCGGACCGAGGTTTGGCAGAAGC
AACGTGTGCTCGGGAGCAACCGGCGCGGGTGCCACTGAGGCAGCGGAGGGAGGCAGGATC
GACTGACGGGCGAACGGACGGACGGACGGAAGGCGACTCGAGGGCCGGCCCCGGAGCCGC
GCCGTGGGCGAGATGCCGGGGCCGCCGGCGTTGCGGCGGAGGCTGCTGCTGCTGCTGCTG
GTCCTCCTGATCGCCGGCAGTGCTGGGCCGCGCCACTTCCGCAAACAGGTGCAGGGGAG
GCGCCACCTGCTGCAGAAGTTTCCTCATCTTTTGTGATCCTGTGTGTGTGCAGTTTAATA
ATATTAATAGTGTTAATTGCAAACTGTGTATCCTGCTGTAAGGACCCAGAAATAGACTTT
AAGGAATTTGAAGATAATTTTGATGATGAGATAGATTTCACACCACCAGCAGAAGACACT
CCCTCTGTTCAGTCCCCAGCAGAGGTCTTCACACTTTCAGTACCAAATATTTCACTCCCA
GCTCCCTCGCAATTCCAGCCTTCTGTAGAGGGATTGAAGTCTCAAGTTGCCCGCCACAGT
CTAAACTACATACAGGAAATTGGAAATGGCTGGTTTGGAAAGGTTCTCTTGGGAGAGATT
TACACGGGCACTAGCGTAGCAAGAGTCATCGTGAAGGAGTTAAAAGCAAGTGCCAACCCA
AAGGAACAAGATACTTTTTGAAAAATGGAGAACCTTACTACATTCTTCAGCATCCAAAT
ATTCTTCAGTGTGTTGGACAGTGCGTAGAAGCGATTCCCTACCTCCTGGTGTTTGAGTTC
TGTGACTTGGGTGACCTGAAGGCGTATCTGCGCAGCGAGCAGGAGCACATGCGGGGGAC
```

Fig. 6D

Nucleotide Sequences of LMRs

```
TCACAGACCATGCTGCTGCAGAGGATGGCGTGCGAGGTCGCCGCGGGGCTGGCCGCCATG
CACAAGCTGCACTTCCTGCACAGTGATTTAGCCCTGCGGAATTGTTTTCTCACCTCCGAC
TTAAATGTGAAAGTGGGAGATTACGGAATAGGATTCAGCAGGTACAAGGAGGATTATATT
GAAACAGATGATAAAAAGTTTTCCCTCTGCGATGGACTGCTCCAGAATTAGTAACCAGC
TTTCAAGACAGACTGCTAACTGCAGATCAGACTAAGTATAGTAATATCTGGTCTCTGGGT
GTGACACTTTGGGAGCTTTTTGACAATGCCGCACAGCCGTATTCAAACCTTTCCAACTTA
GATGTCCTCAACCAAGTCATTAGAGAGAGAGACACAAAACTCCCGAAGCCCCAGCTGGAG
CAGCCCTACTCTGATAGATGGTATGAAGTCTTACAGTTCTGTTGGCTGTCACCAGAAAAG
AGACCCGCGGCTGAAGATGTGCACAGGCTGCTGACTTACCTGCGGCTGCAGAGCCAGCGG
GACTCAGAGGTCGACTTTGAACAGCAGTGGAACGCTCTGAAGCCGAACACAAACAGCAGA
GACTCCTCCAACAATGCTGCATTCCCAATTCTCGACCACTTTGCCAGGGACCGGCTGGGT
CGTGAAATGGAGGAAGTCCTCACCGTGACCGAAACCAGCCAGGGCCTGAGCTTCGAGTAT
GTCTGGGAGGCCGCTAAGCACGACCACTTTGACGAGCGCAGCCGGGGCCACCTGGACGAA
GGCTTGTCCTACACGAGCATCTTCTATCCGGTTGAAGTTTTTGAGAGTTCGCTTTCAGAT
CCTGGGCCCGGAAAGCAAGATGACAGCGGCCAGGATGTCCCCCTGAGGGTCCCTGGAGTG
GTTCCTGTTTTTGATGCCCACAACCTTTCTGTTGGAAGCGACTATTATATCCAGTTAGAA
GAAAAAGTGGTAGTAACTTGGAGCTTGATTACCCACCAGCGCTGCTCACAACCGACATG
GATAATCCAGAAAGGACTGGCCCTGAACTGTCCCAGCTCACGGCGCTCAGGAGCGTTGAA
CTTGAGGAGTCCAGTACAGATGAGGACTTCTTCCAAAGCAGTACAGACCCCAAAGACTCT
AGCTTACCAGGGGACTTACACGTGACCAGTGGCCCCGAGAGCCCTTTCAACAATATATTT
AATGATGTGGACAAATCGGAAGATTTGCCCAGTCACCAAAAAATATTCGACTTAATGGAA
TTAAACGGAGTTCAAGCCGACTTTAAACCTGCCACTTTAAGTTCCAGTTTGGATAACCCC
AAAGAGTCAGTCATAACAGGCCACTTTGAGAAAGAAAAGCCCCGTAAGATTTTGACAGT
GAGCCTCTCTGCCTATCAGATAATCTTATGCACCAAGATAATTTTGATCCATTGAATGTT
CAAGAATTGTCAGAAAACTTTTTATTTCTTCAAGAGAAAAACTTACTAAAAGGCTCATTG
TCCAGCAAAGAACACATAAATGATCTTCAGACAGAACTTAAGAATGCTGGTTTTACTGAA
GCTATGTTAGAAACGTCATGTAGAAACTCTTTAGATACTGAGCTTCAGTTTGCTGAAAAT
AAGCCAGGCTTGTCTTTGTTGCAGGAAAACGTAAGCACAAAGGGTGACGATACAGATGTC
ATGCTCACAGGTGACACTTTGAGCACCTCATTGCAGTCTTCCCCGGAAGTGCAGGTACCT
CCTACCTCCTTCGAAACAGAAGAAACGCCCCGTCGGGTACCCCAGACTCACTCCCAACA
CAGGGAGAAACCCAGCCCACGTGTTTAGATGTTATTGTCCCGGAGGACTGTCTCCACCAG
GACATCAGTCCAGACGCTGTGACTGTCCCGGTTGAAATTCTCTCAACTGATGCCAGAACC
CACAGCCTGGATAACAGGTCCCAGGACTCTCCTGGCGAGAGTGAGGAGACCCTGCGACTC
ACCGAAAGTGACTCTGTTCTTGCTGATGACATCCTTGCCAGCAGGGTGAGTGTAGGGAGT
AGTCTCCCGGAACTGGGACAGGAATTGCACAATAAACCATTTTCGGAAGACCATCACAGT
CATCGCCGGCTAGAGAAAAACTTAGAGGCTGTGGAGACTTTAAATCAGCTCAATTCTAAA
GACGCAGCAAAGAAGCAGGCTTGGTGTCTGCCCTCTCCTCGGACTCAACCAGTCAGGAC
AGCCTCCTGGAGGACAGCTTGTCAGCACCCTTCCCAGCCTCTGAGCCGTCCCTGGAAACC
CCGGACTCTCTGGAGTCAGTGGATGTCCACGAAGCGCTACTGGACTCTTTAGGATCTCAC
ACTCCCCAGAAACTAGTGCCCCCGATAAGCCGGCAGACAGTGGCTACGAAACAGAGAAC
TTGGAGTCTCCCGAGTGGACCTTGCATCCCGCTCCCGAGGGCACCGCAGACTCAGAACCA
GCCACCACGGGCGATGGCGGCCACAGCGGTCTGCCTCCCAACCCGGTCATTGTCATCTCA
GATGCCGGCGATGGTCACAGAGGCACAGAAGTGACCCCTGAGACGTTCACAGCTGGCTCC
CAGGGTTCATACCGAGACTCTGCGTACTTCTCAGACAATGACTCTGAGCCCGAGAAAAGG
TCTGAGGAGGTCCCGGGAACCTCCCCATCCGCCTTGGTGTTGGTACAGGAGCAGCCCCTA
CCCGAGCCAGTCCTCCCCGAGCAAAGTCCTGCTGCCCAGGATAGCTGCCTGGAAGCCAGA
```

*Fig. 6E*

Nucleotide Sequences of LMRs

```
    AAGAGCCAGCCAGATGAAAGTTGTCTGTCTGCTTTGCACAACTCCAGTGACCTGGAATTA
    AGAGCCACGCCGGAGCCAGCACAGACTGGTGTTCCCCAGCAGGTGCATCCCACGGAAGAC
    GAGGCCAGCAGTCCCTGGAGTGTGCTGAATGCAGAACTTAGCAGCGGCGATGACTTCGAG
 5  ACACAGGACGATCGCCCTGCACCCTCGCTTCCACGGGGACCAACACGAACGAACTCCTT
    GCCTACACCAATTCTGCGCTGGACAAGTCCCTGTCCAGCCACTCCGAGGGCCCGAAGTTG
    AAGGAGCCGGACATCGAAGGGAAGTACCTGGGGAAACTCGGGGTGTCAGGGATGCTCGAC
    CTCTCAGAGGACGGGATGGATGCAGACGAGGAGGACGAAAACAGCGACGACTCGGACGAG
    GACCTGCGGGCCTTCAACCTGCATAGCCTCAGCTCCGAGTCGGAGGACGAGACCGAGCAC
10  CCCGTGCCCATCATCCTCAGCAACGAGGACGGAAGGCACCTGCGGAGTCTGTTGAAGCCC
    ACAGCGGCCAATGCCCCCGACCCACTGCCCGAGGACTGGAAGAAGGAAAAGAAGGCAGTC
    ACGTTTTTCGATGATGTCACAGTCTACCTGTTTGACCAGGAGACCCCAACCAAAGAGCTG
    GGGCCCTGTGGAGGAGAGGCGTGCGGCCCGGACCTGAGCGGCCCAGCCCCAGCCTCAGGC
    TCTCCCTACCTGAGCAGGTGCATCAACTCCGAAAGCTCCACCGACGAAGAAGGTGGTGGC
15  TTTGAGTGGGATGATGACTTCTCCCCAGATCCTTTTATGTCAAAGACAACAAGTAACCTG
    CTCAGCTCCAAGCCTTCTCTCCAAACATCCAAGTACTTTTCTCCGCCGCCACCGGCCCGG
    AGCACGGAGCAGAGCTGGCCGCACTCGGCGCCTTACTCCCGGTTCTCCATCTCTCCCGCC
    AACATTGCCAGCTTTTCCCTCACACACCTGACCGACTCGGACATCGAGCAGGGCGGAAGC
    AGCGAAGACGGAGAAAAGGACTAGGTGGCTGCCAACGCGCACGCTCGGGTCCGAGGCTGC
20  TCCCCTGGAGCGGCGCCCCTGCGCCCTCAGCCCGAGCAGCGACATCCACTCGCCATTTGC
    TGACATGAGATTGGGAGGAAGAATCCAGAGGTGAAGAGGGAGACGGCTCTTAGCTGCGTT
    CAAGGCGGGGCCCTCGGGAGCCCAGGTGCAGAGCGAGGCCGTGTCCAGGAGCCGGCGTCC
    CTCAGTGCCCCGTGCACCCGCGGCCGCGGCCTCCCAGGCAGTGCTCATGCGCTGGCCGTC
    GGGGGAGGCAGGGGCACAGCCTCCATGTGCGCGCGCGTGTGGAGCTGTGTGCACCGCATG
25  TGTGCTTTCCACAGGGGCGTCTCTGCGTCCACGCCTGCACATCCCGGCGCACGTGTGGGC
    ACCACAGAGGACACGTGAGGGGAATGGTCACCAGTGAGCCATATTTATTATTTCTAGAGA
    AATCACGAACTGCTTTCTGTAATTGCACTGTGGATAAATGTTCCGAGAGTCTCCATTGTT
    GTACAGGATCTTCAGTTATTCGAGGGGAATGAGGCAGGTCAAGCCGATGCTAGCCACTAG
    TTTGATTTTTTTTCTGTTTTATAGTTTGCGCTGCATGGTACTTGTGAAGCTTAAATATTT
30  TGAGTGTTCTACTGTGTCTAGGATTGTTGGATTGTACATATGGTACTCTTTCATAAATG
    ATAAATGATTCTGAATGTTAGTGTTTTATGTTCATATAGGAAATATTTTCATTGAGTCCA
    AAATACCACTGTTTTGTTGATGGACTTGAATGCATTTTTGTCTCTTCTTGATGAAGCGGC
    TTTGCCGCAGCAAATGAGGCTTCTCTCTGAGGAGCTGAGAGGTCTTGCAGCCTCTCCTTG
    TCATTCTCCCACCCCACATCCCATTTTTTAAAGCCCTTTTGGTAAAAACCAACAGGTTGT
35  GGCCGCAGACCTCAGATGGACCCGGCCCATCCCTGGGGACGTGCTGGCGTGGCAGGTCCA
    GAGAGCTGCACCCTGCACGGGGCACCGCACCGCTTCCCTCCGCGCAGCTCTTCTGCCTGG
    TTTTCGGAGGCCAGGCTGCTGGGAGGCTTCCGTGTTCCTGTCAGTCCTTCCTTCAAGAAG
    CCGGGGAACTCAGGCAGACTCATCTCCGCAGAGCATACCAGCCGTGGGGACCGTTCGAC
    TTGATGATGTGTGCACACTTCAGGTGGTGGGACTTGAGCTTTAAAAAAACCTCCACAGC
40  CGAATCTTCTCCTCCGAGCCACTCCACGTCACGTCCAGCTGGGCCTGGCCAGTCTGTGGT
    TATCCATGTGGGATGAGATAACACCACATCCTGCAGCTGTGAAGGGGATGGACAAGGGA
    CGACGGCCGACGGCAGAGCATCAGCAGCCGACACATAGTTCGGGTCGGGGCCTTGGGTGG
    TCCTGCATGGCCCGGGACTCATCTCACGGACCCTCCGTTCTGCATTAAGCCCCAGGTTCT
    CTTCTGGCTTTGAAAGGGCCCGAGTGCTCCCAGTGTAGCTTCGTCACATCGTCACGAGCC
45  CCTGTGGTCATGGGCGACCTCACACCTCCCTCCCTGAGTTCTGCTCTGACATAAGGAAGT
    CCTCGGTGGCTGGTGCAGCGCGGCTGTGCTGTGCTGGGGAGGCAGCCGTTCCTTCGGGGG
    TCCTTGGGCCTGCAGTCCCCTCATACTCACCCTTCACCCAACATATTTTCCGGTGCTGAT
```

*Fig. 6F*

Nucleotide Sequences of LMRs

```
    ATGTTTCCAGACTCCAGCGCAACCTGGGGTGCTCTCCAGACCCGTGCAGGGGCCGCCTGG
    GGTACACGGAAGGAAGTTGAGTCCTAGTGCAAAATGCAGGCGGACGTTGCCAGAGAGTGC
    GCAGCAAATGACCTTCATTGCCAGTTCCACCCTACTCCTCTCATTTTTTATACTAAGCAA
  5 TAACTTTCCAAAGCAAGAAGTTCAGGATGGAGAGAGTCCCCTCCTGTGTAGGCATGGGGT
    GGACGCGGTGCCCACCTGGGCTATGTGGGGAGCACCACTGTCTCGGGATGCGCGAATTTT
    TTTTTTTTTTTAATTAACAGGGCATTAGAAGATGATTTTGCCAAAATTGTCATGACTCTG
    AATTCTTGCTGTGGGGACTTCCTGAGTTTTCTCAGTTTTTACATCTAAGATTAGTCTTGG
    CTGAAGAGAAATGAGACGTGATTATACTACTTTTTCAATTGCAGGTTTAAGGAGTTCAGA
 10 TTTAATGACCAAAGTCATACAGATCATGGAATCTGTCGTCGTCTTATACAGTGTCAGCCT
    CGAGTACATTTATTAACCTTTTGGGGCTGTCAGTTTTCCACTAGGATTAAGATTTTGGCC
    GGGCGCGGTGGCTCACGCCTGCAATCCCAACACATTGGGGGGTCGAGGCGGACGGATCAC
    TTTGAGCCCAGGAGTTCAAGACCAGCCTGGGCAACATGGCGAAACCTCGTCTCTACTAAA
    AATACAAAATATATATATATATATACTAGCTGGGGCACATAGTGGTGTGCACCTGTAG
 15 TCCCAGCTGCTTGGGAGGCTGAGGTGGGAGGATGGCTAGAGCCCAGGAGATGGGTGTTGC
    AGTGAGCTGAGACCATGCCACTGTACTCTAGCCTGGGTAACAGCCAGACCCTGTCTCAAA
    AAAAAAACAATTTTTTTCATAACATAATTCCCATTTTTATTTATTTTGAGTCACTCATAA
    TTAATTGCCAAAAAGCATTTTATACATTGAGTTGGGGGGTAGTGGATCTTAGTGTGGTG
    TTGCATGGAGGGCGAGATTTTATATTTATAATCAACACGTGGGTTAACATGTTTTTTTG
 20 AAATCCAAGCAATACACAGGAAATTTAAGTAGAATAAAAATTGCAGCCCATTTTTGAAAT
    GTCAGCATGTGCTGTGTTCAGTTCAGGTTTTTGTTGTTTGTTTTGTTATTTTTAACTAA
    TAAGTTGGTTATCAGTGGTGGGTTTTCAAAATGTACTTGTTCTAATAAGTTGTACAATGA
    ACTAAATCAGTGGCATTCTCTAGATAATGTGGGGGAAGGTTAGAATATTTTCTGGCCTTC
    TATGGGGTAGCAACCCAGAATCAATCTGAATTAGTCCTGTTTTGGTGGAGTTTGTACATT
 25 TTAAATCCTATAACAAAAATAATCTAGTTTTCATTTCCTTACTAGCTAGATGCGAATTTG
    TCTTTTTGAATGACCCTGTCAATAAGCCAGAAAGGGCAACCCAGAAAAGTGCTCCCCAC
    ATCCTTCTGAGACTTGGCCTGTGTGTGTGGACGAGAAGCCATTCACCGTAAGGGTGCAGA
    AAGCTCGACCAAGCCGAATTGCAAACAACGTTCGTTCTATTTTAAATGTACAGGTTCGA
    TCGTTTCTATAGAAATGGGTTTATCTAAGAAAGTCTTGGTTTGTCTTGCTGCTGTAAAA
 30 GGCCTTTCCAAACCCCTCCTTTTATTCCTGTTTCCCGAAATAAGGTATTTGTAGAGTTAA
    GGACCTACTGCATGCCTGTCCCCAGGGCCCCGGTGGAAGGAAGGCAGCGCCTGCTCTTCC
    TTGACTCAGCCCATCATCTGAAAATTCAGAAGTGAACCAAGGGTTAGACGCCAGAGGTTG
    GGCTTCTGTTAGAGTGGCTTCAAAACATGAGCCTTATGGGAAGTAGCCTTAAAAAAAGAA
    TGGGTATACGCAGTGACTTCCGATGGAAATCTCCAAAACAATATTCCTAAGTAGCAATGG
 35 GGTTGGCTCAAGTCTTTATTAACAAAGAACATTCTCTTTCATCTATAAAGAAATTCTTAA
    AGATGCATTGACAGTGTTGAATTACCAACAGCCTGTGAAGATCAGTTTGACCGGTGTGGA
    CACGTGCTGGTTAAGCACTCAGGCCTACGTGGGCCGAGCGGGATCTTGATCATGGGGCTG
    GTGTATGGATCCACCGTCGGATTCCGTCTGCAGAGGAGGACGTAGGGGCCGTCACACCC
    ACCAGGCCTCCCTGCTGTGCTTTAACACAGGCAGAAGAGGTTCATGGCAATATAATAGTC
 40 AATGAACTTTCAGTTTAAATTGTGTACATTTTAAATTGTAAGATTTTTACTGTATATTG
    ATGCATAGTGTGATTCAATAAATTGCTTGTAATTTAAAAACTATTTAATATTCAAAATAA
    ATATAGTTATATATTTATAAAAAAAAAAAAAAAActcgag
    >
```

Fig. 6G

Nucleotide Sequences of LMRs

>>LMR2_m R25-38-16 (SEQ ID NO. 6)
gatGGCCACGGCTGGTTTGGCAAGGTTTTCCTGGGAGAGACTTACACAGGCACCAGCGTC
GCGAGAGTCATAGTGAAGGAGTTAAAAGTCAGTGCAAGCCCCAAGGAGCAGGACACTTTC
CTGAAGAGTGGAGAGCCTTACTACATCCTCCAGCATCCAAATGTCCTCCAGTGTGTGGGG
CAGTGTGTGGAAGCCATCCCCTACCTTCTGGTGTTTGAATTTTGCCCATTTGGCGACCTg
aaatc >>LMR3_r 2R22-6-16 (SEQ ID NO. 7)
gatGAGATCGGGTTTAAAGAGTTCGAGAATCCGGAAGGGGAGGACTGCTCTGGGGAGTAC
ACCCCCCCTGCGGAGGAGACCTCCTCCTCACAGTCGCTGCCTGATGTCTATATTCTGCCG
CTGGCAGAGGTCTCACTGCCAATGCCTGCCCCGCAGCCTGCACACTCAGACATCAGCACC
CCCCTGGGCCTGAGCCGCCAGCACCTCAGCTACCTGCAGGAGATTGGCAGCGGCTGGTTT
GGGAAGGTGATCCTCGGGGAGGTTTTCTCAGACTACTCGCCAGCGCAGGTGGTGGTGAAG
GAACTCCGGGCTAGTGCAGGGCCCCTGGAGCAGCGCAAGTTCATCTCAGAGGCTCAGCCC
TACAGGAGCCTGCAGCATCCCAACGTCCTCCAGTGCCTGGGTGTCTGTGTGGAGACCTTG
CCCTTCCTGTTGATCATGGAGTTCTGCCAGCTGGGGGACCTGAAGCGATACCTTCGGGCC
CAGCGGCCACCTGAAGGCATGTCCCCTGAACTTCCCCCACGAGACCTTCGGACATTACAG
AGGATGGGCCTAGAGATTGCCCGAGGACTGGCACACCTGCACTCCACAACTACGTGCAC
AGCGATCTGGCGCTGCGCAACTGCCTGCTAACTTCAGACCTGACTGTGCGTATTGGAGAC
TATGGGCTGGCGCATAGCAACTACAAGGAAGACTACTACCTGACACCCGAGCGCCTATGG
GTGCCGCTGCGCTGGGCAGCGCCCGAGCTGCTGGGCGAGCTGCACGGCAGCTTTGTGCTA
GTGGATCAAAGCCGTGAGAGTAACATCTGGACCCTAGGGGTGACAATC >>LMR3_h (SEQ ID NO. 8)
gaattcCGGGGCTGGGTCGCCTGCGCCGAGTGTTGCTGAGGCTGCGTCTTGGGTGCGCAG
CTCCGGCCCAGCCTCACCCAGGGGAACGCCTCGCAGGTGCTCACGGACGATGGAGAGCCG
CCACCACCTCCACCTCCCTGCCATCCTCGACAAGATGCCTGCCCCCGGCGCCCTCATCCT
CCTTGCGGCCGTCTCCGCCTCCGGCTGCCTGGCGTCCCCGGCCCACCCCGATGGATTCGC
CCTGGGCCGGGCTCCTCTGGCTCCTCCCTACGCTGTGGTCCTCATTTCCTGCTCCGGCCT
GCTGGCCTTCATCTTCCTCCTCCTCACCTGTCTGTGCTGCAAACGGGGCGATGTCGGCTT
CAAGGAATTTGAGAACCCTGAAGGGGAGGACTGCTCCGGGGAGTACACTCCCCCTGCGGA
GGAGACCTCCTCCTCACAGTCGCTGCCTGATGTCTACATTCTCCCGCTGGCTGAGGTCTC
CCTGCCAATGCCTGCCCCGCAGCCTTCACACTCAGACATGACCACCCCCtGGGCCTTAG
CCGGCAGCACCTGAGCTACCTGCAGGAGATTGGGAGTGGCTGGTTTGGGAAGGTGATCCT
GGGAGAGATTTTCTCCGACTACACCCCCGCCCAGGTGGTGGTGAAGGAGCTCCGAGCCAG
CGCGGGGCCCCTGGAGCAACGCAAGTTCATCTCGGAAGCACAGCCGTACAGGAGCCTGCA
GCACCCCAATGTCCTCCAGTGCCTGGGTCTGTGCGTGGAGACGCTGCCGTTTCTGCTGAT
TATGGAGTTCTGTCAACTGGGGGACCTGAAGCGTTACcTCCGAGCCCAGCGGCCCCCCGA
GGGCCTGTCCCCTGAGCTACCCCCTCAGAGACCTGCGGACGCTGCAGAGGATGGGCCTGGA
GATCGCCCGCGGGCTGGCGCACCTGCATTCCCACAACTACGTGCACAGCGACCTGGCCCT
GCGCAACTGCCTGCTGACCTCTGACCTGACCGTGCGCATCGGAGACTACGGGCTGGCCCA
CAGCAACTACAAGGAGGACTACTACCTGACCCCAGAGCGCCTGTGGATCCCACTGCGCTG
GGCGGCGCCCGAGCTCCTCGGGGAGCTCCACGGGACCTTCATGGTGATGGACCAGAGCCG
CgAgAGCAACATCTGGTCCCTGGGGGTGACCCTGTGGGAGCTGTTTGAGTTTGGGGCCCA
GCCCTACCGCCACCTGTCAGACGAGGAGGTCCTCGCCTTCGTGGTCCGCCAGCAGCATGT

Fig. 6H

Nucleotide Sequences of LMRs

```
  GAAGCTGGCCCGGCCGAAGCTCAAGCTGCCTTACGCGGACTACTGGTATGACATTCTTCA
  GTCCTGCTGGCGGCCACCTGCCCAGCGCCCTTCAGCCTCTGATCTCCAATTGCAGCTCAC
  CTACTTGCTCTCCGAGCGGCCTCCCCGGCCCCCACCGCCGCCACCCCCACCCCGAGACGG
5 TCCCTTCCCCTGGCCCTGGCCCCCTGCACACAGTGCGCCCCGCCCGGGGACCCTCTCCTC
  ACCGTTCCCCCTACTGGATGGCTTCCCTGGAGCCGACCCCGACGATGTGCTCACGGTCAC
  CGAGAGTAGCCGCGCCGgaattc >>LMR3_m R24-14U-4 (SEQ ID NO. 9)
10 gatGAGATCGGGTTTAAAGAGTTCGAGAATCCGGAAGGGGAGGACTGCTCTGGGGAGTAC
  ACCCCCCCTGCGGAGGAGACCTCCTCCTCACAGTCGCTGCCTGATGTCTATATTCTGCCG
  CTGGCAGAGGTCTCACTGCCAATGCCTGCCCCGCAGCCTGCACACTCAGACATCAGCACC
  CCCCTGGGCCTGAGCCGCCAGCACCTCAGCTACCTGCAGGAGATTGGCAGCGGCTGGTTT
  GGGAAGGTGATCCTCGGGGAGGTTTTCTCAGACTACTCGCCAGCGCAGGTGGTGGTGAAG
15 GAACTCCGGGCTAGTGCAGGGCCCCTGGAGCAGCGCAAGTTCATCTCAGAGGCTCAGCCC
  TACAGGAGCCTGCAGCATCCCAACGTCCTCCAGTGCCTGGGTGTCTGTGTGGAGACCTTG
  CCCTTCCTGTTGATCATGGAGTTCTGCCAGCTGGGGGACCTGAAGCGATACCTTCGGGCC
  CAGCGGCCACCTGAAGGCATGTCCCCTGAACTTCCCCCACGAGACCTTCGGACATTACAG
  AGGATGGGCCTAGAGATTGCCCGAGGACTGGCACACCTGCACTCCCACAACTACGTGCAC
20 AGCGATCTGGCGCTGCGCAACTGCCTGCTAACTTCAGACCTGACTGTGCGTATTGGAGAC
  TATGGGCTGGCGCATAGCAACTACAAGGAAGACTACTACCTGACACCCGAGCGCCTATGG
  GTGCCGCTGCGCTGGGCAGCGCCCGAGCTGCTGGGCGAGCTGCACGGCAGCTTTGTGCTA
  GTGGATCAAAGCCGTGAGAGTAACATCTGGACCCTAGGGGTGACAATC
```

*Fig. 6I*

Amino Acid Sequences of LMRs

>>LMR1_r (SEQ ID NO. 10)
MPIALLALAMSSSFFNPSFAFSSHFDPDGAPLSELSWSSSLAVVAVSFSGIFTVIVLMLAC
LCCKKGGIGFKEFENAEGEEYVADFSEQGSPAATVQNGPDVYVLPLTEVSLPMAKQPGRSV
QLLKSTDLGRHSLLYLKEIGHGWFGKVFLGEVHSGVSGTQVVVKELKASASVQEQMQFLEE
AQPYRALQHSNLLQCLAQCAEVTPYLLVMEFCPLGDLKGYLRSCRVTESMAPDPLTLQRMA
CEVACGVLHLHRHNYVHSDLALRNCLLTADLTVKVGDYGLAHCKYREDYLVTADQLWVPLR
WIAPELVDEVHGNLLVVDQTKTSNVWSLGVTIWELFELGAQPYPQHSDRQVLAYAVREQQL
KLPKPQLQLTLSDRWYEVMQFCWLQPEQRPTAEEVHLLLSYLCAKGTTELEEEFERRWRSL
RPGGSAGLGSASTVPAAAASELTAASSFPLLEQFTSDGFHVDSDDVLTVTETSHGLNFEYK
WEAGCGAEAYPPPGAAFSPGSAGRLQELCAPDSSPPGVVPVLSAHSPSVGSEYFIRLEGAV
PAAGHDPDCAGCAPSPQAVSEQDNNSEESTAASLVMEPLLGHAPPTGGLWGPCDHHSRRRQ
EPPCPSRSPSPGTPMLPAEDIDWGVATFCPPFFDDPLGTSPSGSPGAQPSPSDEELEEGKT
GRAAQCGHWSSNMSANNNSGSRDPESWDPGYVSSFTDSYRDDCSSLEQTPRASPELGHPLS
QEDSRDFLPGLVAASPGQESSRCFNLLPLCPAKGLAPAACLVPPPWTEAAVGGAENPIVEP
KLAQEAEGSAEPQLPLPSVPSPSHEGASLPSEEASAPDIQPASPTPAAGSWVTVL

>>LMR1_h (first 27 aa derived from rat cDNA) (SEQ ID NO. 11)
>mpiallalamsssffnPSFAFSSHFDPDGAPLSELSWASSLAVVAVSFSGLFAVIVLMLA
CLCCKKGGIGFKEFENAEGEEYVADFSEQGSPAATVQNGPDVYVLPLTEVSLPMAKQPGRS
VQLLKSTDVGRHSLLYLKEIGRGWFGKVFLGEVNSGISSAQVVVKELQASASVQEQMQFLE
EVQPYRALKHSNLLQCLAQCAEVTPYLLVMEFCPLGDLKGYLRSCRVAESMAPDPRTLQRM
ACEVACGVLHLHRNNFVHSDLALRNCLLTADLTVKIGDYGLAHCKYREDYFVTADQLWVPL
RWIAPELVDEVHSNLLVVDQTKSGNVWSLGVTIWELFELGTQPYPQHSDQQVLAYTVREQQ
LKLPKPQLQLTLSDRWYEVMQFCWLQPEQRPTAEEVHLLLSYLCAKGATEAEEEFERRWRS
LRPGGGGVGPGPGAAGPMLGGVVELAAASSFPLLEQFAGDGFHADGDDVLTVTETSRGLNF
EYKWEAGRGAEAFPATLSPGRTARLQELCAPDGAPPGVVPVLSAHSPSLGSEYFIRLEEAA
PAAGHDPDCAGCAPSPPATADQDDDSDGSTAASLAMEPLLGHGPPVDVPWGRGDHYPRRSL
ARDPLCPSRSPSPSAGPLSLAEGGAEDADWGVAAFCPAFFEDPLGTSPLGSSGAPPLPLTG
EDELEEVGARRAAQRGHWRSNVSANNNSGSRCPESWDPVSAGCHAEGCPSPKQTPRASPEP
GYPGEPLLGLQAASAQEPGCCPGLPHLCSAQGLAPAPCLVTPSWTETASSGGDHPQAEPKL
ATEAEGTTGPRLPLPSVPSPSQEGAPLPSEEASAPDAPDALPDSPTPATGGEVSAIKLASA
LNGSSSSPEVEAPSSEDEDTAEATSGIFTDTSSDGLQARRPDVVPAFRSLQKQVGTPDSLD
SLDIPSSASDGGYEVFSPSATGPSGGQPRALDSGYDTENYESPEFVLKEAQEGCEPQAFAE
LASEGEGPGPETRLSTSLSGLNEKNPYRDSAYFSDLEAEAEATSGPEKKCGGDRAPGPELG
LPSTGQPSEQVCLRPGVSGEAQGSGPGEVLPPLLQLEGSSPEPSTCPSGLVPEPPEPQGPA
KVRPGPSPSCSQFFLLTPVPLRSEGNSSEFQGPPGLLSGPAPQKRMGGPGTPRAPLRLALP
GLPAALEGRPEEEEDSEDSDESDEELRCYSVQEPSEDSEEEAPAVPVVVAESQSARNLRS
LLKMPSLLSETFCEDLERKKKAVSFFDDVTVYLFDQESPTRELGEPFPGAKESPPTFLRGS
PGSPSAPNRPQQADGSPNGSTAEEGGGFAWDDDFPLMTAKAAFAMALDPAAPAPAAPTPTP
APFSRFTVSPAPTSRFSITHVSDSDAESKRGPEAGAGGESKEA >>LMR1_m R25-39-10 (SEQ ID NO. 12)
>GHGWFGKVFLGEVHSGVSGTQVVVKELKVSASVQEQMQFLEEAQPYRALQHSNLLQCLAQ
CAEVTPYLLVMEFCPFGDLK

Fig. 7A

Amino Acid Sequences of LMRs

>>LMR2_r 2R22-7-13 (SEQ ID NO. 13)
>EIGFKEFEDNFDDEIDFTPPAEDTPSVQSPAEVFTLSVPNISLPAPSQFQSSVGLKSQVA
RHSLNYIQEIGNGWFGKVLLGETYTGTSVTRVIVKELKVSASPKEQDTFLNSGEPYYILQH
PNVLQCVGQCVEAIPYLLVFEFCDLGDLKAYLHNEQEHVRSESQTMLLQRMACEIAAGLAA
MHKLHFLHSDLALRNCYLTSDLNVKVGDYGIGFSRYKEDYIETDDKKIFPLRWTAPELVTS
FQDRLLTADQTKYSNIWTLGVTI

>>LMR2_h (SEQ ID NO. 14)
>MPGPPALRRRLLLLLLVLLIAGSAGAAPLPQTGAGEAPPAAEVSSSFVILCVCSLIILIV
LIANCVSCCKDPEIDFKEFEDNFDDEIDFTPPAEDTPSVQSPAEVFTLSVPNISLPAPSQF
QPSVEGLKSQVARHSLNYIQEIGNGWFGKVLLGEIYTGTSVARVIVKELKASANPKEQDTF
LKNGEPYYILQHPNILQCVGQCVEAIPYLLVFEFCDLGDLKAYLRSEQEHMRGDSQTMLLQ
RMACEVAAGLAAMHKLHFLHSDLALRNCFLTSDLNVKVGDYGIGFSRYKEDYIETDDKKVF
PLRWTAPELVTSFQDRLLTADQTKYSNIWSLGVTLWELFDNAAQPYSNLSNLDVLNQVIRE
RDTKLPKPQLEQPYSDRWYEVLQFCWLSPEKRPAAEDVHRLLTYLRLQSQRDSEVDFEQQW
NALKPNTNSRDSSNNAAFPILDHFARDRLGREMEEVLTVTETSQGLSFEYVWEAAKHDHFD
ERSRGHLDEGLSYTSIFYPVEVFESSLSDPGPGKQDDSGQDVPLRVPGVVPVFDAHNLSVG
SDYYIQLEEKSGSNLELDYPPALLTTDMDNPERTGPELSQLTALRSVELEESSTDEDFFQS
STDPKDSSLPGDLHVTSGPESPFNNIFNDVDKSEDLPSHQKIFDLMELNGVQADFKPATLS
SSLDNPKESVITGHFEKEKPRKIFDSEPLCLSDNLMHQDNFDPLNVQELSENFLFLQEKNL
LKGSLSSKEHINDLQTELKNAGFTEAMLETSCRNSLDTELQFAENKPGLSLLQENVSTKGD
DTDVMLTGDTLSTSLQSSPEVQVPPTSFETEETPRRVPPDSLPTQGETQPTCLDVIVPEDC
LHQDISPDAVTVPVEILSTDARTHSLDNRSQDSPGESEETLRLTESDSVLADDILASRVSV
GSSLPELGQELHNKPFSEDHHSHRRLEKNLEAVETLNQLNSKDAAKEAGLVSALSSDSTSQ
DSLLEDSLSAPFPASEPSLETPDSLESVDVHEALLDSLGSHTPQKLVPPDKPADSGYETEN
LESPEWTLHPAPEGTADSEPATTGDGGHSGLPPNPVIVISDAGDGHRGTEVTPETFTAGSQ
GSYRDSAYFSDNDSEPEKRSEEVPGTSPSALVLQEQPLPEPVLPEQSPAAQDSCLEARKS
QPDESCLSALHNSSDLELRATPEPAQTGVPQQVHPTEDEASSPWSVLNAELSSGDDFETQD
DRPCTLASTGTNTNELLAYTNSALDKSLSSHSEGPKLKEPDIEGKYLGKLGVSGMLDLSED
GMDADEEDENSDDSDEDLRAFNHLSLSSESEDETEHPVPIILSNEDGRHLRSLLKPTAANA
PDPLPEDWKKEKKAVTFFDDVTVYLFDQETPTKELGPCGGEACGPDLSGPAPASGSPYLSR
CINSESSTDEEGGGFEWDDDFSPDPFMSKTTSNLLSSKPSLQTSKYFSPPPPARSTEQSWP
HSAPYSRFSISPANIASFSLTHLTDSDIEQGGSSEDGEKD

>>LMR2_m R25-38-16 (SEQ ID NO. 15)
>GHGWFGKVFLGETYTGTSVARVIVKELKVSASPKEQDTFLKSGEPYYILQHPNVLQCVGQ
CVEAIPYLLVFEFCPFGDLK

>>LMR3_r 2R22-6-16 (SEQ ID NO. 16)
>EIGFKEFENPEGEDCSGEYTPPAEETSSSQSLPDVYILPLAEVSLPMPAPQPAHSDISTP
LGLSRQHLSYLQEIGSGWFGKVILGEVFSDYSPAQVVVKELRASAGPLEQRKFISEAQPYR
SLQHPNVLQCLGVCVETLPFLLIMEFCQLGDLKRYLRAQRPPEGMSPELPPRDLRTLQRMG
LEIARGLAHLHSHNYVHSDLALRNCLLTSDLTVRIGDYGLAHSNYKEDYYLTPERLWVPLR
WAAPELLGELHGSFVLVDQSRESNIWTLGVTI

*Fig. 7B*

Amino Acid Sequences of LMRs

>>LMR3_h (SEQ ID NO. 17)
>MPAPGALILLAAVSASGCLASPAHPDGFALGRAPLAPPYAVVLISCSGLLAFIFLLLTCL
CCKRGDVGFKEFENPEGEDCSGEYTPPAEETSSSQSLPDVYILPLAEVSLPMPAPQPSHSD
MTTPLGLSRQHLSYLQEIGSGWFGKVILGEIFSDYTPAQVVVKELRASAGPLEQRKFISEA
QPYRSLQHPNVLQCLGLCVETLPFLLIMEFCQLGDLKRYLRAQRPPEGLSPELPPRDLRTL
QRMGLEIARGLAHLHSHNYVHSDLALRNCLLTSDLTVRIGDYGLAHSNYKEDYYLTPERLW
IPLRWAAPELLGELHGTFMVMDQSRESNIWSLGVTLWELFEFGAQPYRHLSDEEVLAFVVR
QQHVKLARPKLKLPYADYWYDILQSCWRPPAQRPSASDLQLQLTYLLSERPPRPPPPPPP
RDGPFPWPWPPAHSAPRPGTLSSPFPLLDGFPGADPDDVLTVTESS

>>LMR3_m R24-14U-4 (SEQ ID NO. 18)
>REFRSGAGPLEQRKFISEAQPYRSLQRPNVLQCLGVCVETLPFLLIMEFCQLGDLKRYLR
AQRPPEGMSPELPPRDLRTLQRMGLEIARGLAHLHSHNYVHSDLALRNCLLTSDLTVRIGD
YGLAHSNYKEDYYLTPERLWVPLRWAAPELL
GELHGSFVLVDQSRESNVWSLGVTII

>>LMR2_h peptide 489A (SEQ ID NO. 19)
DSDIEQGGSSEDGEKD

>>LMR2_h peptide 491A (SEQ ID NO. 20)
DDEIDFTPPAEDTPS

>>LMR2_h peptide 491A (SEQ ID NO. 21)
HFEKEKPRKIFDSEP

>>LMR2_h peptide 491A (SEQ ID NO. 22)
GSYRDSAYFSDNDSEP

*Fig. 7C*

KINASE GENES AND USES

RELATED APPLICATION

This application claims the benefit of Joho et al., United States Provisional Application No. 60/031,675, entitled KINASE GENES AND USES, filed Nov. 22, 1996, which is hereby incorporated by reference in its entirety including drawings.

FIELD OF THE INVENTION

The present invention relates to novel, related tyrosine kinases. In particular, this includes polynucleotide sequences corresponding to human and rodent messenger RNA (mRNA), to the corresponding complementary DNA (cDNA) sequences, and to the encoded polypeptides.

BACKGROUND OF THE INVENTION

The following description of the background of the invention is provided solely to aid the understanding of the reader. None of the information provided or references cited is admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function. For reviews, see Posada and Cooper, *Mol. Biol. Cell*, 3:583–392 (1992) and Hardie, *Symp. Soc. Exp. Biol.* 44:241–255 (1990)). The best characterized protein kinases in eukaryotes phosphorylate proteins on the alcohol moiety of serine, threonine and tyrosine residues. These kinases largely fall into two groups, those specific for phosphorylating serines and threonines, and those specific for phosphorylating tyrosines. The tyrosine kinases can be further divided into receptor and non-receptor proteins.

Protein kinases are one of the largest families of eukaryotic proteins with several hundred known members. Alignment of primary peptide sequences of these proteins shows that they share a 250–300 amino acid domain that can be subdivided into 12 distinct subdomains (I–XII) that comprise the common catalytic core structure. These conserved protein motifs have recently been exploited using PCR-based cloning strategies leading to a significant expansion of the known kinases. Multiple alignment of the sequences in the catalytic domain of protein kinases and subsequent phylogenetic analysis permits their segregation into a phylogenetic tree. In this manner, related kinases are clustered into distinct branches or subfamilies including: tyrosine kinases, cyclic-nucleotide-dependent kinases, calcium/calmodulin kinases, cyclin-dependent kinases and MAP-kinases, as well as several other less defined subfamilies. (See Hanks and Hunter, *FASEB J.* 9:576–595 (1995).

Receptor tyrosine kinases (RTKs) belong to a family of transmembrane proteins and have been implicated in numerous cellular signaling pathways. The predominant biological activity of some RTKs is the stimulation of cell growth and proliferation, while other RTKs are involved in promoting differentiation. In some instances, a single tyrosine kinase can inhibit or stimulate cell proliferation depending on the cellular environment in which it is expressed. RTKs are composed of at least three domains: an extracellular ligand binding domain, a transmembrane domain and a cytoplasmic domain containing at least one enzymatic domain capable of phosphorylating tyrosine residues. Ligand binding to membrane bound receptors induces the formation of receptor dimers and allosteric changes that activate the intracellular kinase domains and result in the self-phosphorylation (autophosphorylation and/or transphosphorylation) of the receptor on tyrosine residues. RTKs are also known to form heterodimers. A possible role for receptor heterodimerizaion is described in Carraway and Cantley, *Cell* 78:5–8 9 (1994).

The non-receptor tyrosine kinases do not contain a transmembrane domain or an extracellular domain and share non-catalytic domains in addition to sharing their catalytic kinase domains. Such non-catalytic domains include the SH2 domain (Src homology domain 2) and SH3 domains (Src homology domain 3). The non-catalytic domains are thought to be important in the regulation of protein-protein interactions during signal transduction.

Receptor tyrosine kinases are known to play a role in the proliferation, differentiation and/or survival of many cell types. One example is the Trk family of receptors. The Trks are receptors for several known neurotrophic factors including nerve growth factor (NGF). Binding of NGF to TrkA induces phosphorylation of the receptor and subsequent differentiation of the PC12 pheochromocytoma cell line, a model for neuronal development. (Kaplan, et al, *Science* 252:554–558 (1991); Yan, et al, *Science* 252:561–563 (1991)). Other members of the Trks family include TrkB and TrkC, which are expressed in a variety of structures in nervous system and respond to binding of other neurotrophic factors such as brain-derived neurotrophic factor and neurotrophin-3 (Klein, et al Development 109:845–850 (1990); Glass, et al Cell 66:405–413 (1991); Klein, et al *Cell* 66:395–403 (1991)).

Several RTKs and growth factors were originally identified as activated oncogenes (*Aaronson, Science* 254:1146–1153 (1991); Bishop, *Cell* 64:235–248 (1991)) and there has long been a belief that some RTKs may be involved in the development of cancers. Several studies appear to support this notion. These include the high correlation of RTK overexpression with certain human cancers including HER2 with breast and ovarian cancers (Slamon, et al., *Science* 235:177–182 (1987)), PDGF and its receptors with a high fraction of sarcomas and glially derived neoplasms, and EGF-R with squamous cell carcinomas and glioblastomas (reviewed in Aaronson, (1991)).

Several RTKs have been associated with the growth and development of lung cancer cells including c-kit (Hida, et al *Int. J. Can.* 0 (supp 8):108–109 (1994); Krystal, et al, *Can. Res.* 56(2);370–376 (1996)), trk (Oelmann, et al *Can. Res.* 55(10):2212–2219 (1995)), Her2/neu (Tsai, et al *Can. Ras.* 56 (5):1068–1074 (1996)) and EGF-R (Moody, Peptides 17(3):545–555 (1996)). The identification of a lung cancer specific RTK would be advantageous for the development of specific drugs that could inhibit the signal transduction activity of the RTK thereby suppressing the RTK driven growth of the cancer.

SUMMARY OF THE INVENTION

The present invention concerns nucleic acid molecules, each of which corresponds to at least a portion of a unique expressed mammalian gene coding for a tyrosine kinase. Possession of just a portion of a nucleic acid sequence of a gene corresponding to a particular kinase provides a specific probe, allowing the mapping of the gene to a specific chromosome, the mapping of the gene to a position on that chromosome, and identification of clones, such as from a complementary (cDNA) or genomic library, containing the complementary sequence. In addition, possession of a sequence corresponding to a particular gene allows the determination of the expression pattern of that gene, thereby providing valuable information on the biology of relevant tissues. The analysis can also partially characterize some disease states, notably cancers, since cancers represent improperly regulated cell proliferation and, therefore, often involve abnormal kinase gene expression. The genes disclosed herein appear to define a novel group of related receptor tyrosine kinases that are highly expressed in neuronal tissues. Several of these novel genes are also highly expressed in cancerous tissues, in particular lung and ovarian cancers. One gene does not appear to be expressed in any normal tissue but is expressed in a variety of tumor types suggesting it may play a role in forming or maintaining the cancer.

Thus, possession of a portion of one of the disclosed sequences or a sequence complementary to a portion of one of those sequences, having a length greater than about 13 or 17 bases in length, preferably, 25, 50, or 100 bases in length, uniquely identifies the corresponding gene, since the sequence of the partial nucleic acid sequence corresponds to a portion of the sequence of the corresponding gene and not to any other gene except essentially equivalent ones. Even if the stated sequence of the partial nucleic acid sequence differs by a small percentage, e.g., by less than about 3% or 1%, from the sequence of the actual nucleotide sequence, the unique identification of the gene is still provided, since the stringency of the hybridization conditions can be adjusted to allow a low level of mismatch. Thus, a probe having the sequence of a portion of one of the stated sequences will still uniquely hybridize with the respective corresponding gene under appropriately stringent hybridizing conditions.

In addition, possession of a specific DNA probe provides longer DNA sequences of the gene, including the full length sequence of a cDNA and the full cDNA corresponding to a full-length, mature messenger RNA (mRNA), or a useful portion thereof, or a full-length copy of the genomic gene sequence, because those longer sequences can be obtained by routine procedures utilizing the specific probe.

Thus, in this invention, nucleic acid sequences corresponding to specific receptor tyrosine kinase genes are provided. The sequences were identified as coding for tyrosine kinases by sequence analysis based on previously identified tyrosine kinases, as described in detail below. Each sequence is uniquely characteristic of the gene from which it is derived, and provides for the isolation of the complete coding sequence of the gene by standard procedures. Thus, this invention specifically identifies and provides such genes. Such genes can be cloned by standard techniques into vectors and used for screening, diagnostic, or therapeutic procedures, among other uses. Generally, the DNA is cloned into a vector which is specifically designed to express the cloned gene in a useful manner, or to allow specific detection of the desired target nucleic acid.

Specifically, in a first aspect, this invention provides purified, enriched or isolated nucleic acid molecules at least 25 nucleotides in length, corresponding to expressed mammalian genes encoding one of a group of related tyrosine kinases. The nucleic acid molecules encode tyrosine kinase polypeptides, each of which has an amino acid sequence which is part of the amino acid sequence of a tyrosine kinase encoded by one of the genes corresponding to one of SEQ ID NO. 1–9. Each such nucleic acid molecule has at least 95% sequence identity to the corresponding portion of the gene, or to the complementary sequence.

In a related aspect, a purified, isolated, or enriched nucleic acid molecule has at least 95k sequence identity to a portion of one of SEQ ID NO. 1–9, or a sequence complementary thereto. Preferably, the sequence identity is higher, for example, at least 97% or 99% or 100%. The nucleic molecules include single strand DNA (ssDNA), double strand DNA (dsDNA), and RNA. The nucleic acid is preferably DNA, and is preferably at least 13 nucleotides in length, more preferably at least 20–30 nucleotides in length, and most preferably at least 50 nucleotides in length. The nucleic acid can specifically hybridize under stringent conditions to a DNA chain having a sequence listed in SEQ ID NO 1–9, or a sequence complementary thereto, or to a gene encoding a kinase which corresponds to any of SEQ ID NO. 1–9. In preferred embodiments of the above aspects, the nucleic and molecule is longer, such as at least 50, 100, 200, 400 on more nucleotides in length.

The sequence of the nucleic acid molecule can be determined and confirmed by redundant sequencing of both complementary strands of a corresponding cDNA using standard, routine sequencing techniques. Such redundant sequencing allows a researcher to eliminate sequence errors which might occur with single pass sequencing and which may be present in some sequences provided herein.

Such a nucleic acid molecule is useful as a unique probe for determining the location and expression of a corresponding human gene, cDNA, or mRNA. Therefore, such probe reagents are useful in the analysis of human biology and in the development of new therapeutics as tools to aid mapping and analysis of genes, mRNAs, and polypeptide expression products. Such probes include a nucleic acid sequence of a portion of one of the genes indentified herein, or a sequence complementary thereto, and may also contain additional nucleic acid sequences and/or labels or other components which do not prevent specific hybridization.

In addition, such a nucleic acid molecule is useful as a source of primers for copying, transcribing, or reverse transcribing the complementary DNA or RNA. The hybridization of such nucleic acid molecule to the corresponding specific site of the human genomic DNA, cDNA, or mRNA can be performed under commonly used conditions (see e.g. Sambrook, J. et al., Molecular Cloning: A Laboratory Manual (1989).

Thus, once a person skilled in the art has knowledge of the sequence of any of SEQ ID NO 1–9, or possession of a probe based on that sequence, which will specifically hybridize to the corresponding mRNA or cDNA or genomic DNA, that person can readily identify and obtain the corresponding full sequence coding for a polypeptide. Likewise, that person can obtain a cDNA and its sequence which corresponds to the full length of a specific mRNA, and subsequently obtain any of a large number of portions of that cDNA. By a related procedure, that person can also obtain the full length gene and its sequence by an appropriate procedure involving probing, cloning, and sequencing of genomic DNA. Such procedures are well-known and commonly used in the art.

As indicated above, the presence of a low level of sequencing errors (if any) in any of SEQ ID NO 1–9 creates no difficulties in those procedures, since a probe or primer based on one of the sequences of SEQ ID NO 1–9 will still specifically hybridize with the corresponding cDNA, genomic DNA, or mRNA under sufficiently stringent conditions, and can be used to help resequence the DNA to confirm the probe sequence or to discover any errors in the stated sequence.

As a result of the sequence relationships indicated above, a cDNA containing a full coding sequence, or a cDNA corresponding to the full length of a mRNA, is obtainable from a shorter, unique probe included in one of the above aspects. If the method for obtaining longer cDNA sequences is properly performed, such longer sequences are obtained with virtual certainty and the inclusion of the complete coding sequence or full-length cDNA can be routinely verified.

Therefore, such coding sequences and full length cDNAs are included in this invention. Of course, the full coding sequence or full-length cDNA is not limited to a specific method by which the sequence is obtained. Those skilled in the art will know that a variety of approaches and variations of methods will also provide essentially the same final product. Thus, this invention includes those DNA products, whatever the method used to obtain them.

It should be specifically noted that the above aspects include DNA molecules which each include a sequence of nucleotides which codes for a polypeptide which is a portion of a tyrosine kinase. However, the above aspect also includes shorter DNA molecules which may, for example, contain only a portion of a polypeptide-coding sequence.

Also, while the nucleic acid molecules of the above aspects can be obtained by standard cloning methods and amplified, such as by PCR, once the desired sequence is known, such molecules (especially DNA chains can also be chemically synthesized by routine methods to provide a specific sequence. This is particularly appropriate for sequences shorter than about 100 nucleotides. Once synthesized, such nucleic acid molecules can be used in the usual way as probes and primers.

Thus, from the above aspects, this invention provides nucleic acid molecules which can include full or partial coding sequences or cDNA sequences or mRNA sequences. It also provides nucleic acid molecules which can be used as probes or primers for locating, mapping, identifying, amplifying, and obtaining nucleotide sequences. It also provides probes and primers which can be used for detecting the overall or individual synthetic status of various cellular mRNA and for diagnosing cellular abnormalities due to disease. Similarly, the present invention also provides nucleic acid molecules, preferably DNA molecules, which can be used as probes or primers for detecting the overall or individual synthetic status of various corresponding cellular mRNA.

Use of the term "isolated" indicates that a naturally occurring material or organism (e.g., a DNA sequence) has been removed from its normal environment. Thus, an isolated DNA sequence has been removed from its usual cellular environment, and may, for example, be in a cell-free solution or placed in a different cellular environment. For a molecule, such as a DNA sequence, the term does not imply that the molecule (sequence) is the only molecule of that type present.

It is also advantageous for some purposes that an organism or molecule (e.g., a nucleotide sequence) be in purified form. The term "purified" does not require absolute purity; instead, it indicates that the sequence, organism, or molecule is relatively purer than in the natural environment. Thus, the claimed DNA could not be obtained directly from total human DNA or from total human RNA. The claimed DNA sequences are not naturally occurring, but rather are obtained via manipulation of a partially purified naturally occurring substance (genomic DNA clones). The construction of a genomic library from chromosomal DNA involves the creation of vectors with genomic DNA inserts and pure individual clones carrying such vectors can be isolated from the library by clonal selection of the cells carrying the library.

In the context of this disclosure, "human gene" should be understood to refer to an inheritable unit of genetic material found in a human chromosome. Each gene is composed of a linear chain of deoxyribonucleotides which can be referred to by the sequence of nucleotides forming the chain. Thus, "sequence" is used to indicate both the ordered listing of the nucleotides which form the chain, and the chain, itself, which has that sequence of nucleotides. ("Sequence" is used in the same way in referring to RNA chains, linear chains made of ribonucleotides.) The gene includes regulatory and control sequences, sequences which can be transcribed into an RNA molecule, and may contain sequences with unknown function. Some of the RNA products (products of transcription from DNA) are messenger RNAs (mRNAs) which initially include ribonucleotide sequences (or sequence) which are translated into a polypeptide and ribonucleotide sequences which are not translated. The sequences which are not translated include control sequences and may include some sequences with unknown function. The coding sequences of many mammalian genes are discontinuous, having coding sequences, exons, alternating with non-coding sequences, introns. The introns are present in the mRNA molecule as it is transcribed from the DNA, but the introns are removed and the exons spliced together to form mature mRNA. Thus, mature mRNA is mRNA which is suitable for translation, the introns have been removed and usually other modifications made. It should be recognized that small differences in nucleotide sequence for the same gene can exist between different persons, or between normal cells and cancerous cells, without altering the identity of the gene.

Thus, "expressed gene" means that, in the cell or tissue of interest, the gene is transcribed to form RNA molecules and the mature mRNA may be translated to form polypeptides. Expression includes transcription and translation of a nucleic acid. Which genes are expressed in a specific cell line or tissue will depend on factors such as tissue or cell type, stage of development of the cell, tissue, or individual, and whether the cells are normal or transformed into, for example, cancerous cells.

Reference to nucleic acid molecules or sequences which "corresponds" to each other, or to a "correspondence" between a polypeptide and a nucleic acid, the correspondence is shown by a transcriptional and/or translational, or reverse transcriptional relationship. As indicated above, many genes can be transcribed to form mRNA molecules. Therefore, there is a correspondence between the DNA sequence of the gene and the mRNA which is, or might be, transcribed from that gene; the correspondence is also present for the reverse relationship, the messenger RNA corresponds with the DNA of the gene. This correspondence is not limited to the relationship between the full sequence of the gene and the full sequence of the mRNA, rather it also exists between a portion or portions of the DNA sequence of the gene and a portion or portions of the RNA sequence of the mRNA. Specifically it should be noted that this correspondence is present between a portion or portions of an mRNA which is not normally translated into polypeptide and all or a portion of the DNA sequence of the gene.

Similarly, the correspondence exists between a messenger RNA and a single-strand DNA which is or can be obtained from the mRNA by reverse transcription using a reverse transcriptase. As just described above, the correspondence exists between all or a portion of the DNA and all or a portion of the messenger RNA. Likewise, the correspondence exists between all or a portion of the messenger RNA and all or a portion of a DNA strand which has a sequence complementary to the sequence of the DNA obtained by reverse transcription. Further, the correspondence is present between all or a portion of the messenger RNA and all or a portion of a double-stranded DNA comprising the DNA obtained by reverse transcription and its complementary strand.

Similarly, the DNA of a gene or of cDNA, or the RNA of a mRNA "corresponds" to the polypeptide encoded by that gene and mRNA and cDNA. This correspondence between the mRNA and the polypeptide is established through the translational relationship; the nucleotide sequence of the mRNA is translated into the amino acid sequence of the polypeptide. Then, due to the transcription or reverse transcription relationship between the DNA of the gene or the cDNA and the mRNA, there is a "correspondence" between the DNA and the polypeptide. Such a term includes nucleic acid which is analogous or homologous to a reference nucleic acid, as well as complementary nucleic acid.

References to a "portion" of a DNA or RNA chain mean a linear chain which has a nucleotide sequence which is the same as a sequential subset of the sequence of the chain to which the portion refers. (Reference to a portion of a polypeptide chain and an amino acid sequence has similar meaning.) Such a subset may contain all of the sequence of the primary chain or may contain only a shorter sequence. The subset will contain at least 13–25, 50, or 100 bases in a single strand, but preferably will contain the full coding sequence from the corresponding mRNA.

However, by "same" is meant to include deletions, additions, or substitutions of specific nucleotides of the sequence, or a combination of these changes, which affect a small percentage of the full sequence and still leave the sequences substantially the same. Preferably this percentage of change will be less than 10%, more preferably less than 5%, still more preferably less than 3%, and most preferably less than 1%. Such changes do not affect the property of the protein coded by the sequence. "Same" is therefore distinguished from "identical"; for identical sequences there cannot be any difference in nucleotide sequences. An example of sequences that can be said to be the "same" is sequences encoding homologous proteins from different species which have some similarity in function and have highly similar but not exactly identical sequences.

As used above, "complementary" has its usual meaning from molecular biology. Two nucleotide sequences or strands are complementary if they have sequences which would allow base pairing (Watson-Crick or Hoogstein) according to the usual pairing rules. This does not require that the strands would necessarily base pair at every nucleotide; two sequences can still be complementary with a low level (e.g., 1–3%) of base mismatch such as that created by deletion, addition, or substitution of one or a few (e.g., up to 5 in a linear chain of 25 bases) nucleotides, or a combination of such changes. Preferably, however, complementary sequences are exactly complementary, meaning that base pairing can occur for each base of a particular sequence in a chain.

In another aspect, the invention provides an isolated or purified nucleic acid molecule encoding a polypeptide expressed in a tissue, obtainable by hybridization under stringent hybridization conditions of a nucleotide sequence selected from the group consisting of SEQ ID NO. 1–9 or a sequence complementary thereto, to a mRNA from that tissue.

In a further aspect, the invention provides a recombinant nucleic acid molecule having a transcription initiation region functional in a cell, transcriptionally linked with a sequence complementary to an RNA sequence encoding all or at least 25 contiguous amino acids a tyrosine kinase , and a transcription termination region functional in a cell. The tyrosine kinase is encoded by a gene corresponding to any of SEQ ID NO. 1–9.

In addition, it is often advantageous to insert DNA sequences into any of a variety of vectors. Therefore, in further aspects this invention provides DNA of any of the above aspects in a vector. The vector may be selected for a number of different purposes, which can include to produce more DNA with the sequence of the vector insert, but can also specifically include means to translate mRNA transcribed from the vector insert into a polypeptide product, i.e., an expression vector. DNA inserted into an expression vector preferably contains at least 60% of the coding region of the corresponding full-length cDNA, more preferably at least 75%, still more preferably at least 90%, and most preferably all of the coding sequence of the corresponding full-length cDNA.

Further, since vectors are usually used by inserting the vector into a cell, these aspects also include a cell containing a vector which has the DNA of any of the above aspects inserted. Within such a cell, the vector may exist extrachromosomally (e.g., as a plasmid or minichromosome), or the vector or part of the vector may be integrated into the host cell chromosome.

In this application a "vector" is an agent into which DNA of this invention can be inserted by incorporation into the DNA of the agent. Thus, examples of classes of vectors can be plasmids, cosmids, and viruses (e.g., bacteriophage). Typically, the agents are used to transmit the DNA of the invention into a host cell (e.g., bacterium, yeast, higher eukaryotic cell). A vector may be chosen based on the size of the insert desired, as well as based on the intended use. For preservation of a specific DNA sequence (e.g., in a cDNA library) or for producing a large number of copies of the specific DNA sequence, a cloning vector would be chosen. For transcription of RNA or translation to produce an encoded polypeptide, an expression vector would be chosen. Following transfection of a cell, all or part of the vector DNA, including the insert DNA, may be incorporated into the host cell chromosome, or the vector may be maintained extrachromosomally.

In another aspect, the invention concerns an isolated, enriched, or purified kinase polypeptide, where the tyrosine kinase is encoded by a gene corresponding to any of SEQ ID NO. 1–9 (see FIGS. 4A–C). The polypeptide preferably contains at least 25 contiguous amino acids of the amino acid sequence of the tyrosine kinase, more preferably at least 50 amino acids, still more preferably at least 100 amino acids. Most preferably, the polypeptide includes an amino acid sequence which is sufficiently duplicative of the amino acid sequence of the native kinase as to have similar biological activity as the native molecule; this includes a polypeptide which has the full amino acid sequence of the native molecule.

Since the disclosed sequence identifies and provides the full coding sequence of each of the corresponding tyrosine kinase genes, this also provides the amino acid sequence of the encoded polypeptide due to the known genetic code such as are shown in SEQ. ID. No. 10–SEQ. ID. NO. 18 (FIGS. 7A–C). Also, possession of a nucleic acid which contains all or part of a full coding sequence enables the production of antibodies which recognize an epitope on the native tyrosine kinase polypeptide.

Therefore, in a further aspect the invention provides an antibody having specific binding affinity to a tyrosine kinase polypeptide of SEQ ID NO. 10–SEQ ID NO. 18. Including both polyclonal and monoclonal antibodies For most uses, it is beneficial if the antibody is purified or isolated. Further, it is often beneficial to produce antibodies in cell culture (i.e., monoclonal antibodies). Therefore, the invention also provides a hybridoma producing such an antibody.

In addition, the invention provides testing and screening methods to identify and analyze compounds which bind to and/or affect the activity of kinase polypeptides, such as polypeptides encoded by the kinase genes identified herein.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. Use of the term "comprising" in connection with an embodiment of the invention should be understood to include embodiments "consisting of" or "consisting essentially of" the specified elements; similarly "consisting essentially of" includes "consisting of".

Other features and advantages of the invention will be apparent from the following detailed description of the preferred embodiments and from the claims.

BRIEF DESCRIPTION OF THE DRAWINGS

FIG. 1A and 1B show the alignment and comparison of the amino acid sequences of the human LMR1, LMR2 and LMR 3 (SEQ ID. NO. 11, 14, 18)

FIG. 2 shows the identification and sequences of the oligonucleotides used as primers.

FIGS. 3A and 3B show expression profiles (Northern blot) of Human normal tissue vs. tumor for LMR1, LMR2 and LMR3.

FIG. 4 provides the expression analysis (in situ) in rat embryos for LMR1, LMR2 and LMR3.

FIG. 5 provides the expression analysis (in situ) in adult rat brain for LMR1, LMR2 and LMR3.

FIGS. 6A, 6B, 6C, 6D, 6E, 6F, 6G, 6h, 6I provide nucleotide sequences of LMRs for; LMR1_r (rat), LMR1_h (human), LMR1_m (mouse), LMR2_r (rat), LMR2_h (human), LMR2_m (mouse), LMR3_r (rat), LMR3_h (human), and LMR3_m (mouse).

FIG. 7A, 7B and 7C Provide amino acid sequences of LMRs for; LMR1_r (rat), LMR1_h (human), LMR1_m (mouse), LMR2_r (rat), LMR2_h (human), LMR2_m (mouse), LMR3_r (rat), LMR3_h (human), and LMR3_m (mouse).

DESCRIPTION OF THE PREFERRED EMBODIMENTS

The present invention relates to mammalian nucleic acids encoding polypeptides having tyrosine kinase activity, the polypeptides encoded by those nucleic acids, cells, tissues and animals containing such nucleic acids, antibodies to such polypeptides, assays utilizing such polypeptides, and methods relating to all of the foregoing.

I. Cloning, Probing, and Sequencing

In general, as indicated above, the nucleic acids of this invention encode mammalian tyrosine kinases which have sequences characteristic of components of signal transduction pathways. Such nucleic acid sequences can be identified in a number of different ways, including by analyzing sequenced, but unidentified, DNA or RNA or polypeptide sequences from public databases, by probing DNA libraries (e.g., cDNA and genomic libraries) using degenerate probes to sequences conserved in various families and sub-families of such kinases or by PCR-based cloning using degenerate primers based on conserved sequences for various families and sub-families. For the probing or PCR-based approaches, once one or more clones are identified having sequences corresponding to the probe or primers, the genomic or cDNA insert in that clone can be at least partially sequenced by routine methods to confirm that the clone sequence actually corresponds to a tyrosine kinase, and to provide a unique sequence identifying the full gene. Possession of such a unique sequence provides the full gene sequence by following routine techniques. For example, an appropriate probe sequence can be selected and synthesized. The probe can be used to probe cDNA or genomic libraries under stringent hybridization conditions to identify a clone(s) which contain a sequence which contains the complete corresponding open reading frame.

Likewise, a probe sequence based on a specific homologous tyrosine kinase sequence from a different mammalian species can be used to detect the corresponding human version of that gene. For example, a probe complementary to a rat gene was used to identify a homologous human kinase sequence as is described in the Example section below. This probe allowed hybridization under sufficiently stringent conditions to a homologous 5' sequence of the clone identified as LMR1.

The demonstrated sequence homology over the human, rat, and mouse homologs of the identified genes demonstrates that the invention also provides the other mammalian homologs by routine methods. For example, probe sequences can be obtained based on the genes described herein, preferably from regions of high sequence conservation. Using such probes, and if necessary further degenerate probes, the corresponding genes in other mammalian species can be readily obtained. A homologous gene from a cow has been obtained.

II. Gene Identification

As indicated above, the tyrosine kinase encoding genes of the present invention are initially identified as having nucleotide sequences characteristic of particular classes of such enzymes, or having sequences corresponding to previously identified homologous genes from one or more other mammalian species. Thus, the genes of the present invention and the corresponding expression products are distinguished and characterized as tyrosine kinases by the sequence relationships with previously known genes or proteins. Such sequence comparisons can be routinely performed using readily available computer-based sequence analysis programs. Such analysis will not generally require full nucleotide or amino acid sequences for an enzyme, as a partial sequence will provide sufficient information to characterize and classify the gene and gene product.

Therefore, the identification method described herein allows novel kinase genes to be distinguished from cloned nucleotide sequences, such as in cDNA libraries, as well as from sequence database information of sequenced, but not functionally identified gene sequences.

III. Construction of Probes and Primers

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (see, e.g., "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "A Guide to Methods and Applications", edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (see, e.g., "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Probe Based Method and Kit for Detecting a Disclosed Kinase Gene

One method of detecting the presence of one of the disclosed genes in a sample involves (a) contacting a sample with a nucleic acid probe as described above, under conditions such that hybridization occurs, and (b) detecting the presence of the probe bound to the nucleic acid molecule. One skilled in the art would select the nucleic acid probe according to techniques known in the art as described above. Samples to be tested include but should not be limited to RNA samples of human tissue.

A kit for detecting the presence of one of the disclosed genes in a sample includes at least one container means containing the above-described nucleic acid probe. The kit may further include other containers containing one or more of the following: wash reagents and reagents capable of detecting the presence of bound nucleic acid probe. Examples of detection reagents include, but are not limited to radiolabeled probes, enzymatic labeled probes (horseradish peroxidase, alkaline phosphatase), and affinity labeled probes (biotin, avidin, or streptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

V. Obtaining Full Length Gene Sequences

By utilizing methods well-known to those skilled in the art and portions of the sequences identified in this invention, full length gene sequences can be readily obtained. Such full-length sequence can be complementary DNA (cDNA) sequences or genomic sequences.

Probes can be selected according to the usual considerations to provide specific detection of clones containing long DNA inserts. Preferably at least one probe is obtained which binds to a sequence at or near either the 5' or 3' end of the coding sequence. In the case of cDNA clones in a cDNA library, the library vectors can be selected such that vector sequences adjacent to the insert can be utilized as PCR primers, allowing direct amplification and convenient sequencing of the insert by common methods. This process will often provide a full coding sequence, though in some cases it may be necessary to construct a full-length coding sequence using two or more overlapping clones.

Similarly, a full genomic sequence can be obtained using a genomic library. However, in this case it will often be necessary to construct a full length sequence based on overlapping clone sequences due to the length added by the introns present in most human genes.

VI. Expression Patterns

Many human genes are expressed at different levels in different tissues. In some cases, a gene-is not expressed at all in some cells or tissues, and at high levels in others. Thus, a variety of different human cell lines from various tissue sources, as well as several different normal human tissues were analyzed for the expression levels of the tyrosine kinase genes identified in this invention. In general, the expression level of a gene was determined by determination of the amount of the corresponding messenger RNA (mRNA) present in the cells, based on hybridization with a labeled probed under specific hybridization conditions.

The results of such analyses are discussed in the Example section below. These expression levels suggest the types of diseases and conditions which can be affected by modulation of the activity level of one of the disclosed tyrosine kinases in accord with the understanding of the functions of such specific enzymes. As discussed below, three of the tyrosine kinases of the invention are expressed to some level in tissues of neuronal origin. One, LMR2, is not expressed in normal tissues but is expressed in a variety of cancer tissues. LMR2 is also highly expressed in lung and ovarian tumor samples, suggesting this RTK may play a role in the proliferation of these cancers.

VII. Nucleic Acid Sequence Variants

Included within the scope of this invention are the functional equivalents of the isolated nucleic acid molecules described herein. The degeneracy of the genetic code permits substitution of certain codons by other codons which specify the same amino acid and hence would give rise to the same protein. The nucleic acid sequence can vary substantially, since, with the exception of methionine and tryptophan, the known amino acids can be coded for by more than one codon. Thus, portions or all of any of the genes disclosed could be synthesized to give a nucleic acid sequence significantly different from that shown in any of SEQ ID NO. 1–9. The encoded amino acid sequence would, however, be preserved.

In addition, the nucleic acid sequence may comprise a nucleotide sequence which results from the addition, deletion or substitution of at least one nucleotide to the 5'-end and/or the 3'-end of one of the nucleic acid sequences shown, or a derivative thereof. Any nucleotide or polynucleotide may be used in this regard, provided that its addition, deletion or substitution does not alter the amino acid sequence of a polypeptide which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the disclosed nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the disclosed genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

VIII. DNA Constructs Comprising a Nucleic Acid Molecule and Cells Containing These Constructs.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecule. The present invention also relates to a nucleic acid molecule comprising a transcriptional region functional in a cell, a sequence complimentary to an mRNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the coding sequence of any of the disclosed genes may be obtained by the above-described methods. This region may be retained for its transcriptional termination regulatory sequences, such as termination and polyadenylation. Thus, by retaining the 3'-region naturally contiguous to the DNA sequence encoding one of the disclosed genes, the transcriptional termination signals may be provided. Where the transcriptional termination signals are not satisfactorily functional in the expression host cell, then a 3' region functional in the host cell may be substituted.

Two DNA sequences (such as a promoter region sequence and a coding sequence) are said to be operably linked if the nature of the linkage between the two DNA sequences does not (1) result in the introduction of a frame-shift mutation, (2) interfere with the ability of the promoter region sequence to direct the transcription of a gene sequence, or (3) interfere with the ability of the a gene sequence to be transcribed by the promoter region sequence. Thus, a promoter region would be operably linked to a DNA sequence if the promoter were capable of effecting transcription of that DNA sequence. Thus, to express one of the disclosed genes, transcriptional and translational signals recognized by an appropriate host are necessary.

The present invention encompasses the expression of one of the disclosed genes (or a functional derivative thereof) in either prokaryotic or eukaryotic cells. Prokaryotic hosts are, generally, very efficient and convenient for the production of recombinant proteins and are, therefore, one type of preferred expression system for one of the disclosed genes. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include lambda gt10, lambda gt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express one of the disclosed genes (or a functional derivative thereof) in a prokaryotic cell, the coding sequence is operably linked to a functional prokaryotic promoter. Such promoters may be either constitutive or, more preferably, regulatable (i.e., inducible or derepressible). Examples of constitutive promoters include the int promoter of bacteriophage lambda, the bla promoter of the beta-lactamase gene sequence of pBR322, and the CAT promoter of the chloramphenicol acetyl transferase gene sequence of pPR325, and the like. Examples of inducible prokaryotic promoters include the major right and left promoters of bacteriophage lambda (PL and PR), the trp, recA, beta lacZ, lacI, and gal promoters of *E. coli*, the beta-amylase (Ulmanen et at., *J. Bacteriol.* 162:176–182(1985)) and the (−28-specific promoters of *B. subtilis* (Gilman et at., *Gene Sequence* 32:11–20(1984)), the promoters of the bacteriophages of Bacillus (Gryczan, In: The Molecular Biology of the Bacilli, Academic Press, Inc., N.Y. (1982)), and Streptomyces promoters (Ward et at., *Mol. Gen. Genet.* 203:468–478 (1986)). Prokaryotic promoters are reviewed by Glick (*J. Ind. Microbiot.* 1:277–282(1987)); Cenatiempo (*Biochimie* 68:505–516(1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et at. (*Ann. Rev. Microbiol.* 35:365–404(1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459(1988). Alternatively, baculovirus vectors can be engineered to express large amounts of one of the genes of interest in insect cells (Jasny, *Science* 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes which are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of one of the disclosed genes.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of one of the disclosed genes in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288(1982)); the TK promoter of Herpes virus (McKnight, *Cell* 31:355–365 (1982)); the SV40 early promoter (Benoist et al., *Nature* (*London*) 290:304–310(1981)); the yeast gal4 gene sequence promoter (Johnston et al., *Proc. Natl. Acad. Sci.* (*USA*) 79:6971–6975 (1982); Silver et al., *Proc. Natl. Acad. Sci.* (*USA*) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes a kinase (or a functional derivative thereof) does not contain any intervening codons which are capable of encoding a methionine (i.e., AUG). The presence of such codons results either in a formation of a fusion protein (if the AUG codon is in the same reading frame as the coding sequence) or a frame-shift mutation (if the AUG codon is not in the same reading frame as the coding sequence).

A nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColEl, pSC101, pACYC 184, "VX. Such plasmids are, for example, disclosed by Sambrook (see, e.g., "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, N.Y. (1982), pp. 307–329). Suitable Streptomyces plasmids include plJ101 (Kendall et al., *J. Bacteriol.* 169:4177–4183 (1987)), and streptomyces bacteriophages such as C31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704(1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274(1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204 (1982); Bollon et at., *J. Ctin. Hematol. Oncol.* 10:39–48 (1980); Maniatis, In: Cell Biology: A Comprehensive Treatise, Vol. 3, Gene Sequence Expression, Academic Press, N.Y., pp. 563–608(1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of the encoded amino acid sequence. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

IX. Purified Polypeptides

A variety of methodologies known in the art can be utilized to obtain the peptide of the present invention. The peptide may be purified from tissues or cells which naturally produce the peptide. Alternatively, the above-described isolated nucleic acid fragments could be used to express the kinase protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

X. An Antibody Having Binding Affinity to a Kinase Polypeptide and a Hybridoma Containing the Antibody.

The present invention relates to an antibody having binding affinity to one of the identified tyrosine kinase polypeptide. The polypeptide may have the amino acid sequence shown in SEQ ID NO. 10–SEQ ID NO. 18, or functional derivative thereof, or at least 9 contiguous amino acids thereof (preferably, at least 20, 30, 35, or 40 contiguous amino acids thereof).

The present invention also relates to an antibody having specific binding affinity to a polypeptide encoded by one of the disclosed genes. Such an antibody may be isolated by comparing its binding affinity to a particular encoded polypeptide with its binding affinity to another polypeptide. Those which bind selectively to the particular encoded polypeptide would be chosen for use in methods requiring a distinction between that particular polypeptide and other polypeptides. Such methods could include, but should not be limited to, the analysis of altered expression of the particular polypeptide in tissue containing other polypeptides.

The tyrosine kinase proteins of the present invention can be used in a variety of procedures and methods, such as for the generation of antibodies, for use in identifying pharmaceutical compositions, and for studying DNA/protein interaction.

The peptides of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized. forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., *J. Immunol. Methods* 35:1–21(1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass is determined using procedures known in the art (Campbell, "Monoclonal Antibody Technology: Laboratory Techniques in Biochemistry and Molecular Biology", supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Immumnol.* 109:129(1972); Goding, *J. Immunol. Meth.* 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter (1986); Jacoby et al., *Meth. Enzym.* 34, Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, N.Y., pp. 289–307 (1992), and Kaspczak et al., *Biochemistry* 28:9230–8(1989).

Anti-peptide peptides can be generated by replacing the basic amino acid residues found in a peptide sequence encoded by one of the disclosed genes with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

XI. An Antibody Based Method and Kit

The present invention encompasses a method of detecting a polypeptide encoded by one of the disclosed genes in a sample, by: (a) contacting the sample with an above-described antibody, under conditions such that immunocomplexes form, and (b) detecting the presence of said antibody bound to the polypeptide. In detail, the methods involves incubating a test sample with one or more of the antibodies of the present invention and assaying whether the antibody binds to the test sample. Altered levels of a kinase in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, FL Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

XII. Isolation of Compounds which Interact with Identified RTKs.

The present invention also relates to a method of detecting a compound capable of binding to a RTK polypeptide from one of the identified kinase genes by incubating the compound with the polypeptide and detecting the presence of the compound bound to the polypeptide. The compound may be present within a complex mixture, for example, serum, body fluid, or cell extracts. Binding assay methods may have a variety of different formats, including competition binding assays in which the effect of the presence of a test compound or compound mixture on the binding of a labeled known binding compound is determined. Other formats include detection of receptor activation, detection of binding of labeled or spectrophotometrically detectable test compound to the kinase. Depending on whether a particular kinase is naturally membrane bound or free in the cytoplasm, the binding assays can be performed with isolated membranes, with intact cells, or in a cell and membrane-free solution or attached to a solid support. Additionally, membrane-bound kinases can often be freed from the membrane, such as by removing a transmembrane portion, and assayed for binding in solution or attached to a solid support.

The present invention also relates to a method of detecting an agonist or antagonist of RTK activity or RTK binding partner activity by incubating cells that produce a particular RTK in the presence of a compound and detecting changes in the level of activity of the particular RTK or RTK binding partner activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing activity associated with particular RTKs in a mammal by administering to a mammal an agonist or antagonist to the particular RTK(s) in an amount sufficient to effect the agonism or antagonism. A method of treating diseases in a mammal with an agonist or antagonist of activity related to a particular RTK(s) by administering the agonist or antagonist to a mammal in an amount sufficient to agonize or antagonize RTK associated functions is also encompassed in the present application.

XIII. Transgenic Animals.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., Proc. Nat. Acad. Sci. USA 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, Experientia 47: 897–905 (1991). Other procedures for introduction of DNA into tissues of animals are described in U.S. Pat. No., 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., Cell 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, Teratocarcinomas and Embryonic Stem Cells, A Practical Approach, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, Science 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., Nature 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

Thus, the invention provides transgenic, nonhuman mammals containing a transgene encoding a polypeptide encoded by one of the disclosed genes, or a gene effecting the expression of a such a polypeptide. Such transgenic nonhuman mammals are particularly useful as an in vivo test system for studying the effects of introducing such a polypeptide, regulating the expression of such a polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human polypeptide encoded by one of the disclosed genes. Native expression in an animal may be reduced by providing an amount of anti-sense RNA or DNA effective to reduce expression of the receptor.

XIV. Gene Therapy

Genetic sequences corresponding to the disclosed genes will also be useful in gene therapy (reviewed in Miller, *Nature* 357:455–460, (1992). Miller states that advances have resulted in practical approaches to human gene therapy that have demonstrated positive initial results. The basic science of gene therapy is described in Mulligan, *Science* 260:926–931, (1993).

In one preferred embodiment, an expression vector containing a coding sequence of one of the disclosed genes is inserted into cells, the cells are grown in vitro and then infused in large numbers into patients. In another preferred embodiment, a DNA segment containing a promoter of choice (for example a strong promoter) is transferred into cells containing an endogenous copy of one of the disclosed genes in such a manner that the promoter segment enhances expression of the endogenous gene (for example, the promoter segment is transferred to the cell such that it becomes directly linked to the endogenous gene).

The gene therapy may involve the use of an adenovirus containing cDNA corresponding to one of the disclosed genes targeted to a tumor, systemic increase of expression of one of the disclosed genes by implantation of engineered cells, injection with virus having a recombinant form of one of the disclosed genes, or injection of naked DNA of one of the disclosed genes into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g.,cDNA) encoding recombinant protein into the targeted cell population (e.g., tumor cells). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi MR, *Cell* 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with CaPO4 and taken into cells by pinocytosis (Chen C. and Okayama H, *Mol. Cell Biol.* 7:2745–52 (1987)); electroporation, wherein cells are exposed to large voltage pulses to introduce holes into the membrane (Chu G. et al., *Nucleic Acids Res.*, 15:1311–26 (1987)); lipofection/liposome fusion, wherein DNA is packaged into lipophilic vesicles which fuse with a target cell (Felgner PL., et al., *Proc. Natl. Acad. Sci. USA*. 84:7413–7 (1987)); and particle bombardment using DNA bound to small projectiles (Yang NS. et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel DT et al., *Am. J. Respir. Cell. Mol. Biol.*, 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences of one of the disclosed genes is provided, in which the nucleic acid sequence is expressed only in specific tissue. Methods of achieving tissue-specific gene expression are set forth, for example, in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

EXAMPLES

The examples below are non-limiting and are merely representative of various aspects and features of the present invention. The examples below demonstrate the isolation, and characterization of the gene sequences corresponding to a group of novel, related tyrosine kinases.

Example 1

Isolation of cDNAs Encoding Three Novel Human RTKs

Protein kinases are one of the largest families of eukaryotic protiens with several hundred known members. These proteins share a 250–300 amino acid domain that can be subdivided into 12 distinct subdomains that comprise the common catalytic core structure. These conserved protein motifs have recently been exploited using PCR-based cloning strategies leading to a significant expansion of the known kinases. Multiple alignment of the sequences in the catalytic domain of protein kinases and subsequent phylogentic analysis permits their segregation into a phylogentic tree. In this manner, related kinases are clustered into distinct branches or subfamilies including: tyrosine kinases, cyclic-nucleotide-dependent kinases, calcium/calmodulin kinases, cyclin-dependent kinases and MAP-kinases, as well as several other less defined subfamilies.

Initially we set out to identify homologues of TRK, a receptor that represents a distinct family of tyrosine kinases. We designed degenerate primers to conserved sequences within kinase subdomains I and VIII of this family of three mammalian receptors. Subdomain I is at the N-terminus of the kinase domain and contains the consensus motif GXGXXGXV which is involved in anchoring ATP to the catalytic unit of all classes of kinases. Subdomain VIII contains a highly conserved APE motif, upstream of which are residues that are well conserved between members of the same class of kinases (serine kinases, cytoplasmic tyrosine kinases, or receptor tyrosine kinases). Based on comparison of all known protein kinases, we designed degenerate oligonucleotide primers to subdomains I and VIII that would pick up only the three TRK kinases.

MATERIALS AND METHODS

Cells Lines and Culture Conditions

All cell lines were obtained from the American Type Culture Collection (ATCC) or from the NCI and were grown according to their recommendations.

Molecular Cloning

Total RNAs were isolated using the Guanidine Salts/Phenol extraction protocol of Chomczynski and Sacchi (P. Chomczynski and N. Sacchi, Anal. Biochem. 162, 156 (1987) from human, rat or mouse tissues, and from human tumor cell lines originating from specific tissue types. These RNAs were used as templates to generate single-stranded cDNAs using the Superscript Preamplification System for First Strand Synthesis kit purchased from GibcoBRL (Life Technologies, U.S.A.; Gerard, GF et al. (1989), FOCUS 11, 66) under conditions recommended by manufacturer. A typical reaction used 10 ug total RNA or 2 ug poly(A)$^+$ RNA with 1.5 ug oligo(dT)$_{12-18}$ in a reaction volume of 60 ul. The product was treated with RNaseH and diluted to 100 ul with H$_2$O. For subsequent PCR amplification, 1–4 ul of these sscDNAs were used in each reaction.

Oligonucleotides were synthesized on an Applied Biosystems 394 DNA synthesizer using established phosphoramidite chemistry and were used unpurified after precipitation with ethanol. The degenerate oligonucleotide primers are listed in Table I. Also listed for each degenerate oligonucleotide is the length, orientation, nucleotide sequence, and the amino acid sequence to which the primer is derived. Degenerate nucleotide residue designations are: N=A, C, G,or T; R=A or G; and Y=C or T. Using TRK as a template, these primers produce products of 550 bp.

A PCR reaction was performed using Primers TRKa and TRKb applied to several of the single-stranded sources listed above. The primers were added at a final concentration of 5 uM each to a mixture containing 10 mM Tris HCl (pH8.3), 50 mM KCl, 1.5 mM MgCl$_2$, 200 uM each deoxynucleoside triphosphate, 0.001% gelatin, and 1.5 U AmpliTaq DNA Polymerase (Perkin-Elmer/Cetus), and 1–4 ul cDNA. Following 3 min denaturation at 95° C., the cycling conditions were 94° C. for 30 s, 50° C. for 1 min, and 72° C. for 1min 45 s for 35 cycles. PCR fragments migrating at between 450–550 bp were isolated from 2% agaorse gels using GeneClean, blunt cloned into pBlueScript SKII+ at the EcoRV site (Stratagene). Colonies were selected for mini plasmid DNA-preparations using Qiagen columns and the plasmid DNAs were sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., J. Mol. Biol.215:403–10).

A novel clone (#135-31-2) was isolated by PCR with primers TRKa and TRKb on single-stranded cDNA from rat adult brain substantia nigra as a template. This clone was subsequently designated as a fragment of rat LMR1.

A rat PC12 cDNA library in pCDNA (Clontech) and a rat fetal brain lambda gt11 cDNA library (Clontech) were screened with this fragment as a probe, leading to isolation of several larger cDNA clones. DNA sequence analysis of LMR1_r demonstrated its homology to several tyrosine kinase receptors, and it had all the motifs characteristic of this class of enzymes. The 5' end of this sequence encodes two hydrophobic regions, consistent with the presence of the signal sequence and transmembrane domain of a Type Ia transmembrane protein. The region between these two hydrophobic domains is only 18 amino acids, suggesting this protein contains an extremely short extracellular domain.

LMR1_r has several atypical amino acid substitutions at highly conserved sites in the putative tyrosine kinase domain. These include a VAVK to VVVK change in domain II, a DFG to DYG change in domain VII, and a SDVW to SNVW change in domain IX. We designed several additional primers to some of the unique motifs of LMR1_r to combine with other primers specific to the unrelated receptor tyrosine kinases TEK and ROS. The primer sequences are shown in FIG. 2. Multiple combinations of these primers were applied to single stranded cDNA from several rat, mouse, and human sources, leading to the isolation of additional homologues of LMR1.

Northern Blot Analysis

Northern blots were prepared by running 10 ug total RNA isolated from 60 human tumor cell lines and 26 normal human tissues on a denaturing formaldehyde 1.2% agarose gel and transferring to nylon membranes. Filters were hybridized with random prime [$\alpha^{32}$P]dCTP-labeled probes synthesized from the inserts of human LMR1, LMR2 and LMR3. Hybridization was performed at 42° C. overnight in 6×SSC, 0.1% SDS, 1×Denhardt's solution, 100 µg/ml denatured herring sperm DNA with 1–2×10$^6$ cpm/ml of $^{32}$P-labeled DNA probes. The filters were washed in 0.1×SSC/0.1% SDS, 65° C., and exposed on a Molecular Dynamics phosphorimager.

Semi-Ouantitative PCR Detection of LMR1

RNA was isolated from a variety of rat cell lines and fresh frozen tissues. Single stranded cDNA was synthesized from 10 µg of each RNA as described above using the Superscript Preamplification System (GibcoBRL). These single strand templates were then used in a 25 cycle PCR reaction with two LMR1_r specific oligonucleotides. 5'-TGAAAGTGGGAGATTACGGAATA and 5'-GTTACTATACTTAGTCTGATCTGC. Reaction products were electrophoresed on 2% agarose gels, stained with ethidium bromide and photographed on a UV light box. The relative intensity of the LMR1-specific bands were estimated for each sample.

In Situ Hybridization Analysis

Cryostat sections of OCT-embedded frozen rat embryos (E16, E20), and adult rat brain were placed on poly-lysine coated slides and fixed in 4% paraformaldehyde in PBS at 4° C. The slides were treated with 0.25% acetic anhydride/0.1M TEA for 10 min at room temperature, rinsed in 2×SSC and dehydrated by rinsing for 15 seconds each in water, followed by 30%, 50%, 85%, 95% and 100% EtOH. The slides were then air dried and prehybridized by transfering to PBS/5 mM MgCl2 for 10 min followed by 0.25M Tris/0.1M glycine for 10 min, and 50% formamide/2×SET at 37° C. for 10 min. The slides were then hybridized in hybridization buffer (50% formamide/2×SET/10× Denhardt's/0.5 mg per ml tRNA/100 mM DTT) containing 2 million cpm of [35S]CTP-labeled sense and antisense riboprobes generated from 300–500 bp fragments encoding rat LMR1, LMR2, or LMR3. Six drops of the hybridization mix was added per slide and incubated for 4 hours at 45° C. The slides were rinsed in 4×SSC followed by 50% formamide/2×SET for 15 min at 6° C. The slides were again rinsed in 4×SSC prior to treating with 20 ug/ml RNAase A in 4×SET at 37° C. for 20 min and then rinsed in 1×SSC. The slides were then dehydrated in 30% EtOH/0.3 M NH4HOAc, 50% EtOH/0.3 M NH4HOAc, 70% EtOH/0.3 M NH4HOAc, 85% EtOH, 95% EtOH, 100% EtOH, air dried, and stored in an airtight box with dessicant at room temperature. Slides were dipped in Kodak NTB2 emulsion, and exposed for 2–5 weeks prior to developing.

Chromosomal Localization and Genomic Cloning of LMR2

A pair of oligonucleotides primers were derived from the sequence of the 3'-untranslated region of human LMR2 for amplification of a 521 bp LMR2 specific fragment from genomic DNA. The primers span nucleotides 8232–8254 (sense) and 8732–8752 (antisense) of the human LMR2 sequence. This primer pair was applied to the Stanford Human Genome Center G3 radiation hybrid panel (Research Genetics, Huntsville, Ala.) and to a library of human bacterial artifical chromosome (BAC) DNA pools (Release III, Research Genetics, Huntsville, AL). PCR reactions were performed with a 64° C. annealing temperature for 30–35 cycles as recommended by the distributor. In addition, a 158 bp XhoI-PstI fragment from the 5' end of human LMR2 was used to probe a human placenta genomic DNA library in lambda FIXII in order to isolate a genomic clone spanning the 5' end of the LMR2 cDNA clones.

RESULTS

Seouence Analysis OF cDNA Clones Encoding Three Novel RTKs

We designed degenerate primers TRKa and TRKb based on conserved residues within the kinase domain of the receptor tyrosine kinase TRK, to use for identification of novel kinases using polymerase chain reaction (PCR). When applied to rat substantia nigra sscDNA as a template, multiple copies of TRKA, TRKB and TRKC cDNA were isolated as well as a several novel DNA fragments with homology to serine kinases. A novel 550 bp clone (135-31-2) had sequence that was most similar to the RTKs, Insulin receptor, IGF1-receptor, TRKA, and ROS was named LMR1_r.

Using this fragment as a probe, we screened RNAs from a number rat sources by Northern blot, demonstrating an apparent selectivity in expression of this clone in rat brain. The LMR1_r probe was also used to screen a cDNA library constructed from rat PC12 cell line RNA to isolate overlapping clones spanning the 3'-end of LMR1_r.

The 2,572 bp LMR1_r nucleotide sequence (SEQ ID NO. 1) is shown in FIG. 7 and contains a single open reading frame encoding a polypeptide of 848 amino acids. Additional 3' clones will be required to resolve the complete sequence of LMR1_r, however the C-terminal portion of LMR1 was subsequently isolated from a human cDNA library (see below).

LMR1_r amino acid sequence (SEQ ID NO. 10) conserves all 12 subdomains characteristic of eukaryotic protein kinases. It does have atypical substititions in three highly conserved residues within the catalytic domain of other protein kinases, as described below. Upstream of the putative protein kinase domain are two hydrophobic stretches characteristic of a signal sequence and transmembrane domain.

We designed several additional primers to some of the unique motfis of LMR1_r to combine with other primers specific to the unrelated receptor tyrosine kinases TEK and ROS. The primer sequences are shown in Table I. Multiple combinations of these primers were applied to single stranded cDNA from several rat, mouse, and human sources, leading to the isolation of additional homologues of LMR1. Specifically, we identified fragments coresponding to the human and mouse counterparts of LMR1_r (LMR1_h from human cerebellum, isolated with primers IROSD3 and IROS D6; LRM1_m using the same primers on mouse day 11 embryo cDNA). Seven additional unique fragments were isolated by PCR with various pairs of these degenerate primers. Sequence comparison suggests that these seven clones represent two additional human genes and their orthologues from rat or mouse. Specifically they are referred to as LMR2_h (primers IROSD3 and IROSD6 on OVCAR-3 ovarian tumor cell line cDNA), LMR2_m (primers ROS1 and IROSD5 on mouse day 10 embryo cDNA), LRM2_r (primers IROSD3 and IROSD6 on rat PC12 cDNA), LMR2_h (primers IROSD3 and IROSD5 on human heart cDNA), LMR2_r (primers IROSD3 and IROSD5 on rat PC12 cDNA), LMR3_h (primers IROSD3 and IROSD6 on human fetal brain cDNA), and LMR3_m (primers TEK1 and IROSD5 on mouse day 12 embryo cDNA).

The partial cDNA clones from human LMR1, LMR2, and LMR3 were then used to probe cDNA libraries in order to isolate full length human cDNA clones. A 5,048 bp clone of LMR1_h (SEQ ID NO. 2) was isolated from a lambda ZAP cDNA library constructed from SNB75 cell line RNA. This clone spans all but the first 27 amino acids of the predicted 1384 amino acid human LMR1 protein (SEQ ID NO. 11). The true N-terminus of LMR1 however is contained on the rat cDNA clone. Two LMR2_h cDNA clones of 4,349 bp and 5,482 bp were isolated from an NCI-H460 human lung carcinoma cell line cDNA library and the SNB75 cDNA library, respectively. Together these clones span the complete 8,982 bp human LMR2 cDNA (SEQ ID NO. 5) and encode a protein of 1504 amino acids (SEQ ID NO. 14). Finally, a 1,583 bp clone of LMR3_h (SEQ ID NO. 8) was isolated from a lambda gt11 human brain cDNA library. This clone spans the N-terminal 473 amino acids of human LMR3 (SEQ ID NO. 17). Additional screening is ongoing to isolate the 3' end of the human LMR3 cDNA.

Each of the three LMR proteins begin with two closely spaced hydrophobic regions. The first hydrophobic stretch of LMR1 (aa 1–20), LMR2 (aa 1–26), and LMR3 (aa 1–20) meets the criteria signal peptide domains, with discriminant scores of 8.78, 18.95, and 10.76 respectively using the method of McGeoch (D. J. McGeoch, Virus Research, 3, 271, 1985), and with weight matrix scores of +3.45, 9.03, and 8.66 respectively (threshold=3.5) using the von Heijne algorithm (G. von Heijne, Nucl. Acids Res., 14, 4683, 1986). The second hydrophobic region of LMR1 (aa 38–64), LMR2 (aa 39–69), and LMR3 (aa 35–62) generate likelihood scores of −9.18, −17.09, and −11.25 (threshold=−2.0) respectively, using the ALOM method of Klein et al. (P. Klein, M. Kanehisa, and C. DeLisi, Biochim. Biophys. Acta, 815, 468, 1985) to predict transmembrane domains. Based on these analyses, LMR1, LMR2, and LMR3 are all predicted to be type Ia membrane proteins with very short extracellular domains of 18 (AFSSHFDPDGAPLSELSW), 12 (APLPQTGAGEAP), and 14 (SPAHPDGFALGRAP) amino acids respectively. Conceivably, these receptors may contain an additional co-receptor as present in many GPI-anchored cytokine receptors, GDNF-receptors, or contactin-related adhesion molecules. Co-immunoprecipitation studies will. allow us to address this issue.

LMR1, LMR2, and LMR3 all share a domain that conserves all 12 subdomains characteristic of eukaryotic protein kinases. The three human proteins share 52–59% amino acid sequence identity within this putative kinase domain whereas the rat, mouse, and human orthologues of LMR1 share 92–93t amino acid identity. The putative kinase domain of the LMRs is most related to that of other receptor tyrosine kinases. They share 33–36% amino acid identity with TRKA, TRKB, and TRKC and 31–35% identity with insulin receptor, IGFlR, Musk, Tyro10, DDR, and ROS. However two cytoplasmic tyrosine kinases, ITK and BMX are 33–34% identical to the kinase-like domain of LMR2. This analysis suggests the LMR receptors will likely represent a unique class or classes of RTKs. The kinase-like domain of the three LMRs do contain three atypical substitutions at residues that are highly conserved among all protein kinases: VAVK to V(V/I)VK in kinase domain II (aa 163–166 in LMR2), DFG to DYG (aa 281–283 in LMR2), and DVWS to NVWS (aa 329–332 in LMR2). The first substitution is a contact residue for the adenosine ring of ATP, and the presence of a hydrophobic residue in this position is unique to all known protein kinases. The remaining two substitutions are not known to be directly involved in the catalytic function of kinases and are present in other active kinases such as PIM1, and PKC. Whether these substitutions affect activity or specificity of the kinase-like domain can be addressed through in vitro kinase and FSBA-binding experiments.

Figure 1B-1:
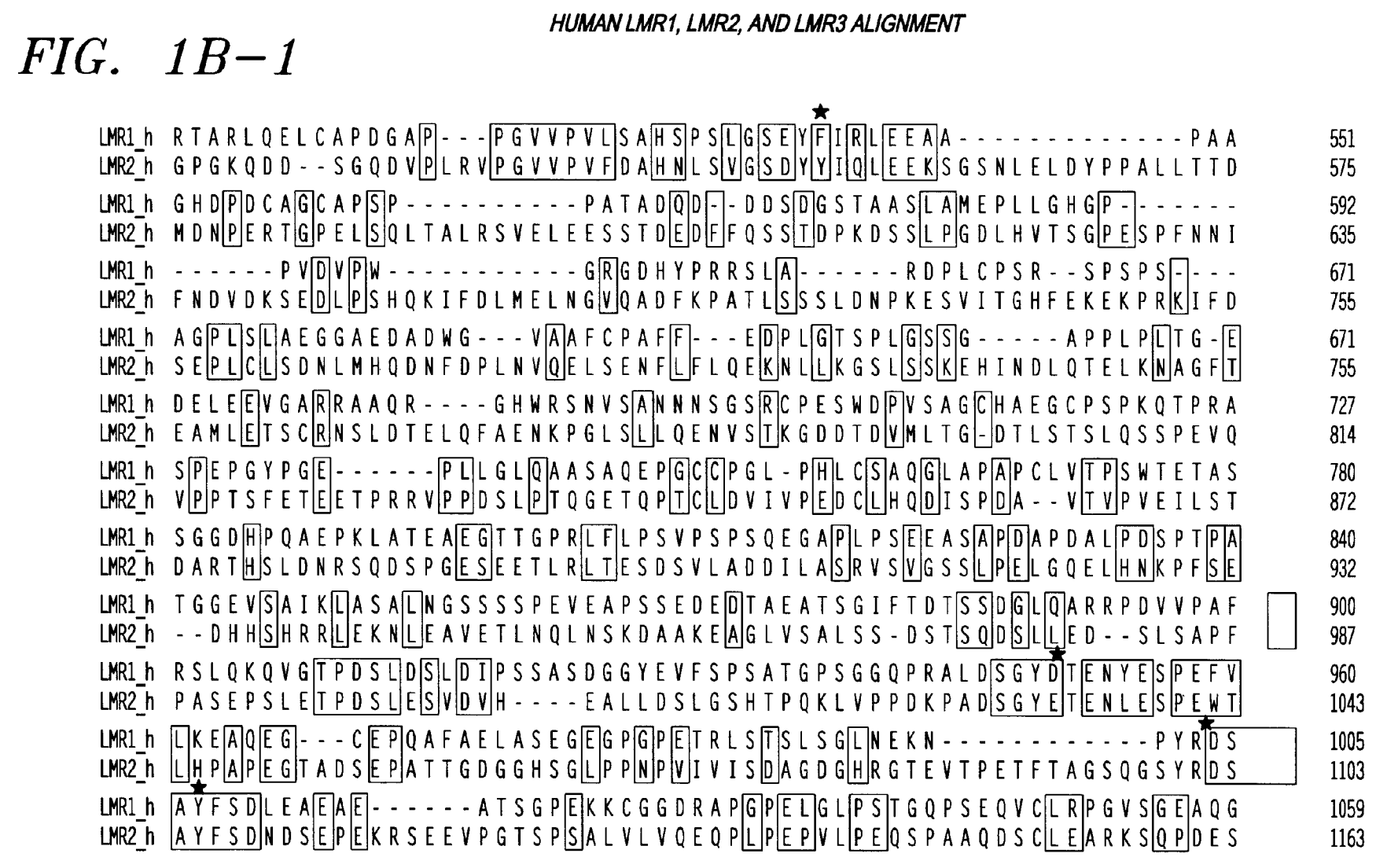

The C-terminal domains of LMR1, and LMR2, are 975 and 1093 amino acids respectively. The C-terminal domain of LMR3 is at least 153 aa (sequence analysis of the remaining C-terminal region of LMR3 is ongoing). These proteins were named Lemurs (LMR) as a reflection of their unusually long extracatalytic C-terminal tails. Within the C-tails are several conserved pockets of amino acid identity that contain 7 tyrosine residues (FIG. 1). Each of these may function as potential tyrosine phosphorylation sites, and may be of significance for LMR-specific signaling. These "tails" are also very hydrophilic and negatively charged, but otherwise lack significant homology to other proteins. Numerous isoforms have been identified for LMR1 and LMR2, resulting from alternative splicing or addition of a single base resulting in a frameshift and truncation of the C-terminal domain.

Expression Profile of Human LMRs

Northern blots of RNA from adult human tissue samples and human tumor cell lines were hybridized with DNA probes specific to human LMR1, LMR2, and LMR3. A single mRNA transcript was identified for each gene (LMR1=7 kb; LMR2=9kb; LMR3=5.1 kb), and all had distinct and restricted expression in specific cell types (FIGS. 3A and B). LMR1 was also analyzed by quantitatvie PCR on a variety of rat tissues RNA samples. LMR1, LMR2 and LMR3 expression in normal adult tissues was restricted to those of neuronal origin (adult brain, cortex, and cerebellum) and was absent from all other adult tissues examined. LMR1 was expressed at low levels in cell lines from 3 lung tumors, 1 CNS tumor, 1 colon tumor, and 2 melanomas. LMR3 expression was not detected in any of the 59 tumor cell lines. In contrast, LMR2 was widely and abundantely expressed in numerous tumor cell lines, particularly those of lung, breast, and colon origin.

In Situ Analysis of LMR Expression

LMR1, LMR2, and LMR3 developmental expression was analyzed by in situ hybridization on day 16 rat embryos (FIG. 4). LMR1 expression was tightly restricted to the dorsal root ganglia (DRGs) and the projecting nerves, and absent from all other neuronal and non-neuronal tissues examined. LMR3 was also abundantly expressed in DRGs, but had comparable expression in other embryonic neuronal structures including the spinal cord, thalamus, and brainstem, and lower levles in the specific regions of the midbrain and cortex. LMR3 was also expressed in the embryonic stomach and colon. LMR2 had a much broader expression profile than LMR1 or LMR3 in the day 16 rat embryo. LMR2 was expressed at high levels in the same neuronal tissues as LMR3 (DRGs, spinal cord, brainstem, thalamus, midbrain, and cortex), but LMR2 expression was also strong in the trigeminal nucleus, neuroretina, and the olfactory epithelium. LMR2 was also abundantely expressed in a variety of non-neuronal embryonic tissues including the stomach, intestine, and colon, the lung, kidney, liver and pancreas.

Expression of LMR1, LMR2, and LMR3 was also analyzed by in situ hybridization in coronal and saggital sections of the adult rat brain (FIG. 5). LMR1 was weakly expressed in the cerebellum, cortex, thalamic and amygdaloid nuclei, and brainstem. LMR3 was more abundantly expressed in the adult brain with highest expression in the hippocampus, cerebellum, anterior cortex, amygdaloid, thalamic, caudate, facial and supramammilary nuclei. LMR2 expression in the adult rat brain was stronger than that of LMR1 or LMR3, particularly in the purkinje layer of the cerebellum, the outer cortex, hippocampus, and in the thalmic, caudate/putamen, amygdaloid, facial, and trigeminal nuclei. LMR2 was also detected in the region of the piriform cortex, and substantia nigra.

Overall, the expression of LMR1 and LMR3 are highly restricted to neuronal tissues with minimal expression in other adult or embryonic organs or in human tumor cell lines. In contrast, LMR2 expression is limited to adult neuronal tissues, but is also very abundantly expressed in other non-neuronal fetal tissues and in numerous tumor cell lines. The onco-fetal pattern of LMR2 expression suggests it may serve as a selective target for cancer therapy.

Genomic Analysis and Chromosomal Localization of LMR2

PCR primer pairs were designed to specifically recognize LMR2 from genomic DNA. These primers were then be used to screen the Stanford G3 radiation hybrid panel of DNAs isolated from hamster-human somatic cell hybrids, in order to postionally map the LMR2 gene. LMR2 was mapped to chromosome 7q22.1. This chromosomal region had been reported to be amplified in pancreatic cancer, multiple-drug resistant cells, and in malignant solid tumors. Translocations in the region of 7q22 have been seen in myeloid leukemias, and endometrial polyps, and chromosome loss has been reported in breast, ovarian, prostate, and espophageal cancer, and in uterine leiomyomas. Analysis of the LMR2 gene/sequence from specimens isolated from these tumor sources will be necessary to validate LMR2's involvement in any of these tumor types.

The LMR2-specific primers were also used to isolate a ~130 kb BAC (bacterial artificial chromosome) clone spanning the entire human LMR2 gene. In total, 4 BAC clones were identified to contain the 3' UTR of the LMR2 gene (Plate pool 345–352/Row B/Column 10; Plate pool 457–464/Row J/Column 22; Plate pool 569–576/Row N/Column 18; and Plate pool 9–16/Row L/Column 6). The latter of these BAC clones was found to also contain the 5' end of the LMR2 cDNA clone. An additional 12 kb lambda human genomic clone containing the 5' most region of the cDNA clone was also isolated. Partial sequence analysis of the BAC clone revealed the location of numerous exons in LMR2, proving that the C-terminal isoforms of LMR2 were alternatively spliced transcripts. Additional sequence analysis of the lambda genomic clone and BAC clone identified two small introns in the N-terminal coding region of LMR2 (one near the junction of the predicted signal sequence), and revealed that the predicted 5' UTR of LMR2 was contiguous with the predicted start methionine, and that a stop codon is present in frame just upstream of our furthest cDNA clone. No upstream introns were obvious and a consensus "TATA Box" lies 259 bp upstream of the 5' most cDNA sequence suggestive that this may be the upstream LMR2 promoter region. In summary, the analysis of the genomic and cDNA clones suggest that the sequence presented (SEQ ID NO. 5) represents the complete coding sequence of human LMR2, and that it has an unusual membrane configuration, with a very short extracellular domain. This conclusion is further supported by the consistent presence of start methionine followed by a predicted signal peptide in the LMR1 and LMR3 clones. However, confirmation that these clones represent the entire LMR2 coding region awaits verification that the recombinant protein encodes a polypeptide of the same size as endogenous LMR2 and that immunolocalization studies demonstrate LMR2 toe a cell surface receptor (see below).

Example 2

Recombinant Expression of Novel of Novel RTKs
Materials and Methods Expression Vector
Construction Several expression constructs were generated from the human LMR2 cDNA including: a) full length LMR2_h in a pCDNA expression vector; b) a chimera between chicken TrkA extracellular domain and the transmembrane and cytoplasmic domains of human LMR2 in an adenovirus expression vector; c) a GST-fusion construct containing the juxtamembrane and cytoplasmic domain of LMR2 fused to the C-terminal end of a GST expression cassette; d) the kinase domain of LMR2_h fused to a GyrB expression cassette; e) a full length LMR2_h construct with a Lys to Ala (K to A) mutation at the predicted ATP binding site of the LMR2 kinase domain, inserted in the pCDNA vector; f) various truncated LMR2 constructs in the pCDNA vector, containing progressively larger C-terminal deletions.

The "K to A" mutant and the C-terminal truncation mutants of LMR2 might function as dominant negative constructs, and will be used to elucidate the function of LMR2.

Generation of Specific Immunoreagents to the Three Novel RTKs

Specific immunoreagents were raised in rabbits against KLH- or MAP-conjugated synthetic peptides corresponding to human LMR2. C-terminal peptides were conjugated to KLH with gluteraldehyde, leaving a free C-terminus. Internal peptides were MAP-conjugated with a blocked N-terminus. Additional immunoreagents can also generated by immunizing rabbits with the bacterially expressed GST-fusion protiens containing the cytoplasmic domains of LMR1, LMR2, and LMR3.

For LMR2, a GST fusion construct was genereated that encoded amino acids 71–840 of the human LMR2 protein. Peptide immunogens for human LMR2 include:

| # | conj | aa Sequence | LMR2 aa | LMR2 region |
|---|---|---|---|---|
| 489A | KLH | DSDIEQGGSSEDGEKD (SEQ ID NO:19) | 1488–1503 | C-tail |
| 491A | MAP | DDEIDFTPPAEDTPS (SEQ ID NO:20) | 84–98 | JMD |
| 494A | MAP | HFEKEKPRKIFDSEP (SEQ ID NO:21) | 684–698 | Doman B |
| 497A | MAP | GSYRDSAYFSDNDSEP (SEQ ID NO:22) | 1098–1113 | Domain C (2 Tyr) |

Transient Expression of the LMR1,2,3 in Mammalan Cells

The pcDNA expression plasmids (10 ug DNA/100 mm plate) containing the LMR2 constructs are introduced into 293 cells with lipofectamine (Gibco BRL). After 72 hours, the cells are harvested in 0.5 ml solubilization buffer (20 mM HEPES pH7.35, 150 mM NaCl, 10% glycerol, 1% Triton X-100, 1.5 mM MgCl$_2$, 1 mM EGTA, 2 mM phenylmethylsulfonyl fluoride, 1 μg/ml aprotinin). Sample aliquots were resolved by SDS polyacrylamide gel electrophoresis (PAGE) on 6% acrylamide/0.5% bis-acrylamide gels and electrophoretically transferred to nitrocellulose. Non-specific binding is blocked by preincubating blots in Blotto (phosphate buffered saline containing 5% w/v non-fat dried milk and 0.2% v/v nonidet P-40 (Sigma)), and recombinant protein was detected using the various anti-peptide or anti-GST-fusion specific antisera.

Immunostaining

Cells expressing endogenous LMRs, based on immunoblot analysis, were plated on glass slides and stained with LMR-specific antisera to determine the subcellular location of endogenous protein. Cells were fixed in methacarnes (60% Methanol/30% chloroform/10% glacial acetic acid) for 20 min, then post-fixed in 0.25% Tween20 in PBS. Slides were then blocked in 5% normal goat serum in PBS/0.25% Tween20 for 45 min. Slides were then incubated with a 1:500 dilution of LMR2-specific antisera from the 5th bleed of rabbits immunized with peptide 494A or 497A for 45 min at room temperature, washed 5× in PBS/0.25% Tween20. A 1:500 dilution of goat anti-rabbit F(ab')2 IgG-cyanine CY3 (Jackson Immunoresearch laboratories, West Grove, Pa.) was added for 30 min, followed by 6 washes in PBS/0.25% Tween20, and 2× in H2O. Slides were then air dried and mounted for analysis by fluroscent microscopy.

In Vitro Kinase Assays

Three days after transfection with the LMR2 expression contructs, a 10 cm plate of 293 cells was washed with PBS and solubilized on ice with 2 ml PBSTDS containing phosphatase inhibitors (10 mM NaHPO4, 7.25, 150 mM NaCl, 1% Triton X-100, 0.5% deoxycholate, 0.1% SDS, 0.2% sodium azide, 1 mM NaF, 1 mM EGTA, 4 mM sodium orthovanadate, 1% aprotinin, 5 μg/ml leupeptin). Cell debris was removed by centrifugation (12000×g, 15 min, 4° C.) and the lysate was precleared by two successive incubations with 50 ul of a 1:1 slurry of protein A sepharose for 1 hour each. One-half ml of the cleared supernatant was reacted with 10 ul of protein A purified LMR2 antisera (generated from the GST fusion protein) plus 50 ul of a 1:1 slurry of protein A-sepharose for 2 hr at 4° C. The beads were then washed 2 times in PBSTDS, and 2 times in HNTG (20 mM HEPES, pH7.5/150 mM NaCl, 0,1% Triton X-100, 10% glycerol).

The immunopurified LMR2 on sepharose beads was resuspended in 20 ul HNTG plus 30 mM MgCl2, 10 mM MnCl2, and 20 uCi [g32P]ATP (3000 Ci/mmol). The kinase reaction was run for 30 min at room temperature, and stopped by addition of HNTG supplemented with 50 mM EDTA. The samples were washed 6 times in HNTG, boiled 5 min in SDS sample buffer and analyzed by 6% SDS-PAGE followed by autoradiography. Phosphoamino acid analysis was performed by standard 2D methods on 32P-labeled LMR2 excised from the SDS-PAGE gel.

FSBA Labeling

Immunoprecipitated LMR2 was labeled with the ATP-analogue FSBA as described by Anostario, M Jr et al (Anal. Biochem 190,60–65, 1990) in the presence or absence of ATP competitor. FSBA-bound LMR2 was detected by immunoblot with anti-FSBA antibodies (Boehringer Mannheim).

RESULTS

The apparent molecular weight of each of the three novel RTKs can be determined by transient expression in human 293 embryonic kidney epithelial cells followed by immunoblotting with LMR-specific antisera. Surprisingly, the full length LMR2 cDNA construct encodes a protein that migrates at ~230 kDa on an 6% SDS-PAGE gel, whereas the cDNA predicts an unmodified protein of 164.9 kDa. The chimeric TrkA-LMR2 construct encodes a protein that migrates at above 250 kDa on an 6% SDS-PAGE gel, whereas the cDNA predicts a protein of ~207 kDa (plus13 potential glycosylation sites). Since there the predicted extracellular domain of LMR2 is only 12 amino acids, with no sites for glycosylation, the cause of the slower gel mobility is unclear. Based on a series of C-terminal deletion mutants it appears the discrepancy between calculated and apparent gel mobility is a result of the presence of the long, negatively charged C-terminal tail of LMR2. However, this analysis confirms the recombinant protein can be stabley produced in mammalian cells and provides a source of recombinant protein to confirm the specificity of the antisera.

The anti-GST fusion and peptide antisera were tested for their sensitivity and specificity on recombinant protein. The LMR1 and LMR2 anti-GST fusion antibodies were both confirmed to specifically recognize the appropriate recombinant protein in immunoprecipitation and Western blot. However their Western reactivity was weak, and they performed poorly on immunostaining. Anti-peptide antisera derived from LMR2 peptides 489A and 491A (SEQ ID NO. 19, and 20) worked on Western blots, but not for immunoprecipitation, whereas LMR2 peptides 494A and 497A (SEQ ID NO. 21, and 22) worked in Western blots, immunoprecipitation, and for cellular immunostaining. All LMR2 immunoreagents recognized a 230 kDa recombinant protein, whereas the 497A peptide antisera also detected an additional 130 kDa band on Western blot.

All expression constructs were confirmed to produce the encoded protein by Western blots and immunoprecipitation. A panel of human tumor cell lines were screened for expression of endogenous LMR2 by Western blot. The Western blot analysis concurred with the Northerns, with highest endogenous LMR2 expression detected in NCI-H441, COLO205, and MCF7 cells. The endogenous protein migrated at ~230 kDa, indistinguishable from the recombinant LMR2, further supporting that this cDNA encodes the full length LMR2 and that the protein has an unusually slow mobility in a reducing SDS-PAGE gel. These cells lines will be useful for characterization of the activity and biology of LMR2.

Immunolocalization of recombinant LMR2 in transient and stabley transfected 293 cells suggests it is both membrane and endoplasmic reticulum-associated. Assessment of the location of endogenous LMR2 in H441 cells is underway.

In vivo and in vitro phosphorylation assays were performed with recombinant and endogenous LMR2 following immunoprecipitation with LMR2-specific antisera. To date only serine and threonine phosphorylation has been detected associated with LMR2. Several distinct antibodies all detect comparable activity, suggesting the activity is associated with LMR2 and not due to antisera cross-reactivity. However, a similar amount of phosphorylation was also observed with the "kinase dead" K to A construct. These results suggest that either the "kinase dead" construct is still active, or that the activity is due to a serine kinase that is very tightly associated with LMR2. Experiments are underway to reassess kinase activity under different assay conditions (pH 5–8, variable ATP concentration, and presence of irreversible phosphatase inhibitors) and to determine if LMR2 can bind the the ATP-analogue FSBA.

The LMR2-specific antisera can also be used to co-immunoprecipate, substrates or co-receptors that associate with LMR2 from 35S-methionine/cysteine or 32P-labeled lysates. Since LMR2 has such an unusually short extracellular domain, the presence of an associated co-receptor could allow it access to modulation by a solbule or extracellular associated ligand. Owing to the presence of potential tyrosine phosphorylation sites in the stretches of amino acids that are conserved between LMR1, LMR2, and LMR3, it seems likely that these proteins may have uniquely specific substrates. Co-immunoprecipitation, random peptide libraries, phage display, and yeast two-hybrid techniques are all methods for identifying LMR2-selective substrates.

LMR1, LMR2, and LMR3 define a novel family of receptors that are structurally related to receptor tyrosine kinases. While their inherent catalytic activity is still under investigation, they all share the distinct motifs that typically characterize this class of enzymes. In addition, they possess extremely short extracellular domains and C-terminal tails of unprecedented length among RTKs. These structural features, along with several conserved C-terminal potential tyrosine phosphorylation sites suggests their biology may be unique among other receptors. Based on the restricted expression of all three LMRs to adult neuronal tissues and the upregulation of LMR2 in a wide variety of tumor cell lines, these proteins may be critical targets for neurodegenerative disorders or cancer. Ongoing experiments will characterize their effect on growth rate, DNA synthesis, cell-contact inhibition (foci formation), anchorage-independent growth (soft agar assays), and tumorigenicity in nude mice, and for their role in cell survival, apoptosis, or neurite outgrowth. Furthermore, the dominant negative constructs, neutralizing antisera, or antisense oligonucleotides can be used to address the inolvement of these novel RTKs in various biologic processess, both in normal development and disease.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Those references not previously incorporated herein by reference, including both patent and non-patent references, are expressly incorporated herein by reference for all purposes. Other embodiments are within the following claims.

What is claimed is:

1. A purified, isolated, or enriched nucleic acid molecule at least 1200 nucleotides in length,
   wherein the sequence of said nucleic acid molecule has at least 95% sequence identity or is exactly complementary to a gene encoding a kinase,
   wherein said gene comprises the nucleotide sequence set forth in any one of SEQ ID Nos:1, 3, 4, and 6–9.

2. A nucleic acid probe of 200 nucleotides in length for the detection of a nucleic acid encoding a kinase in a sample, wherein said kinase is encoded by a gene comprising a nucleotide sequence
   a) set forth in any one of SEQ ID Nos:1, 3, 4 or 6–9; or
   b) which encodes a polypeptide having an amino acid sequence set forth in any one of SEO ID Nos: 10, 12–13 or15–18.

3. An isolated or purified nucleic acid molecule encoding a human polypeptide expressed in a human tissue, obtainable by hybridization to a nucleotide sequence set forth in one of SEQ ID Nos:1, 3, 4, and 6–9 or a sequence exactly complementary thereto, wherein said hybridization conditions are at least as stringent as the following: 42° C. overnight at 6×SSC, 0.1% SDS, 1×Denhardt's solution, 100 g/ml denatured herring sperm DNA with 1–2×10$^6$ cpm/ml of $^{32}$P-labeled DNA probes; washing in 0.1×SSC/0.1% SDS at 65° C.

4. A recombinant nucleic acid molecule comprising a transcriptional initiation region functional in a cell, transcriptionally linked with a sequence exactly complemetary to an RNA sequence encoding a kinase polypeptide and a transciptional termination region functional in a cell, wherein said kinase is encoded by a gene comprising a nucleotide sequence set forth in any one of SEQ ID Nos:1, 3, 4, and 6–9.

5. A recombinant nucleic acid molecule comprising a transcriptional initiation region functional in a cell, transcriptionally linked with a sequence exactly complemetary to an RNA sequence encoding a kinase polypeptide and a transciptional termination region functional in a cell, wherein said kinase comprises an amino acid sequence set forth in any of SEQ ID Nos:10, 12–13, 15–18.

6. A recombinant DNA molecule comprising a vector or a promoter effective to initiate transcription in a host cell, and a nucleic acid sequence at least 200 nucleotides in length, wherein said sequence has at least 60% of a coding region of a gene encoding a kinase, wherein said gene is selected from the group consisting of SEQ ID Nos:1, 3, 4, and 6–9; or said kinase comprises an amino acid set forth in one of SEQ ID Nos:10, 12–13, 15–18.

7. A method of expression of one or more genes encoding kinase fragments in host cells, comprising the following steps:

(a) inserting into said cells one or more recombinant DNA molecules comprising a vector or promoter effective to initiate transcription in said cells, and a nucleic acid sequence at least 200 nucleotides in length, wherein said sequence has at least 95% sequence identity or is exactly complementary to a portion of a gene encoding a kinase, and wherein said gene i) has a nucleotide sequence set forth in any one of SEQ ID Nos:1, 3, 4, and 6–9 or ii) encodes a polypeptide set forth in any one of SEQ ID Nos:10, 12–13, 15–18; and (b) growing said cells in vitro.

8. The method of claim 7, wherein said method inhibits protein kinase activity.

9. A purified, isolated or enriched nucleic acid molecule which comprises a nucleotide sequence that:

(a) encodes a polypeptide comprising the amino acid sequence set forth in any one of SEQ ID Nos:10, 12–13, 15–18; or (b) is the complement of the nucleotide sequence of (a).

10. A purified, isolated or enriched nucleic acid molecule which hybridizes to a nucleic acid which encodes a polypeptides having an amino acid sequence set forth in any one of SEQ ID Nos: 10, 12–13 and 15–18, or an exact complement thereof, and encodes a naturally occurring lemur (LMR) polypeptide, wherein hybridization occurs under hybridization conditions at least as stringent as the following: 42° C. overnight at 6×SSC, 0.1% SDS, 1×Denhardt's solution, 100 g/ml denatured herring sperm DNA with $1-2 \times 10^6$ cpm/ml of $^{32}$P-labeled DNA probes; washing in 0.1×SSC/0.1% SDS at 65° C.

11. A purified, isolated or enriched nucleic acid molecule which (a) encodes a polypeptide comprising the amino acid sequence set forth in any one of SEQ ID Nos:10, 12–13, 15–18, except that it lacks one or more, but not all, of the domains selected from the group consisting of a C-terminal domain, a N-terminal domain and a catalytic region; or (b) is the complement of the nucleotide sequence of (a).

12. A purified, isolated, or enriched nucleic acid molecule which comprises a nucleotide sequence that:

(a) encodes a polypeptide comprising the amino acid sequence set forth in SEQ ID No: 14; or (b) is the complement of the nucleotide sequence of (a).

13. A purified, isolated or enriched nucleic acid molecule which hybridizes to a nucleic acid which encodes a polypeptide having the sequence set forth in SEQ ID NO:14 and encodes a naturally occurring LMR polypeptide, wherein hybridization conditions are at least as stringent as the following: 42° C. overnight at 6×SSC, 0.1% SDS, 1×Denhardt's solution, 100 g/ml denatured herring sperm DNA with $1-2 \times 10^6$ cpm/ml of $^{32}$P-labeled DNA probes; washing in 0.1×SSC/0.1% SDS at 65° C.

14. A purified, isolated or enriched nucleic acid molecule which (a) encodes a polypeptide comprising the amino acid sequence set forth in SEQ ID No:14, except that it lacks one or more, but not all, of the domains selected from the group consisting of a C-terminal domain, a N-terminal domain and a catalytic region; or (b) is the complement of the nucleotide sequence of (a).

15. A nucleic acid molecule which comprises a nucleotide sequence that:

(a) encodes a polypeptide comprising the amino acid sequence set forth in SEQ ID No: 11; or (b) is the complement of the nucleotide sequence of (a).

16. A purified, isolated or enriched nucleic acid molecule which hybridizes to a nucleic acid which encodes a polypeptide having the sequence set forth in SEQ ID NO:11, or an exact complement thereof, and encodes a naturally occurring LMR polypeptide, wherein hybridization conditions are at least as stringent as the following: 42° C. overnight at 6×SSC, 0.1% SDS, 1×Denhardt's solution, 100 g/ml denatured herring sperm DNA with $1-2 \times 10^6$ cpm/ml of $^{32}$P-labeled DNA probes; washing in 0.1×SSC/0.1% SDS at 65° C.

17. A purified, isolated or enriched nucleic acid molecule which (a) encodes a polypeptide comprising the amino acid sequence set forth in SEQ ID No:11, except that it lacks one or more, but not all, of the domains selected from the group consisting of a C-terminal domain, a N-terminal domain and a catalytic region; or (b) is the complement of the nucleotide sequence of (a).

18. A purified, isolated, or enriched nucleic acid molecule which (a) comprises at least 200 contiguous nucleotides of the nucleotide sequence set forth in SEQ ID NO:2; or (b) a nucleotide sequence encoding a polypeptide having at least 75 contiguous amino acids of the amino acid sequence set forth in SEQ ID NO:11.

19. A recombinant nucleic acid comprising the nucleic acid molecule of claim 12, claim 14, or claim 15, claim 17 or claim 18 and an initiation region functional in a cell transcriptionally linked with the nucleotide sequence.

* * * * *

UNITED STATES PATENT AND TRADEMARK OFFICE
CERTIFICATE OF CORRECTION

PATENT NO. : 6,136,581
DATED : October 24, 2000
INVENTOR(S) : Keith E. Joho and Gregory D. Plowman It is certified that error appears in the above-identified patent and that said Letters Patent is hereby corrected as shown below:

Column 99,
Line 2, please change "1200" to -- 200 --.

Signed and Sealed this

Fifth Day of April, 2005

JON W. DUDAS
*Director of the United States Patent and Trademark Office*

SEQUENCE LISTING (1) GENERAL INFORMATION:

(iii) NUMBER OF SEQUENCES:     53

(2) INFORMATION FOR SEQ ID NO: 1:

(i) SEQUENCE CHARACTERISTICS:
       (A) LENGTH:            2572 base pairs
       (B) TYPE:              nucleic acid
       (C) STRANDEDNESS:      single
       (D) TOPOLOGY:          linear (xi) SEQUENCE DESCRIPTION: SEQ ID NO: 1:

```
CCCGCCCCGG GGATGCCCAT CGCGCTGCTG GCCCTGGCCA TGTCGTCGTC CTTCTTCAAC       60

CCCAGCTTTG CCTTCAGCTC CCACTTCGAC CCGGACGGTG CCCCGCTCAG TGAGCTATCC      120

TGGTCCTCGT CCCTTGCAGT GGTTGCTGTG TCCTTCTCTG GGATCTTCAC TGTCATTGTC      180

CTCATGCTGG CCTGCCTGTG CTGTAAGAAG GGCGGCATTG GGTTCAAGGA GTTTGAGAAT      240

GCTGAAGGGG AAGAGTATGT GGCCGACTTC TCGGAGCAGG GCTCCCCGGC TGCTACTGTA      300

CAGAACGGCC CCGATGTGTA TGTCCTGCCT CTCACTGAGG TCTCCCTGCC CATGGCTAAG      360

CAGCCGGGTC GCTCAGTGCA ACTCCTCAAG TCCACGGACC TGGGCCGCCA CAGCCTCCTG      420

TACTTGAAGG AGATTGGCCA CGGTTGGTTT GGGAAGGTGT TCTTGGGGGA GGTGCACTCG      480

GGTGTCAGTG GCACGCAGGT GGTGGTGAAG GAGCTGAAGG CCAGCGCCAG TGTGCAGGAG      540

CAGATGCAGT TCCTGGAGGA GGCGCAGCCC TACAGGGCCC TGCAGCACAG CAACCTGCTT      600

CAGTGCCTGG CCCAGTGTGC TGAGGTGACC CCCTATTTGC TGGTTATGGA GTTCTGTCCC      660

CTGGGGGACC TCAAAGGTTA TCTACGGAGC TGCCGGGTGA CAGAGTCCAT GGCGCCTGAC      720

CCCCTTACCT TGCAGCGCAT GGCGTGCGAG GTGGCGTGTG GTGTCTTGCA TCTACATCGT      780

CACAACTATG TGCACAGTGA CCTGGCCCTG AGGAACTGCC TGCTGACGGC TGACCTGACA      840

GTGAAGGTTG GCGACTATGG CCTGGCCCAT TGCAAATACA GGGAAGACTA CCTCGTGACG      900

GCCGACCAGT TGTGGGTGCC GCTGCGTTGG ATCGCGCCAG AGCTGGTGGA TGAGGTGCAT      960

GGCAACCTAC TGGTGGTGGA CCAGACTAAG ACCAGCAATG TGTGGTCCCT GGGTGTGACC     1020

ATCTGGGAGC TTTTCGAGTT GGGCGCGCAG CCCTACCCCC AGCACTCGGA CCGGCAGGTG     1080

CTGGCTTACG CCGTCCGAGA ACAGCAACTT AAGTTGCCCA AGCCCCAGCT ACAGCTGACT     1140

CTGTCTGATC GATGGTACGA GGTGATGCAG TTCTGCTGGC TTCAGCCAGA ACAGAGGCCT     1200

ACGGCTGAGG AGGTTCATCT GCTGCTGTCC TACTTGTGCG CCAAGGGCAC CACGGAGCTG     1260

GAGGAGGAGT TCGAGCGGCG CTGGCGCTCC CTGCGGCCGG GGGCAGCGC GGGGCTGGGC      1320

TCAGCTTCCA CAGTCCCGGC AGCTGCCGCA TCTGAACTCA CTGCTGCTTC ATCTTTCCCG     1380

CTGCTGGAGC AGTTCACCAG TGACGGCTTC CACGTGGACA GCGACGACGT GCTGACAGTC     1440

ACTGAGACGA GCCACGGCCT CAACTTCGAA TACAAGTGGG AGGCTGGCTG TGGCGCTGAG     1500

GCTTACCCGC CCCCAGGCGC TGCTTTCAGC CCAGGTTCCG CAGGGCGCCT GCAGGAGCTG     1560

TGTGCACCCG ACAGCTCGCC GCCGGGTGTG GTGCCGGTCC TCAGTGCCCA CAGCCCCTCA     1620

GTGGGTAGCG AGTACTTCAT CCGCCTGGAG GGGGCAGTGC CGGCTGCTGG CCATGACCCA     1680

GACTGTGCCG GCTGTGCTCC CAGCCCCCAA GCTGTGTCCG AGCAGGACAA TAACTCTGAG     1740

GAGAGCACCG CTGCATCCCT TGTCATGGAG CCGCTTCTGG GCCACGCACC ACCCACTGGG     1800

GGCCTGTGGG GCCCCTGCGA CCATCATTCT CGAAGGAGGC AAGAGCCACC CTGCCCCTCA     1860
```

```
CGCTCACCCT CTCCTGGGAC CCCGATGTTG CCAGCTGAAG ACATAGACTG GGGTGTAGCT    1920

ACCTTCTGCC CACCCTTTTT TGATGACCCA CTGGGCACAT CTCCCTCTGG GAGTCCTGGG    1980

GCCCAGCCAT CCCCCAGTGA TGAGGAGCTG GAGGAGGGAA AGACTGGGAG GGCTGCTCAG    2040

TGTGGACACT GGAGCTCTAA CATGTCTGCC AACAATAACA GTGGCAGTCG AGACCCAGAA    2100

TCCTGGGATC CTGGCTATGT GAGCAGCTTC ACAGACAGCT ACAGGGACGA CTGCTCCAGC    2160

TTAGAGCAGA CCCCTCGGGC CTCCCCTGAG CTGGGCCATC CCCTGTCCCA GGAGGATTCC    2220

AGAGATTTTT TACCTGGGCT AGTAGCAGCT TCCCCTGGCC AGGAGTCAAG CCGTTGCTTC    2280

AACCTGCTCC CTCTGTGTCC TGCCAAAGGC CTGGCACCTG CTGCTTGCCT CGTCCCACCC    2340

CCCTGGACAG AGGCAGCTGT AGGTGGGGCT GAGAACCCCA TTGTCGAACC CAAACTTGCC    2400

CAGGAGGCTG AGGGCTCTGC TGAACCCCAG CTACCCCTTC CTTCTGTCCC CTCCCCATCC    2460

CACGAAGGAG CCTCGCTTCC CTCGGAGGAG GCAAGCGCTC CTGACATCCA GCCTGCCTCT    2520

CCTACACCCG CTGCTGGCAG CTGGGTGACC GTCCTGAGGT CGACGCGGCC GC            2572

(2) INFORMATION FOR SEQ ID NO: 2:

(i) SEQUENCE CHARACTERISTICS:
        (A) LENGTH:         5267 base pairs
        (B) TYPE:           nucleic acid
        (C) STRANDEDNESS:   single
        (D) TOPOLOGY:       linear (xi) SEQUENCE DESCRIPTION: SEQ ID NO: 2:

GAATTCCCCA GCTTCGCCTT CAGCTCGCAC TTCGACCCCG ACGGCGCCCC GCTCAGCGAG      60

CTGTCCTGGG CATCCTCCCT CGCCGTGGTG GCTGTGTCTT TCTCCGGGCT CTTCGCCGTC     120

ATCGTCCTCA TGCTGGCCTG CCTGTGCTGT AAGAAGGGCG GTATCGGGTT CAAGGAGTTT     180

GAGAATGCGG AGGGGGACGA GTACGCAGCC GACCTGGCGC AGGGCTCCCC GGCCACGGCA     240

GCACAGAACG GGCCCGACGT GTACGTCCTG CCACTCACGG AGGTCTCCTT GCCCATGGCC     300

AAGCAGCCTG GGCGCTCAGT GCAGCTCCTC AAGTCCACAG ACGTGGGCCG GCACAGCCTC     360

CTGTACCTGA AGGAAATCGG CCGTGGCTGG TTCGGGAAGG GAAATCGGCC GTGGCTGGTT     420

CGGGAAGGTG TTCCTGGGGG AGGTGAACTC TGGCATCAGC AGTGCCCAGG TGGTGGTGAA     480

GGAGCTGCAG GCTAGTGCCA GCGTGCAGGA GCAGATGCAG TTCCTGGAGG AGGTGCAGCC     540

CTACAGGGCC CTGAAGCACA GCAACCTGCT CCAGTGCCTG GCCCAGTGCG CCGAGGTGAC     600

GCCCTACCTG CTGGTGATGG AGTTCTGCCC ACTGGGGGAC CTCAAGGGCT ACCTGCGGAG     660

CTGCCGGGTG GCGGAGTCCA TGGCTCCCGA CCCCCGGACC CTGCAGCGCA TGGCCTGTGA     720

GGTGGCCTGT GGCGTCCTGC ACCTTCATCG CAACAATTTC GTGCACAGCG ACCTGGCCCT     780

GCGGAACTGC CTGCTCACGG CTGACCTGAC GGTGAAGATT GGTGACTATG GCCTGGCTCA     840

CTGCAAGTAC AGAGAGGACT ACTTCGTGAC TGCCGACCAG CTGTGGGTGC CTCTGCGCTG     900

GATCGCGCCA GAGCTGGTGG ACGAGGTGCA TAGCAACCTG CTCGTCGTGG ACCAGACCAA     960

GAGCGGGAAT GTGTGGTCCC TGGGCGTGAC CATCTGGGAG CTCTTTGAGC TGGGCACGCA    1020

GCCCTATCCC CAGCACTCGG ACCAGCAGGT GCTGGCGTAC ACGGTCCGGG AGCAGCAGCT    1080

CAAGCTGCCC AAGCCCCAGC TGCAGCTGAC CCTGTCGGAC CGCTGGTACG AGGTGATGCA    1140

GTTCTGCTGG CTGCAGCCCG AGCAGCGGCC CACAGCCGAG GAGGTGCACC TGCTGCTGTC    1200

CTACCTGTGT GCCAAGGGCG CCACCGAAGC AGAGGAGGAG TTTGAACGGC GCTGGCGCTC    1260

TCTGCGGCCC GGCGGGGGCG GCGTGGGGCC CGGGCCCGGT GCGGCGGGGC CCATGCTGGG    1320
```

-continued

```
CGGCGTGGTG GAGCTCGCCG CTGCCTCGTC CTTCCCGCTG CTGGAGCAGT TCGCGGGCGA    1380

CGGCTTCCAC GCGGACGGCG ACGACGTGCT GACGGTGACC GAGACCAGCC GAGGCCTCAA    1440

TTTTGAGTAC AAGTGGGAGG CGGGCCGCGG CGCGGAGGCC TTCCCGGCCA CGCTGAGCCC    1500

TGGCCGCACC GCACGCCTGC AGGAGCTGTG CGCCCCCGAC GGCGCGCCCC CGGGCGTGGT    1560

TCCGGTGCTC AGCGCGCACA GCCCGTCGCT GGGCAGCGAG TACTTCATCC GCCTAGAGGA    1620

GGCCGCACCC GCCGCCGGCC ACGACCCTGA CTGCGCCGGC TGCGCCCCCA GTCCACCTGC    1680

CACCGCGGAC CAGGACGACG ACTCTGACGG CAGCACCGCC GCCTCGCTGG CCATGGAGCC    1740

GCTGCTGGGC CACGGGCCAC CCGTCGACGT CCCCTGGGGC CGCGGCGACC ACTACCCTCG    1800

CAGAAGCTTG GCGCGGGACC CGCTCTGCCC CTCACGCTCT CCCTCGCCCT CGGCGGGGCC    1860

CCTGAGTCTG GCGGAGGGAG GAGCGGAGGA TGCAGACTGG GGCGTGGCCG CCTTCTGTCC    1920

TGCCTTCTTC GAGGACCCAC TGGGCACGTC CCCTTTGGGG AGCTCAGGGG CGCCCCCGCT    1980

GCCGCTGACT GGCGAGGATG AGCTAGAGGA GGTGGGAGCG CGGAGGGCCG CCCAGCGCGG    2040

GCACTGGCGC TCCAACGTGT CAGCCAACAA CAACAGCGGC AGCCGCTGTC CAGAGTCCTG    2100

GGACCCCGTC TCTGCGGGCT GCCACGCTGA GGGCTGCCCC AGTCCAAAGC AGACCCCACG    2160

GGCCTCCCCC GAGCCGGGGT ACCCTGGAGA GCCTCTGCTT GGGCTCCAGG CAGCCTCTGC    2220

CCAGGAGCCA GGCTGCTGCC CCGGCCTCCC TCATCTATGC TCTGCCCAGG GCCTGGCACC    2280

TGCTCCCTGC CTGGTTACAC CCTCCTGGAC AGAGACAGCC AGTAGTGGGG GTGACCACCC    2340

GCAGGCAGAG CCCAAGCTTG CCACGGAGGC TGAGGGCACT ACCGGACCCC GCCTGCCCCT    2400

TCCTTCCGTC CCCTCCCCAT CCCAGGAGGG AGCCCCACTT CCCTCGGAGG AGGCCAGTGC    2460

CCCCGACGCC CCTGATGCCC TGCCTGACTC TCCCACGCCT GCTACTGGTG GCGAGGTGTC    2520

TGCCATCAAG CTGGCTTCTG CCCTGAATGG CAGCAGCAGC TCTCCCGAGG TGGAGGCACC    2580

CAGCAGTGAG GATGAGGACA CGGCCGAGGC CACCTCAGGC ATCTTCACCG ACACGTCCAG    2640

CGACGGCCTG CAGGCCAGGA GGCCGGATGT GGTGCCAGCC TTCCGCTCTC TGCAGAAGCA    2700

GGTGGGGACC CCCGACTCCC TGGACTCCCT GGACATCCCG TCCTCAGCCA GTGATGGTGG    2760

CTATGAGGTC TTCAGCCCGT CGGCCACTGG CCCCTCTGGA GGGCAGCCGC GAGCGCTGGA    2820

CAGTGGCTAT GACACCGAGA ACTATGAGTC CCCTGAGTTT GTGCTCAAGG AGGCGCAGGA    2880

AGGGTGTGAG CCCCAGGCCT TTGCGGAGCT GGCCTCAGAG GGTGAGGGCC CCGGGCCCGA    2940

GACACGGCTC TCCACCTCCC TCAGTGGCCT CAACGAGAAG AATCCCTACC GAGACTCTGC    3000

CTACTTCTCA GACCTCGAGG CTGAGGCCGA GGCCACCTCA GGCCCAGAGA AGAAGTGCGG    3060

CGGGGACCGA GCCCCCGGGC CAGAGCTGGG CCTGCCGAGC ACTGGGCAGC CGTCTGAGCA    3120

GGTCTGTCTC AGGCCTGGGG TTTCCGGGGA GGCACAAGGC TCTGGCCCCG GGAGGTGCT    3180

GCCCCCACTG CTGCAGCTTG AAGGGTCCTC CCCAGAGCCC AGCACCTGCC CCTCGGGCCT    3240

GGTCCCAGAG CCTCCGGAGC CCCAAGGCCC AGCCAAGGTG CGGCCTGGGC CCAGCCCCAG    3300

CTGCTCCCAG TTTTTCCTGC TGACCCCGGT TCCGCTGAGA TCAGAAGGCA ACAGCTCTGA    3360

GTTCCAGGGG CCCCCAGGAC TGTTGTCAGG GCCGGCCCCA CAAAAGCGGA TGGGGGGCCC    3420

AGGCACCCCC AGAGCCCCAC TCCGCCTGGC TCTGCCCGGC CTCCCTGCGG CCTTGGAGGG    3480

CCGGCCGGAG GAGGAGGAGG AGGACAGTGA GGACAGCGAC GAGTCTGACG AGGAGCTCCG    3540

CTGCTACAGC GTCCAGGAGC CTAGCGAGGA CAGCGAAGAG GAGGCGCCGG CGGTGCCCGT    3600

GGTGGTGGCT GAGAGCCAGA GCGCGCGCAA CCTGCGCAGC CTGCTCAAGA TGCCCAGCCT    3660
```

```
GCTGTCCGAG ACCTTCTGCG AGGACCTGGA ACGCAAGAAG AAGGCCGTGT CCTTCTTCGA    3720

CGACGTCACC GTCTACCTCT TTGACCAGGA AAGCCCCACC CGGGAGCTCG GGGAGCCCTT    3780

CCCGGGCGCC AAGGAATCGC CCCCTACGTT CCTTAGGGGG AGCCCCGGCT CTCCCAGCGC    3840

CCCCAACCGG CCGCAGCAGG CTGATGGCTC CCCAAATGGC TCCACAGCGG AAGAGGGTGG    3900

TGGGTTCGCG TGGGACGACG ACTTCCCGCT GATGACGGCC AAGGCAGCCT TCGCCATGGC    3960

CCTAGACCCG GCCGCACCCG CCCCGGCTGC GCCCACGCCC ACGCCCGCTC CCTTCTCGCG    4020

CTTCACGGTG TCGCCCGCGC CCACGTCCCG CTTCTCCATC ACGCACGTGT CTGACTCGGA    4080

CGCCGAGTCC AAGAGAGGAC CTGAAGCTGG TGCCGGGGGT GAGAGTAAAG AGGCTTGAGA    4140

CCTGGGCAGC TCCTGCCCCT CAAGGCTGGC GTCACCGGAG CCCCTGCCAG GCAGCAGCGA    4200

GGATGGTGAC CGAGAAGGTG GGGACCACGT CCTGGTGGCT GTTGGCAGCA GATTCAGGTG    4260

CCTCTGCCCC ACGCGGTGTC CTGGAGAAGC CCGTGGGATG AGAGGCCCTG GATGGTAGAT    4320

CGGCCATGCT CCGCCCCAGA GGCAGAATTC GTCTGGGCTT TTAGGCTTGC TGCTAGCCCC    4380

TGGGGGCGCC TGGAGCCACA GTGGGTGTCT GTACACACAT ACACACTCAA AAGGGGCCAG    4440

TGCCCCTGGG CACGGCGGCC CCCACCCTCT GCCCTGCCTG CCTGGCCTCG GAGGACCCGC    4500

ATGCCCCATC CGGCAGCTCC TCCGGTGTGC TCACAGGACA CTTAAACCAG GACGAGGCAT    4560

GGCCCCGAGA CACTGGCAGG TTTGTGAGCC TCTTCCCACC CCCTGTGCCC CCACCCTTGC    4620

CTGGTTCCTG GTGGCTCAGG GCAAGGAGTG GCCCTGGGCG CCCGTGTCGG TCCTGTTTCC    4680

GCTGCCCTTA TCTCAAAGTC CGTGGCTGTT TCCCCTTCAC TGACTCAGCT AGACCCGTAA    4740

GCCCACCCTT CCCACAGGGA ACAGGCTGCT CCCACCTGGG TCCCGCTGTG CCACGGTGG    4800

GCAGCCCAAA AGATCAGGGG TGGAGGGGCT TCCAGGCTGT ACTCCTGCCC CGTGGGCCCC    4860

GTTCTAGAGG TGCCCTTGGC AGGACCGTGC AGGCAGCTCC CCTCTGTGGG GCAGTATCTG    4920

GTCCTGTGCC CCAGCTGCCA AAGGAGAGTG GGGGCCATGC CCCGCAGTCA GTGTTGGGGG    4980

GCTCCTACCT ACAGGGAGAG GGATGGTGGG GAAGGGGTGG AGCTGGGGGC AGGGCAGCAC    5040

AGGGAATATT TTTGTAACTA ACTAACTGCT GTGGTTGGAG CGAATGGAAG TTGGGTGATT    5100

TTAAGTTATT GTTGCCAAAG AGATGTAAAG TTTATTGTTG CTTCGCAGGG GGATTTGTTT    5160

TGTGTTTTGT TTGAGGCTTA GAACGCTGGT GCAATGTTTT CTTGTTCCTT GTTTTTTAAG    5220

AGAAATGAAG CTAAGACAAA AGAAAAAAAA AAAAAAAAA ACTCGAG                  5267

(2) INFORMATION FOR SEQ ID NO: 3:

(i) SEQUENCE CHARACTERISTICS:
        (A) LENGTH:        245 base pairs
        (B) TYPE:          nucleic acid
        (C) STRANDEDNESS:  single
        (D) TOPOLOGY:      linear (xi) SEQUENCE DESCRIPTION: SEQ ID NO: 3:

GATGGCCACG GCTGGTTCGG AAAGGTATTT TTGGGGGAGG TACACTCGGG CGTCAGTGGC      60

ACGCAGGTGG TGGTGAAGGA GCTGAAGGTG AGCGCCAGCG TGCAGGAGCA GATGCAGTTC     120

CTGGAGGAGG CGCAGCCCTA CAGGGCCCTG CAGCACAGCA ACCTGCTCCA GTGCCTGGCC     180

CAGTGTGCTG AAGTGACCCC CTACCTGCTG GTTATGGAGT TCTGCCCATT CGGCGACCTG     240

AAATC                                                                245

(2) INFORMATION FOR SEQ ID NO: 4:

(i) SEQUENCE CHARACTERISTICS:
```

(A) LENGTH:          801 base pairs
           (B) TYPE:            nucleic acid
           (C) STRANDEDNESS:    single
           (D) TOPOLOGY:        linear (xi) SEQUENCE DESCRIPTION: SEQ ID NO: 4:

GATGAGATCG GCTTTAAGGA GTTTGAAGAT AATTTTGATG ATGAGATAGA CTTCACACCA      60

CCAGCAGAAG ACACCCCCTC TGTCCAGTCC CCAGCAGAGG TCTTCACACT CTCAGTGCCA     120

AACATTTCAC TTCCAGCCCC ATCCCAGTTC CAGTCTTCTG TGGGTTTGAA GTCTCAGGTC     180

GCTCGCCACA GTCTAAACTA TATACAGGAG ATTGGGAATG GCTGGTTTGG GAAGGTGCTC     240

CTGGGAGAGA CTTACACAGG CACCAGCGTC ACAAGAGTCA TAGTGAAGGA GTTAAAAGTC     300

AGTGCAAGCC CAAAGGAACA AGATACTTTC CTGAACAGTG GAGAGCCTTA CTACATTCTT     360

CAGCATCCGA ATGTTCTTCA GTGTGTCGGG CAGTGCGTGG AAGCCATTCC CTACCTTCTG     420

GTGTTTGAGT TCTGCGACCT GGGTGACCTG AAGGCTTACC TGCACAATGA ACAAGAGCAC     480

GTGCGCAGCG AGTCACAGAC CATGCTGCTG CAGAGGATGG CGTGCGAGAT TGCCGCAGGG     540

CTGGCAGCCA TGCACAAGCT GCACTTCCTG CACAGTGATC TGGCCCTACG GAACTGTTAT     600

CTCACCTCCG ACCTAAACGT CAAAGTGGGT GACTATGGGA TAGGCTTCAG CAGATATAAG     660

GAGGATTACA TAGAGACGGA TGACAAAAAA ATTTTCCCCC TGAGATGGAC TGCTCCAGAA     720

TTAGTGACCA GCTTTCAAGA CAGACTCTTG ACCGCAGATC AGACTAAGTA CAGTAACATA     780

TGGACGCTAG GCGTGACAAT C                                              801

(2) INFORMATION FOR SEQ ID NO: 5:

(i) SEQUENCE CHARACTERISTICS:
           (A) LENGTH:          8982 base pairs
           (B) TYPE:            nucleic acid
           (C) STRANDEDNESS:    single
           (D) TOPOLOGY:        linear (xi) SEQUENCE DESCRIPTION: SEQ ID NO: 5:

GAATTCGGCA CGAGTCATGG CGGCGGGAGC GCGGCTTCCC AGGCCCGCCG CTCCGCAGGG      60

CTGCTGGCGT TGCTGCTGTT GAGAGGCGGC GGCGGCGGCG CAGGCGGGCG GGAAGGATGG     120

TGTTTCTGCG ACTGGAGCGG CAGGTGCGGA CCGGGAGCCG GACCGAGGTT TGGCAGAAGC     180

AACGTGTGCT CGGGAGCAAC CGGCGCGGGT GCCACTGAGG CAGCGGAGGG AGGCAGGATC     240

GACTGACGGG CGAACGGACG GACGGACGGA AGGCGACTCG AGGGCCGGCC CCGGAGCCGC     300

GCCGTGGGCG AGATGCCGGG GCCGCCGGCG TTGCGGCGGA GGCTGCTGCT GCTGCTGCTG     360

GTCCTCCTGA TCGCCGGCAG TGCTGGGGCC GCGCCACTTC CGCAAACAGG TGCAGGGGAG     420

GCGCCACCTG CTGCAGAAGT TTCCTCATCT TTTGTGATCC TGTGTGTGTG CAGTTTAATA     480

ATATTAATAG TGTTAATTGC AAACTGTGTA TCCTGCTGTA AGGACCCAGA AATAGACTTT     540

AAGGAATTTG AAGATAATTT TGATGATGAG ATAGATTTCA CACCACCAGC AGAAGACACT     600

CCCTCTGTTC AGTCCCCAGC AGAGGTCTTC ACACTTCAG TACCAAATAT TTCACTCCCA     660

GCTCCCTCGC AATTCCAGCC TTCTGTAGAG GGATTGAAGT CTCAAGTTGC CGCCACAGT     720

CTAAACTACA TACAGGAAAT TGGAAATGGC TGGTTTGGAA AGGTTCTCTT GGGAGAGATT     780

TACACGGGCA CTAGCGTAGC AAGAGTCATC GTGAAGGAGT TAAAAGCAAG TGCCAACCCA     840

AAGGAACAAG ATACTTTTTT GAAAATGGA GAACCTTACT ACATTCTTCA GCATCCAAAT     900

ATTCTTCAGT GTGTTGGACA GTGCGTAGAA GCGATTCCCT ACCTCCTGGT GTTTGAGTTC     960

TGTGACTTGG GTGACCTGAA GGCGTATCTG CGCAGCGAGC AGGAGCACAT GCGGGGGGAC    1020

-continued

```
TCACAGACCA TGCTGCTGCA GAGGATGGCG TGCGAGGTCG CCGCGGGGCT GGCCGCCATG    1080

CACAAGCTGC ACTTCCTGCA CAGTGATTTA GCCCTGCGGA ATTGTTTTCT CACCTCCGAC    1140

TTAAATGTGA AAGTGGGAGA TTACGGAATA GGATTCAGCA GGTACAAGGA GGATTATATT    1200

GAAACAGATG ATAAAAAAGT TTTCCCTCTG CGATGGACTG CTCCAGAATT AGTAACCAGC    1260

TTTCAAGACA GACTGCTAAC TGCAGATCAG ACTAAGTATA GTAATATCTG GTCTCTGGGT    1320

GTGACACTTT GGGAGCTTTT TGACAATGCC GCACAGCCGT ATTCAAACCT TTCCAACTTA    1380

GATGTCCTCA ACCAAGTCAT TAGAGAGAGA GACACAAAAC TCCCGAAGCC CCAGCTGGAG    1440

CAGCCCTACT CTGATAGATG GTATGAAGTC TTACAGTTCT GTTGGCTGTC ACCAGAAAAG    1500

AGACCCGCGG CTGAAGATGT GCACAGGCTG CTGACTTACC TGCGGCTGCA GAGCCAGCGG    1560

GACTCAGAGG TCGACTTTGA ACAGCAGTGG AACGCTCTGA AGCCGAACAC AAACAGCAGA    1620

GACTCCTCCA ACAATGCTGC ATTCCCAATT CTCGACCACT TGCCAGGGA CCGGCTGGGT    1680

CGTGAAATGG AGGAAGTCCT CACCGTGACC GAAACCAGCC AGGGCCTGAG CTTCGAGTAT    1740

GTCTGGGAGG CCGCTAAGCA CGACCACTTT GACGAGCGCA GCCGGGGCCA CCTGGACGAA    1800

GGCTTGTCCT ACACGAGCAT CTTCTATCCG GTTGAAGTTT TTGAGAGTTC GCTTTCAGAT    1860

CCTGGGCCCG GAAAGCAAGA TGACAGCGGC CAGGATGTCC CCCTGAGGGT CCCTGGAGTG    1920

GTTCCTGTTT TTGATGCCCA CAACCTTTCT GTTGGAAGCG ACTATTATAT CCAGTTAGAA    1980

GAAAAAAGTG GTAGTAACTT GGAGCTTGAT TACCCACCAG CGCTGCTCAC AACCGACATG    2040

GATAATCCAG AAAGGACTGG CCCTGAACTG TCCCAGCTCA CGGCGCTCAG GAGCGTTGAA    2100

CTTGAGGAGT CCAGTACAGA TGAGGACTTC TTCCAAAGCA GTACAGACCC CAAAGACTCT    2160

AGCTTACCAG GGGACTTACA CGTGACCAGT GGCCCCGAGA GCCCTTTCAA CAATATATTT    2220

AATGATGTGG ACAAATCGGA AGATTTGCCC AGTCACCAAA AAATATTCGA CTTAATGGAA    2280

TTAAACGGAG TTCAAGCCGA CTTTAAACCT GCCACTTTAA GTTCCAGTTT GGATAACCCC    2340

AAAGAGTCAG TCATAACAGG CCACTTTGAG AAAGAAAAGC CCCGTAAGAT TTTTGACAGT    2400

GAGCCTCTCT GCCTATCAGA TAATCTTATG CACCAAGATA ATTTTGATCC ATTGAATGTT    2460

CAAGAATTGT CAGAAAACTT TTTATTTCTT CAAGAGAAAA ACTTACTAAA AGGCTCATTG    2520

TCCAGCAAAG AACACATAAA TGATCTTCAG ACAGAACTTA AGAATGCTGG TTTTACTGAA    2580

GCTATGTTAG AAACGTCATG TAGAAACTCT TTAGATACTG AGCTTCAGTT TGCTGAAAAT    2640

AAGCCAGGCT TGTCTTTGTT GCAGGAAAAC GTAAGCACAA AGGGTGACGA TACAGATGTC    2700

ATGCTCACAG GTGACACTTT GAGCACCTCA TTGCAGTCTT CCCCGGAAGT GCAGGTACCT    2760

CCTACCTCCT TCGAAACAGA AGAAACGCCC CGTCGGGTAC CCCCAGACTC ACTCCCAACA    2820

CAGGGAGAAA CCCAGCCCAC GTGTTTAGAT GTTATTGTCC CGGAGGACTG TCTCCACCAG    2880

GACATCAGTC CAGACGCTGT GACTGTCCCG GTTGAAATTC TCTCAACTGA TGCCAGAACC    2940

CACAGCCTGG ATAACAGGTC CCAGGACTCT CCTGGCGAGA GTGAGGAGAC CCTGCGACTC    3000

ACCGAAAGTG ACTCTGTTCT TGCTGATGAC ATCCTTGCCA GCAGGGTGAG TGTAGGGAGT    3060

AGTCTCCCGG AACTGGGACA GGAATTGCAC AATAAACCAT TTCGGAAGA CCATCACAGT    3120

CATCGCCGGC TAGAGAAAAA CTTAGAGGCT GTGGAGACTT AAATCAGCT CAATTCTAAA    3180

GACGCAGCAA AGAAGCAGG CTTGGTGTCT GCCCTCTCCT CGGACTCAAC CAGTCAGGAC    3240

AGCCTCCTGG AGGACAGCTT GTCAGCACCC TTCCCAGCCT CTGAGCCGTC CCTGGAAACC    3300

CCGGACTCTC TGGAGTCAGT GGATGTCCAC GAAGCGCTAC TGGACTCTTT AGGATCTCAC    3360
```

```
ACTCCCCAGA AACTAGTGCC CCCCGATAAG CCGGCAGACA GTGGCTACGA AACAGAGAAC    3420

TTGGAGTCTC CCGAGTGGAC CTTGCATCCC GCTCCCGAGG GCACCGCAGA CTCAGAACCA    3480

GCCACCACGG GCGATGGCGG CCACAGCGGT CTGCCTCCCA ACCCGGTCAT TGTCATCTCA    3540

GATGCCGGCG ATGGTCACAG AGGCACAGAA GTGACCCCTG AGACGTTCAC AGCTGGCTCC    3600

CAGGGTTCAT ACCGAGACTC TGCGTACTTC TCAGACAATG ACTCTGAGCC CGAGAAAAGG    3660

TCTGAGGAGG TCCCGGGAAC CTCCCCATCC GCCTTGGTGT TGGTACAGGA GCAGCCCCTA    3720

CCCGAGCCAG TCCTCCCCGA GCAAAGTCCT GCTGCCCAGG ATAGCTGCCT GGAAGCCAGA    3780

AAGAGCCAGC CAGATGAAAG TTGTCTGTCT GCTTTGCACA ACTCCAGTGA CCTGGAATTA    3840

AGAGCCACGC CGGAGCCAGC ACAGACTGGT GTTCCCCAGC AGGTGCATCC CACGGAAGAC    3900

GAGGCCAGCA GTCCCTGGAG TGTGCTGAAT GCAGAACTTA GCAGCGGCGA TGACTTCGAG    3960

ACACAGGACG ATCGCCCCTG CACCCTCGCT TCCACGGGGA CCAACACGAA CGAACTCCTT    4020

GCCTACACCA ATTCTGCGCT GGACAAGTCC CTGTCCAGCC ACTCCGAGGG CCCGAAGTTG    4080

AAGGAGCCGG ACATCGAAGG GAAGTACCTG GGGAAACTCG GGGTGTCAGG GATGCTCGAC    4140

CTCTCAGAGG ACGGGATGGA TGCAGACGAG GAGGACGAAA CAGCGACGA CTCGGACGAG    4200

GACCTGCGGG CCTTCAACCT GCATAGCCTC AGCTCCGAGT CGGAGGACGA GACCGAGCAC    4260

CCCGTGCCCA TCATCCTCAG CAACGAGGAC GGAAGGCACC TGCGGAGTCT GTTGAAGCCC    4320

ACAGCGGCCA ATGCCCCCGA CCCACTGCCC GAGGACTGGA AGAAGGAAAA GAAGGCAGTC    4380

ACGTTTTTCG ATGATGTCAC AGTCTACCTG TTTGACCAGG AGACCCCAAC CAAAGAGCTG    4440

GGGCCCTGTG GAGGAGAGGC GTGCGGCCCG GACCTGAGCG GCCCAGCCCC AGCCTCAGGC    4500

TCTCCCTACC TGAGCAGGTG CATCAACTCC GAAAGCTCCA CCGACGAAGA AGGTGGTGGC    4560

TTTGAGTGGG ATGATGACTT CTCCCCAGAT CCTTTTATGT CAAAGACAAC AAGTAACCTG    4620

CTCAGCTCCA AGCTTCTCT CCAAACATCC AAGTACTTTT CTCCGCCGCC ACCGGCCCGG    4680

AGCACGGAGC AGAGCTGGCC GCACTCGGCG CCTTACTCCC GGTTCTCCAT CTCTCCCGCC    4740

AACATTGCCA GCTTTTCCCT CACACACCTG ACCGACTCGG ACATCGAGCA GGGCGGAAGC    4800

AGCGAAGACG GAGAAAAGGA CTAGGTGGCT GCCAACGCGC ACGCTCGGGT CCGAGGCTGC    4860

TCCCCTGGAG CGGCGCCCCT GCGCCCTCAG CCCGAGCAGC GACATCCACT CGCCATTTGC    4920

TGACATGAGA TTGGGAGGAA GAATCCAGAG GTGAAGAGGG AGACGGCTCT TAGCTGCGTT    4980

CAAGGCGGGG CCCTCGGGAG CCCAGGTGCA GAGCGAGGCC GTGTCCAGGA GCCGGCGTCC    5040

CTCAGTGCCC CGTGCACCCG CGGCCGCGGC CTCCCAGGCA GTGCTCATGC GCTGGCCGTC    5100

GGGGGAGGCA GGGGCACAGC CTCCATGTGC GCGCGCGTGT GGAGCTGTGT GCACCGCATG    5160

TGTGCTTTCC ACAGGGGCGT CTCTGCGTCC ACGCCTGCAC ATCCCGGCGC ACGTGTGGGC    5220

ACCACAGAGG ACACGTGAGG GGAATGGTCA CCAGTGAGCC ATATTTATTA TTTCTAGAGA    5280

AATCACGAAC TGCTTTCTGT AATTGCACTG TGGATAAATG TTCCGAGAGT CTCCATTGTT    5340

GTACAGGATC TTCAGTTATT CGAGGGGAAT GAGGCAGGTC AAGCCGATGC TAGCCACTAG    5400

TTTGATTTTT TTTCTGTTTT ATAGTTTGCG CTGCATGGTA CTTGTGAAGC TTAAATATTT    5460

TGAGTGTTCT ACTGTGTCTA GGATTGTTGG GATTGTACAT ATGGTACTCT TTCATAAATG    5520

ATAAATGATT CTGAATGTTA GTGTTTTATG TTCATATAGG AAATATTTTC ATTGAGTCCA    5580

AAATACCACT GTTTTGTTGA TGGACTTGAA TGCATTTTTG TCTCTTCTTG ATGAAGCGGC    5640

TTTGCCGCAG CAAATGAGGC TTCTCTCTGA GGAGCTGAGA GGTCTTGCAG CCTCTCCTTG    5700

TCATTCTCCC ACCCCACATC CCATTTTTTA AAGCCCTTTT GGTAAAAACC AACAGGTTGT    5760
```

-continued

```
GGCCGCAGAC CTCAGATGGA CCCGGCCCAT CCCTGGGGAC GTGCTGGCGT GGCAGGTCCA    5820

GAGAGCTGCA CCCTGCACGG GGCACCGCAC CGCTTCCCTC CGCGCAGCTC TTCTGCCTGG    5880

TTTTCGGAGG CCAGGCTGCT GGGAGGCTTC CGTGTTCCTG TCAGTCCTTC CTTCAAGAAG    5940

CCGGGGAACT CAGGCAGACT CATCTCCGCA GAGCATACCA GCCGTGGGGG ACCGTTCGAC    6000

TTGATGATGT GTGCACACTT CAGGTGGTGG GGACTTGAGC TTTAAAAAAA CCTCCACAGC    6060

CGAATCTTCT CCTCCGAGCC ACTCCACGTC ACGTCCAGCT GGGCCTGGCC AGTCTGTGGT    6120

TATCCATGTG GGATGAGATA ACACCACATC CTGCAGCTGT GAAGGGGAT GGACAAGGGA     6180

CGACGGCCGA CGGCAGAGCA TCAGCAGCCG ACACATAGTT CGGGTCGGGG CCTTGGGTGG    6240

TCCTGCATGG CCCGGGACTC ATCTCACGGA CCCTCCGTTC TGCATTAAGC CCCAGGTTCT    6300

CTTCTGGCTT TGAAAGGGCC CGAGTGCTCC CAGTGTAGCT TCGTCACATC GTCACGAGCC    6360

CCTGTGGTCA TGGGCGACCT CACACCTCCC TCCCTGAGTT CTGCTCTGAC ATAAGGAAGT    6420

CCTCGGTGGC TGGTGCAGCG CGGCTGTGCT GTGCTGGGA GGCAGCCGTT CCTTCGGGGG     6480

TCCTTGGGCC TGCAGTCCCC TCATACTCAC CCTTCACCCA ACATATTTTC CGGTGCTGAT    6540

ATGTTTCCAG ACTCCAGCGC AACCTGGGGT GCTCTCCAGA CCCGTGCAGG GGCCGCCTGG    6600

GGTACACGGA AGGAAGTTGA GTCCTAGTGC AAAATGCAGG CGGACGTTGC CAGAGAGTGC    6660

GCAGCAAATG ACCTTCATTG CCAGTTCCAC CCTACTCCTC TCATTTTTTA TACTAAGCAA    6720

TAACTTTCCA AAGCAAGAAG TTCAGGATGG AGAGAGTCCC CTCCTGTGTA GGCATGGGGT    6780

GGACGCGGTG CCCACCTGGG CTATGTGGGG AGCACCACTG TCTCGGGATG CGCGAATTTT    6840

TTTTTTTTTT TAATTAACAG GGCATTAGAA GATGATTTTG CCAAAATTGT CATGACTCTG    6900

AATTCTTGCT GTGGGACTT CCTGAGTTTT CTCAGTTTTT ACATCTAAGA TTAGTCTTGG     6960

CTGAAGAGAA ATGAGACGTG ATTATACTAC TTTTTCAATT GCAGGTTTAA GGAGTTCAGA    7020

TTTAATGACC AAAGTCATAC AGATCATGGA ATCTGTCGTC GTCTTATACA GTGTCAGCCT    7080

CGAGTACATT TATTAACCTT TTGGGGCTGT CAGTTTTCCA CTAGGATTAA GATTTTGGCC    7140

GGGCGCGGTG GCTCACGCCT GCAATCCCAA CACATTGGGG GGTCGAGGCG GACGGATCAC    7200

TTTGAGCCCA GGAGTTCAAG ACCAGCCTGG GCAACATGGC GAAACCTCGT CTCTACTAAA    7260

AATACAAAAT ATATATATAT ATATATACTA GCTGGGGCAC ATAGTGGTGT GCACCTGTAG    7320

TCCCAGCTGC TTGGGAGGCT GAGGTGGGAG GATGGCTAGA GCCCAGGAGA TGGGTGTTGC    7380

AGTGAGCTGA GACCATGCCA CTGTACTCTA GCCTGGGTAA CAGCCAGACC CTGTCTCAAA    7440

AAAAAAACAA TTTTTTTCAT AACATAATTC CCATTTTTAT TTATTTTGAG TCACTCATAA    7500

TTAATTGCCA AAAAGCATT TTATACATTG AGTTGGGGGG TAGTGGATCT TAGTGTGGTG     7560

TTGCATGGAG GGGCGAGATT TTATATTTAT AATCAACACG TGGGTTAACA TGTTTTTTTG    7620

AAATCCAAGC AATACACAGG AAATTTAAGT AGAATAAAAA TTGCAGCCCA TTTTTGAAAT    7680

GTCAGCATGT GCTGTGTTCA GTTCAGGTTT TTGTTGTTTG TTTTGTTATT TTTTAACTAA    7740

TAAGTTGGTT ATCAGTGGTG GGTTTTCAAA ATGTACTTGT TCTAATAAGT TGTACAATGA    7800

ACTAAATCAG TGGCATTCTC TAGATAATGT GGGGGAAGGT TAGAATATTT CTGGCCTTC     7860

TATGGGTAG CAACCCAGAA TCAATCTGAA TTAGTCCTGT TTTGGTGGAG TTTGTACATT     7920

TTAAATCCTA TAACAAAAAT AATCTAGTTT TCATTTCCTT ACTAGCTAGA TGCGAATTTG    7980

TCTTTTTGAA TGACCCTGTC AATAAGCCAG AAAGGGCAAC CCAGAAAAAG TGCTCCCCAC    8040

ATCCTTCTGA GACTTGGCCT GTGTGTGTGG ACGAGAAGCC ATTCACCGTA AGGGTGCAGA    8100
```

-continued

```
AAGCTCGACC AAGCCGAATT GCAAACAACG TTCGTTCTAT TTTTAAATGT ACAGGTTCGA    8160

TCGTTTCTAT AGAAATGGGT TTATCTAAGA AAAGTCTTGG TTTGTCTTGC TGCTGTAAAA    8220

GGCCTTTCCA AACCCCTCCT TTTATTCCTG TTTCCCGAAA TAAGGTATTT GTAGAGTTAA    8280

GGACCTACTG CATGCCTGTC CCCAGGGCCC CGGTGGAAGG AAGGCAGCGC CTGCTCTTCC    8340

TTGACTCAGC CCATCATCTG AAAATTCAGA AGTGAACCAA GGGTTAGACG CCAGAGGTTG    8400

GGCTTCTGTT AGAGTGGCTT CAAAACATGA GCCTTATGGG AAGTAGCCTT AAAAAAAGAA    8460

TGGGTATACG CAGTGACTTC CGATGAAAT CTCCAAAACA ATATTCCTAA GTAGCAATGG     8520

GGTTGGCTCA AGTCTTTATT AACAAAGAAC ATTCTCTTTC ATCTATAAAG AAATTCTTAA    8580

AGATGCATTG ACAGTGTTGA ATTACCAACA GCCTGTGAAG ATCAGTTTGA CCGGTGTGGA    8640

CACGTGCTGG TTAAGCACTC AGGCCTACGT GGGCCGAGCG GGATCTTGAT CATGGGGCTG    8700

GTGTATGGAT CCACCGTCGG ATTCCGTCTG CAGAGGAGGA CGTAGGGGGC CGTCACACCC    8760

ACCAGGCCTC CCTGCTGTGC TTTAACACAG GCAGAAGAGG TTCATGGCAA TATAATAGTC    8820

AATGAACTTT CAGTTTAAAT TGTGTACATT TTTAAATTGT AAGATTTTTA CTGTATATTG    8880

ATGCATAGTG TGATTCAATA AATTGCTTGT AATTTAAAAA CTATTTAATA TTCAAAATAA    8940

ATATAGTTAT ATATTTATAA AAAAAAAAAA AAAAACTCG AG                       8982

(2) INFORMATION FOR SEQ ID NO: 6:

(i) SEQUENCE CHARACTERISTICS:
        (A) LENGTH:        245 base pairs
        (B) TYPE:          nucleic acid
        (C) STRANDEDNESS:  single
        (D) TOPOLOGY:      linear (xi) SEQUENCE DESCRIPTION: SEQ ID NO: 6:

GATGGCCACG GCTGGTTTGG CAAGGTTTTC CTGGGAGAGA CTTACACAGG CACCAGCGTC     60

GCGAGAGTCA TAGTGAAGGA GTTAAAAGTC AGTGCAAGCC CCAAGGAGCA GGACACTTTC    120

CTGAAGAGTG GAGAGCCTTA CTACATCCTC CAGCATCCAA ATGTCCTCCA GTGTGTGGGG    180

CAGTGTGTGG AAGCCATCCC CTACCTTCTG GTGTTTGAAT TTTGCCCATT TGGCGACCTG    240

AAATC                                                                245

(2) INFORMATION FOR SEQ ID NO: 7:

(i) SEQUENCE CHARACTERISTICS:
        (A) LENGTH:        828 base pairs
        (B) TYPE:          nucleic acid
        (C) STRANDEDNESS:  single
        (D) TOPOLOGY:      linear (xi) SEQUENCE DESCRIPTION: SEQ ID NO: 7:

GATGAGATCG GGTTTAAAGA GTTCGAGAAT CCGGAAGGGG AGGACTGCTC TGGGGAGTAC     60

ACCCCCCCTG CGGAGGAGAC CTCCTCCTCA CAGTCGCTGC CTGATGTCTA TATTCTGCCG    120

CTGGCAGAGG TCTCACTGCC AATGCCTGCC CCGCAGCCTG CACACTCAGA CATCAGCACC    180

CCCCTGGGCC TGAGCCGCCA GCACCTCAGC TACCTGCAGG AGATTGGCAG CGGCTGGTTT    240

GGGAAGGTGA TCCTCGGGGA GGTTTTCTCA GACTACTCGC CAGCGCAGGT GGTGGTGAAG    300

GAACTCCGGG CTAGTGCAGG GCCCCTGGAG CAGCGCAAGT TCATCTCAGA GGCTCAGCCC    360

TACAGGAGCC TGCAGCATCC CAACGTCCTC CAGTGCCTGG GTGTCTGTGT GGAGACCTTG    420

CCCTTCCTGT TGATCATGGA GTTCTGCCAG CTGGGGGACC TGAAGCGATA CCTTCGGGCC    480

CAGCGGCCAC CTGAAGGCAT GTCCCCTGAA CTTCCCCCAC GAGACCTTCG GACATTACAG    540
```

```
AGGATGGGCC TAGAGATTGC CCGAGGACTG GCACACCTGC ACTCCCACAA CTACGTGCAC      600

AGCGATCTGG CGCTGCGCAA CTGCCTGCTA ACTTCAGACC TGACTGTGCG TATTGGAGAC      660

TATGGGCTGG CGCATAGCAA CTACAAGGAA GACTACTACC TGACACCCGA GCGCCTATGG      720

GTGCCGCTGC GCTGGGCAGC GCCCGAGCTG CTGGGCGAGC TGCACGGCAG CTTTGTGCTA      780

GTGGATCAAA GCCGTGAGAG TAACATCTGG ACCCTAGGGG TGACAATC                   828

(2) INFORMATION FOR SEQ ID NO: 8:

(i) SEQUENCE CHARACTERISTICS:
        (A) LENGTH:        1583 base pairs
        (B) TYPE:          nucleic acid
        (C) STRANDEDNESS:  single
        (D) TOPOLOGY:      linear (xi) SEQUENCE DESCRIPTION: SEQ ID NO: 8:

GAATTCCGGG GCTGGGTCGC CTGCGCCGAG TGTTGCTGAG GCTGCGTCTT GGGTGCGCAG       60

CTCCGGCCCA GCCTCACCCA GGGGAACGCC TCGCAGGTGC TCACGGACGA TGGAGAGCCG      120

CCACCACCTC CACCTCCCTG CCATCCTCGA CAAGATGCCT GCCCCGGCG CCCTCATCCT      180

CCTTGCGGCC GTCTCCGCCT CCGGCTGCCT GGCGTCCCCG GCCCACCCCG ATGGATTCGC      240

CCTGGGCCGG GCTCCTCTGG CTCCTCCCTA CGCTGTGGTC CTCATTTCCT GCTCCGGCCT      300

GCTGGCCTTC ATCTTCCTCC TCCTCACCTG TCTGTGCTGC AAACGGGGCG ATGTCGGCTT      360

CAAGGAATTT GAGAACCCTG AAGGGGAGGA CTGCTCCGGG GAGTACACTC CCCCTGCGGA      420

GGAGACCTCC TCCTCACAGT CGCTGCCTGA TGTCTACATT CTCCCGCTGG CTGAGGTCTC      480

CCTGCCAATG CCTGCCCCGC AGCCTTCACA CTCAGACATG ACCACCCCCC TGGGCCTTAG      540

CCGGCAGCAC CTGAGCTACC TGCAGGAGAT TGGGAGTGGC TGGTTTGGGA AGGTGATCCT      600

GGGAGAGATT TTCTCCGACT ACACCCCGC CCAGGTGGTG GTGAAGGAGC TCCGAGCCAG      660

CGCGGGGCCC CTGGAGCAAC GCAAGTTCAT CTCGGAAGCA CAGCCGTACA GGAGCCTGCA      720

GCACCCCAAT GTCCTCCAGT GCCTGGGTCT GTGCGTGGAG ACGCTGCCGT TTCTGCTGAT      780

TATGGAGTTC TGTCAACTGG GGGACCTGAA GCGTTACCTC CGAGCCCAGC GGCCCCCCGA      840

GGGCCTGTCC CCTGAGCTAC CCCCTCGAGA CCTGCGGACG CTGCAGAGGA TGGGCCTGGA      900

GATCGCCCGC GGGCTGGCGC ACCTGCATTC CCACAACTAC GTGCACAGCG ACCTGGCCCT      960

GCGCAACTGC CTGCTGACCT CTGACCTGAC CGTGCGCATC GGAGACTACG GCTGGCCCA     1020

CAGCAACTAC AAGGAGGACT ACTACCTGAC CCCAGAGCGC CTGTGGATCC CACTGCGCTG     1080

GGCGGCGCCC GAGCTCCTCG GGGAGCTCCA CGGGACCTTC ATGGTGATGG ACCAGAGCCG     1140

CGAGAGCAAC ATCTGGTCCC TGGGGGTGAC CCTGTGGGAG CTGTTTGAGT TTGGGGCCCA     1200

GCCCTACCGC CACCTGTCAG ACGAGGAGGT CCTCGCCTTC GTGGTCCGCC AGCAGCATGT     1260

GAAGCTGGCC CGGCCGAAGC TCAAGCTGCC TTACGCGGAC TACTGGTATG ACATTCTTCA     1320

GTCCTGCTGG CGGCCACCTG CCCAGCGCCC TTCAGCCTCT GATCTCCAAT GCAGCTCAC     1380

CTACTTGCTC TCCGAGCGGC CTCCCCGGCC CCCACCGCCG CCACCCCCAC CCCGAGACGG     1440

TCCCTTCCCC TGGCCCTGGC CCCCTGCACA CAGTGCGCCC CGCCCGGGGA CCCTCTCCTC     1500

ACCGTTCCCC CTACTGGATG GCTTCCCTGG AGCCGACCCC GACGATGTGC TCACGGTCAC     1560

CGAGAGTAGC CGCGCCGGAA TTC                                            1583

(2) INFORMATION FOR SEQ ID NO: 9:
```

(i) SEQUENCE CHARACTERISTICS:
    (A) LENGTH:         828 base pairs
    (B) TYPE:           nucleic acid
    (C) STRANDEDNESS:   single
    (D) TOPOLOGY:       linear (xi) SEQUENCE DESCRIPTION: SEQ ID NO: 9:

```
GATGAGATCG GGTTTAAAGA GTTCGAGAAT CCGGAAGGGG AGGACTGCTC TGGGGAGTAC      60
ACCCCCCCTG CGGAGGAGAC CTCCTCCTCA CAGTCGCTGC CTGATGTCTA TATTCTGCCG     120
CTGGCAGAGG TCTCACTGCC AATGCCTGCC CCGCAGCCTG CACACTCAGA CATCAGCACC     180
CCCCTGGGCC TGAGCCGCCA GCACCTCAGC TACCTGCAGG AGATTGGCAG CGGCTGGTTT     240
GGGAAGGTGA TCCTCGGGGA GGTTTTCTCA GACTACTCGC CAGCGCAGGT GGTGGTGAAG     300
GAACTCCGGG CTAGTGCAGG GCCCCTGGAG CAGCGCAAGT TCATCTCAGA GGCTCAGCCC     360
TACAGGAGCC TGCAGCATCC CAACGTCCTC CAGTGCCTGG GTGTCTGTGT GGAGACCTTG     420
CCCTTCCTGT TGATCATGGA GTTCTGCCAG CTGGGGGACC TGAAGCGATA CCTTCGGGCC     480
CAGCGGCCAC CTGAAGGCAT GTCCCCTGAA CTTCCCCCAC GAGACCTTCG GACATTACAG     540
AGGATGGGCC TAGAGATTGC CCGAGGACTG GCACACCTGC ACTCCCACAA CTACGTGCAC     600
AGCGATCTGG CGCTGCGCAA CTGCCTGCTA ACTTCAGACC TGACTGTGCG TATTGGAGAC     660
TATGGGCTGG CGCATAGCAA CTACAAGGAA GACTACTACC TGACACCCGA GCGCCTATGG     720
GTGCCGCTGC GCTGGGCAGC GCCCGAGCTG CTGGGCGAGC TGCACGGCAG CTTTGTGCTA     780
GTGGATCAAA GCCGTGAGAG TAACATCTGG ACCCTAGGGG TGACAATC                  828
```

(2) INFORMATION FOR SEQ ID NO: 10:

(i) SEQUENCE CHARACTERISTICS:
    (A) LENGTH:         848 amino acids
    (B) TYPE:           amino acid
    (C) STRANDEDNESS:   single
    (D) TOPOLOGY:       linear (ii) MOLECULE TYPE:     Protein (xi) SEQUENCE DESCRIPTION: SEQ ID NO: 10:

```
Met Pro Ile Ala Leu Leu Ala Leu Ala Met Ser Ser Ser Phe Phe Asn
1               5                   10                  15

Pro Ser Phe Ala Phe Ser Ser His Phe Asp Pro Asp Gly Ala Pro Leu
            20                  25                  30

Ser Glu Leu Ser Trp Ser Ser Ser Leu Ala Val Val Ala Val Ser Phe
        35                  40                  45

Ser Gly Ile Phe Thr Val Ile Val Leu Met Leu Ala Cys Leu Cys Cys
    50                  55                  60

Lys Lys Gly Gly Ile Gly Phe Lys Glu Phe Glu Asn Ala Glu Gly Glu
65                  70                  75                  80

Glu Tyr Val Ala Asp Phe Ser Glu Gln Gly Ser Pro Ala Ala Thr Val
                85                  90                  95

Gln Asn Gly Pro Asp Val Tyr Val Leu Pro Leu Thr Glu Val Ser Leu
            100                 105                 110

Pro Met Ala Lys Gln Pro Gly Arg Ser Val Gln Leu Leu Lys Ser Thr
        115                 120                 125

Asp Leu Gly Arg His Ser Leu Leu Tyr Leu Lys Glu Ile Gly His Gly
    130                 135                 140

Trp Phe Gly Lys Val Phe Leu Gly Glu Val His Ser Gly Val Ser Gly
145                 150                 155                 160
```

```
Thr Gln Val Val Lys Glu Leu Lys Ala Ser Ala Val Gln Glu
            165                 170                 175

Gln Met Gln Phe Leu Glu Glu Ala Gln Pro Tyr Arg Ala Leu Gln His
            180                 185                 190

Ser Asn Leu Leu Gln Cys Leu Ala Gln Cys Ala Glu Val Thr Pro Tyr
            195                 200                 205

Leu Leu Val Met Glu Phe Cys Pro Leu Gly Asp Leu Lys Gly Tyr Leu
            210                 215                 220

Arg Ser Cys Arg Val Thr Glu Ser Met Ala Pro Asp Pro Leu Thr Leu
225                 230                 235                 240

Gln Arg Met Ala Cys Glu Val Ala Cys Gly Val Leu His Leu His Arg
                245                 250                 255

His Asn Tyr Val His Ser Asp Leu Ala Leu Arg Asn Cys Leu Leu Thr
            260                 265                 270

Ala Asp Leu Thr Val Lys Val Gly Asp Tyr Gly Leu Ala His Cys Lys
            275                 280                 285

Tyr Arg Glu Asp Tyr Leu Val Thr Ala Asp Gln Leu Trp Val Pro Leu
            290                 295                 300

Arg Trp Ile Ala Pro Glu Leu Val Asp Glu Val His Gly Asn Leu Leu
305                 310                 315                 320

Val Val Asp Gln Thr Lys Thr Ser Asn Val Trp Ser Leu Gly Val Thr
                325                 330                 335

Ile Trp Glu Leu Phe Glu Leu Gly Ala Gln Pro Tyr Pro Gln His Ser
            340                 345                 350

Asp Arg Gln Val Leu Ala Tyr Ala Val Arg Glu Gln Gln Leu Lys Leu
            355                 360                 365

Pro Lys Pro Gln Leu Gln Leu Thr Leu Ser Asp Arg Trp Tyr Glu Val
            370                 375                 380

Met Gln Phe Cys Trp Leu Gln Pro Glu Gln Arg Pro Thr Ala Glu Glu
385                 390                 395                 400

Val His Leu Leu Leu Ser Tyr Leu Cys Ala Lys Gly Thr Thr Glu Leu
                405                 410                 415

Glu Glu Glu Phe Glu Arg Arg Trp Arg Ser Leu Arg Pro Gly Gly Ser
            420                 425                 430

Ala Gly Leu Gly Ser Ala Ser Thr Val Pro Ala Ala Ala Ser Glu
            435                 440                 445

Leu Thr Ala Ala Ser Ser Phe Pro Leu Leu Glu Gln Phe Thr Ser Asp
            450                 455                 460

Gly Phe His Val Asp Ser Asp Val Leu Thr Val Thr Glu Thr Ser
465                 470                 475                 480

His Gly Leu Asn Phe Glu Tyr Lys Trp Glu Ala Gly Cys Gly Ala Glu
                485                 490                 495

Ala Tyr Pro Pro Pro Gly Ala Ala Phe Ser Pro Gly Ser Ala Gly Arg
            500                 505                 510

Leu Gln Glu Leu Cys Ala Pro Asp Ser Ser Pro Gly Val Val Pro
            515                 520                 525

Val Leu Ser Ala His Ser Pro Ser Val Gly Ser Glu Tyr Phe Ile Arg
            530                 535                 540

Leu Glu Gly Ala Val Pro Ala Ala Gly His Asp Pro Asp Cys Ala Gly
545                 550                 555                 560

Cys Ala Pro Ser Pro Gln Ala Val Ser Glu Gln Asp Asn Asn Ser Glu
                565                 570                 575

Glu Ser Thr Ala Ala Ser Leu Val Met Glu Pro Leu Leu Gly His Ala
```

-continued

```
                580                 585                 590
Pro Pro Thr Gly Gly Leu Trp Gly Pro Cys Asp His His Ser Arg Arg
            595                 600                 605

Arg Gln Glu Pro Pro Cys Pro Ser Arg Ser Pro Ser Pro Gly Thr Pro
610                 615                 620

Met Leu Pro Ala Glu Asp Ile Asp Trp Gly Val Ala Thr Phe Cys Pro
625                 630                 635                 640

Pro Phe Phe Asp Asp Pro Leu Gly Thr Ser Pro Ser Gly Ser Pro Gly
                645                 650                 655

Ala Gln Pro Ser Pro Ser Asp Glu Glu Leu Glu Gly Lys Thr Gly
            660                 665                 670

Arg Ala Ala Gln Cys Gly His Trp Ser Ser Asn Met Ser Ala Asn Asn
            675                 680                 685

Asn Ser Gly Ser Arg Asp Pro Glu Ser Trp Asp Pro Gly Tyr Val Ser
690                 695                 700

Ser Phe Thr Asp Ser Tyr Arg Asp Asp Cys Ser Ser Leu Glu Gln Thr
705                 710                 715                 720

Pro Arg Ala Ser Pro Glu Leu Gly His Pro Leu Ser Gln Glu Asp Ser
                725                 730                 735

Arg Asp Phe Leu Pro Gly Leu Val Ala Ala Ser Pro Gly Gln Glu Ser
            740                 745                 750

Ser Arg Cys Phe Asn Leu Leu Pro Leu Cys Pro Ala Lys Gly Leu Ala
            755                 760                 765

Pro Ala Ala Cys Leu Val Pro Pro Trp Thr Glu Ala Ala Val Gly
            770                 775                 780

Gly Ala Glu Asn Pro Ile Val Glu Pro Lys Leu Ala Gln Glu Ala Glu
785                 790                 795                 800

Gly Ser Ala Glu Pro Gln Leu Pro Leu Pro Ser Val Pro Ser Pro Ser
                805                 810                 815

His Glu Gly Ala Ser Leu Pro Ser Glu Glu Ala Ser Ala Pro Asp Ile
            820                 825                 830

Gln Pro Ala Ser Pro Thr Pro Ala Ala Gly Ser Trp Val Thr Val Leu
            835                 840                 845

(2) INFORMATION FOR SEQ ID NO: 11:

(i) SEQUENCE CHARACTERISTICS:
        (A) LENGTH:         1384 amino acids
        (B) TYPE:           amino acid
        (C) STRANDEDNESS:   single
        (D) TOPOLOGY:       linear (ii) MOLECULE TYPE:         Protein (xi) SEQUENCE DESCRIPTION: SEQ ID NO: 11:

Met Pro Ile Ala Leu Leu Ala Leu Ala Met Ser Ser Ser Phe Phe Asn
1               5                   10                  15

Pro Ser Phe Ala Phe Ser Ser His Phe Asp Pro Asp Gly Ala Pro Leu
                20                  25                  30

Ser Glu Leu Ser Trp Ala Ser Ser Leu Ala Val Val Ala Val Ser Phe
            35                  40                  45

Ser Gly Leu Phe Ala Val Ile Val Leu Met Leu Ala Cys Leu Cys Cys
            50                  55                  60

Lys Lys Gly Gly Ile Gly Phe Lys Glu Phe Glu Asn Ala Glu Gly Glu
65                  70                  75                  80

Glu Tyr Val Ala Asp Phe Ser Glu Gln Gly Ser Pro Ala Ala Thr Val
```

-continued

```
                85                  90                  95
Gln Asn Gly Pro Asp Val Tyr Val Leu Pro Leu Thr Glu Val Ser Leu
            100                 105                 110

Pro Met Ala Lys Gln Pro Gly Arg Ser Val Gln Leu Leu Lys Ser Thr
            115                 120                 125

Asp Val Gly Arg His Ser Leu Leu Tyr Leu Lys Glu Ile Gly Arg Gly
130                 135                 140

Trp Phe Gly Lys Val Phe Leu Gly Glu Val Asn Ser Gly Ile Ser Ser
145                 150                 155                 160

Ala Gln Val Val Lys Glu Leu Gln Ala Ser Val Gln Glu
            165                 170                 175

Gln Met Gln Phe Leu Glu Glu Val Gln Pro Tyr Arg Ala Leu Lys His
            180                 185                 190

Ser Asn Leu Leu Gln Cys Leu Ala Gln Cys Ala Glu Val Thr Pro Tyr
            195                 200                 205

Leu Leu Val Met Glu Phe Cys Pro Leu Gly Asp Leu Lys Gly Tyr Leu
            210                 215                 220

Arg Ser Cys Arg Val Ala Glu Ser Met Ala Pro Asp Pro Arg Thr Leu
225                 230                 235                 240

Gln Arg Met Ala Cys Glu Val Ala Cys Gly Val Leu His Leu His Arg
            245                 250                 255

Asn Asn Phe Val His Ser Asp Leu Ala Leu Arg Asn Cys Leu Leu Thr
            260                 265                 270

Ala Asp Leu Thr Val Lys Ile Gly Asp Tyr Gly Leu Ala His Cys Lys
            275                 280                 285

Tyr Arg Glu Asp Tyr Phe Val Thr Ala Asp Gln Leu Trp Val Pro Leu
            290                 295                 300

Arg Trp Ile Ala Pro Glu Leu Val Asp Glu Val His Ser Asn Leu Leu
305                 310                 315                 320

Val Val Asp Gln Thr Lys Ser Gly Asn Val Trp Ser Leu Gly Val Thr
            325                 330                 335

Ile Trp Glu Leu Phe Glu Leu Gly Thr Gln Pro Tyr Pro Gln His Ser
            340                 345                 350

Asp Gln Gln Val Leu Ala Tyr Thr Val Arg Glu Gln Gln Leu Lys Leu
            355                 360                 365

Pro Lys Pro Gln Leu Gln Leu Thr Leu Ser Asp Arg Trp Tyr Glu Val
370                 375                 380

Met Gln Phe Cys Trp Leu Gln Pro Glu Gln Arg Pro Thr Ala Glu Glu
385                 390                 395                 400

Val His Leu Leu Leu Ser Tyr Leu Cys Ala Lys Gly Ala Thr Glu Ala
            405                 410                 415

Glu Glu Glu Phe Glu Arg Arg Trp Arg Ser Leu Arg Pro Gly Gly Gly
            420                 425                 430

Gly Val Gly Pro Gly Pro Gly Ala Ala Gly Pro Met Leu Gly Gly Val
            435                 440                 445

Val Glu Leu Ala Ala Ala Ser Ser Phe Pro Leu Leu Glu Gln Phe Ala
            450                 455                 460

Gly Asp Gly Phe His Ala Asp Gly Asp Val Leu Thr Val Thr Glu
465                 470                 475                 480

Thr Ser Arg Gly Leu Asn Phe Glu Tyr Lys Trp Glu Ala Gly Arg Gly
            485                 490                 495

Ala Glu Ala Phe Pro Ala Thr Leu Ser Pro Gly Arg Thr Ala Arg Leu
            500                 505                 510
```

-continued

```
Gln Glu Leu Cys Ala Pro Asp Gly Ala Pro Pro Gly Val Val Pro Val
        515                 520                 525
Leu Ser Ala His Ser Pro Ser Leu Gly Ser Glu Tyr Phe Ile Arg Leu
        530                 535                 540
Glu Glu Ala Ala Pro Ala Ala Gly His Asp Pro Asp Cys Ala Gly Cys
545                 550                 555                 560
Ala Pro Ser Pro Pro Ala Thr Ala Asp Gln Asp Asp Ser Asp Gly
                565                 570                 575
Ser Thr Ala Ala Ser Leu Ala Met Glu Pro Leu Leu Gly His Gly Pro
            580                 585                 590
Pro Val Asp Val Pro Trp Gly Arg Gly Asp His Tyr Pro Arg Arg Ser
            595                 600                 605
Leu Ala Arg Asp Pro Leu Cys Pro Ser Arg Ser Pro Ser Pro Ser Ala
            610                 615                 620
Gly Pro Leu Ser Leu Ala Glu Gly Gly Ala Glu Asp Ala Asp Trp Gly
625                 630                 635                 640
Val Ala Ala Phe Cys Pro Ala Phe Phe Glu Asp Pro Leu Gly Thr Ser
                645                 650                 655
Pro Leu Gly Ser Ser Gly Ala Pro Pro Leu Pro Leu Thr Gly Glu Asp
                660                 665                 670
Glu Leu Glu Glu Val Gly Ala Arg Arg Ala Ala Gln Arg Gly His Trp
            675                 680                 685
Arg Ser Asn Val Ser Ala Asn Asn Asn Ser Gly Ser Arg Cys Pro Glu
            690                 695                 700
Ser Trp Asp Pro Val Ser Ala Gly Cys His Ala Glu Gly Cys Pro Ser
705                 710                 715                 720
Pro Lys Gln Thr Pro Arg Ala Ser Pro Glu Pro Gly Tyr Pro Gly Glu
                725                 730                 735
Pro Leu Leu Gly Leu Gln Ala Ala Ser Ala Gln Glu Pro Gly Cys Cys
                740                 745                 750
Pro Gly Leu Pro His Leu Cys Ser Ala Gln Gly Leu Ala Pro Ala Pro
            755                 760                 765
Cys Leu Val Thr Pro Ser Trp Thr Glu Thr Ala Ser Ser Gly Gly Asp
770                 775                 780
His Pro Gln Ala Glu Pro Lys Leu Ala Thr Glu Ala Glu Gly Thr Thr
785                 790                 795                 800
Gly Pro Arg Leu Pro Leu Pro Ser Val Pro Ser Pro Ser Gln Glu Gly
                805                 810                 815
Ala Pro Leu Pro Ser Glu Glu Ser Ala Pro Asp Ala Pro Asp Ala
                820                 825                 830
Leu Pro Asp Ser Pro Thr Pro Ala Thr Gly Gly Glu Val Ser Ala Ile
            835                 840                 845
Lys Leu Ala Ser Ala Leu Asn Gly Ser Ser Ser Pro Glu Val Glu
        850                 855                 860
Ala Pro Ser Ser Glu Asp Glu Asp Thr Ala Glu Ala Thr Ser Gly Ile
865                 870                 875                 880
Phe Thr Asp Thr Ser Ser Asp Gly Leu Gln Ala Arg Arg Pro Asp Val
                885                 890                 895
Val Pro Ala Phe Arg Ser Leu Gln Lys Gln Val Gly Thr Pro Asp Ser
            900                 905                 910
Leu Asp Ser Leu Asp Ile Pro Ser Ser Ala Ser Asp Gly Gly Tyr Glu
        915                 920                 925
```

```
Val Phe Ser Pro Ser Ala Thr Gly Pro Ser Gly Gln Pro Arg Ala
    930                 935                 940

Leu Asp Ser Gly Tyr Asp Thr Glu Asn Tyr Glu Ser Pro Glu Phe Val
945                 950                 955                 960

Leu Lys Glu Ala Gln Glu Gly Cys Glu Pro Gln Ala Phe Ala Glu Leu
                965                 970                 975

Ala Ser Glu Gly Glu Gly Pro Gly Pro Glu Thr Arg Leu Ser Thr Ser
            980                 985                 990

Leu Ser Gly Leu Asn Glu Lys Asn Pro Tyr Arg Asp Ser Ala Tyr Phe
        995                 1000                1005

Ser Asp Leu Glu Ala Glu Ala Glu Ala Thr Ser Gly Pro Glu Lys Lys
    1010                1015                1020

Cys Gly Gly Asp Arg Ala Pro Gly Pro Glu Leu Gly Leu Pro Ser Thr
1025                1030                1035                1040

Gly Gln Pro Ser Glu Gln Val Cys Leu Arg Pro Gly Val Ser Gly Glu
                1045                1050                1055

Ala Gln Gly Ser Gly Pro Gly Glu Val Leu Pro Pro Leu Leu Gln Leu
            1060                1065                1070

Glu Gly Ser Ser Pro Glu Pro Ser Thr Cys Pro Ser Gly Leu Val Pro
        1075                1080                1085

Glu Pro Pro Glu Pro Gln Gly Pro Ala Lys Val Arg Pro Gly Pro Ser
    1090                1095                1100

Pro Ser Cys Ser Gln Phe Phe Leu Leu Thr Pro Val Pro Leu Arg Ser
1105                1110                1115                1120

Glu Gly Asn Ser Ser Glu Phe Gln Gly Pro Pro Gly Leu Leu Ser Gly
                1125                1130                1135

Pro Ala Pro Gln Lys Arg Met Gly Gly Pro Gly Thr Pro Arg Ala Pro
            1140                1145                1150

Leu Arg Leu Ala Leu Pro Gly Leu Pro Ala Ala Leu Glu Gly Arg Pro
        1155                1160                1165

Glu Glu Glu Glu Glu Asp Ser Glu Asp Ser Asp Glu Ser Asp Glu Glu
    1170                1175                1180

Leu Arg Cys Tyr Ser Val Gln Glu Pro Ser Glu Asp Ser Glu Glu Glu
1185                1190                1195                1200

Ala Pro Ala Val Pro Val Val Ala Glu Ser Gln Ser Ala Arg Asn
                1205                1210                1215

Leu Arg Ser Leu Leu Lys Met Pro Ser Leu Leu Ser Glu Thr Phe Cys
            1220                1225                1230

Glu Asp Leu Glu Arg Lys Lys Lys Ala Val Ser Phe Phe Asp Asp Val
        1235                1240                1245

Thr Val Tyr Leu Phe Asp Gln Glu Ser Pro Thr Arg Glu Leu Gly Glu
    1250                1255                1260

Pro Phe Pro Gly Ala Lys Glu Ser Pro Thr Phe Leu Arg Gly Ser
1265                1270                1275                1280

Pro Gly Ser Pro Ser Ala Pro Asn Arg Pro Gln Gln Ala Asp Gly Ser
                1285                1290                1295

Pro Asn Gly Ser Thr Ala Glu Glu Gly Gly Gly Phe Ala Trp Asp Asp
            1300                1305                1310

Asp Phe Pro Leu Met Thr Ala Lys Ala Ala Phe Ala Met Ala Leu Asp
        1315                1320                1325

Pro Ala Ala Pro Ala Pro Ala Ala Pro Thr Pro Thr Pro Ala Pro Phe
    1330                1335                1340

Ser Arg Phe Thr Val Ser Pro Ala Pro Thr Ser Arg Phe Ser Ile Thr
```

```
              1345                1350                1355                1360
His Val Ser Asp Ser Asp Ala Glu Ser Lys Arg Gly Pro Glu Ala Gly
                    1365                1370                1375

Ala Gly Gly Glu Ser Lys Glu Ala
            1380

(2) INFORMATION FOR SEQ ID NO: 12:

(i) SEQUENCE CHARACTERISTICS:
        (A) LENGTH:          80 amino acids
        (B) TYPE:            amino acid
        (C) STRANDEDNESS:    single
        (D) TOPOLOGY:        linear (ii) MOLECULE TYPE:      Protein (xi) SEQUENCE DESCRIPTION: SEQ ID NO: 12:

Gly His Gly Trp Phe Gly Lys Val Phe Leu Gly Glu Val His Ser Gly
1               5                   10                  15

Val Ser Gly Thr Gln Val Val Lys Glu Leu Lys Val Ser Ala Ser
                20                  25                  30

Val Gln Glu Gln Met Gln Phe Leu Glu Ala Gln Pro Tyr Arg Ala
            35                  40                  45

Leu Gln His Ser Asn Leu Leu Gln Cys Leu Ala Gln Cys Ala Glu Val
        50                  55                  60

Thr Pro Tyr Leu Leu Val Met Glu Phe Cys Pro Phe Gly Asp Leu Lys
65                  70                  75                  80

(2) INFORMATION FOR SEQ ID NO: 13:

(i) SEQUENCE CHARACTERISTICS:
        (A) LENGTH:          266 amino acids
        (B) TYPE:            amino acid
        (C) STRANDEDNESS:    single
        (D) TOPOLOGY:        linear (ii) MOLECULE TYPE:      Protein (xi) SEQUENCE DESCRIPTION: SEQ ID NO: 13:

Glu Ile Gly Phe Lys Glu Phe Glu Asp Asn Phe Asp Asp Glu Ile Asp
1               5                   10                  15

Phe Thr Pro Pro Ala Glu Asp Thr Pro Ser Val Gln Ser Pro Ala Glu
                20                  25                  30

Val Phe Thr Leu Ser Val Pro Asn Ile Ser Leu Pro Ala Pro Ser Gln
            35                  40                  45

Phe Gln Ser Ser Val Gly Leu Lys Ser Gln Val Ala Arg His Ser Leu
    50                  55                  60

Asn Tyr Ile Gln Glu Ile Gly Asn Gly Trp Phe Gly Lys Val Leu Leu
65                  70                  75                  80

Gly Glu Thr Tyr Thr Gly Thr Ser Val Thr Arg Val Ile Val Lys Glu
                85                  90                  95

Leu Lys Val Ser Ala Ser Pro Lys Glu Gln Asp Thr Phe Leu Asn Ser
            100                 105                 110

Gly Glu Pro Tyr Tyr Ile Leu Gln His Pro Asn Val Leu Gln Cys Val
        115                 120                 125

Gly Gln Cys Val Glu Ala Ile Pro Tyr Leu Leu Val Phe Glu Phe Cys
    130                 135                 140

Asp Leu Gly Asp Leu Lys Ala Tyr Leu His Asn Glu Gln Glu His Val
145                 150                 155                 160
```

```
Arg Ser Glu Ser Gln Thr Met Leu Leu Gln Arg Met Ala Cys Glu Ile
                165                 170                 175

Ala Ala Gly Leu Ala Ala Met His Lys Leu His Phe Leu His Ser Asp
            180                 185                 190

Leu Ala Leu Arg Asn Cys Tyr Leu Thr Ser Asp Leu Asn Val Lys Val
        195                 200                 205

Gly Asp Tyr Gly Ile Gly Phe Ser Arg Tyr Lys Glu Asp Tyr Ile Glu
    210                 215                 220

Thr Asp Asp Lys Lys Ile Phe Pro Leu Arg Trp Thr Ala Pro Glu Leu
225                 230                 235                 240

Val Thr Ser Phe Gln Asp Arg Leu Leu Thr Ala Asp Gln Thr Lys Tyr
                245                 250                 255

Ser Asn Ile Trp Thr Leu Gly Val Thr Ile
                260                 265
```

(2) INFORMATION FOR SEQ ID NO: 14:

(i) SEQUENCE CHARACTERISTICS:
        (A) LENGTH: 1503 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO: 14:

```
Met Pro Gly Pro Pro Ala Leu Arg Arg Arg Leu Leu Leu Leu Leu Leu
 1               5                  10                  15

Val Leu Leu Ile Ala Gly Ser Ala Gly Ala Ala Pro Leu Pro Gln Thr
            20                  25                  30

Gly Ala Gly Glu Ala Pro Pro Ala Ala Glu Val Ser Ser Ser Phe Val
        35                  40                  45

Ile Leu Cys Val Cys Ser Leu Ile Ile Leu Ile Val Leu Ile Ala Asn
    50                  55                  60

Cys Val Ser Cys Cys Lys Asp Pro Glu Ile Asp Phe Lys Glu Phe Glu
65                  70                  75                  80

Asp Asn Phe Asp Asp Glu Ile Asp Phe Thr Pro Pro Ala Glu Asp Thr
                85                  90                  95

Pro Ser Val Gln Ser Pro Ala Glu Val Phe Thr Leu Ser Val Pro Asn
                100                 105                 110

Ile Ser Leu Pro Ala Pro Ser Gln Phe Gln Pro Ser Val Glu Gly Leu
            115                 120                 125

Lys Ser Gln Val Ala Arg His Ser Leu Asn Tyr Ile Gln Glu Ile Gly
130                 135                 140

Asn Gly Trp Phe Gly Lys Val Leu Leu Gly Glu Ile Tyr Thr Gly Thr
145                 150                 155                 160

Ser Val Ala Arg Val Ile Val Lys Glu Leu Lys Ala Ser Ala Asn Pro
                165                 170                 175

Lys Glu Gln Asp Thr Phe Leu Lys Asn Gly Glu Pro Tyr Tyr Ile Leu
            180                 185                 190

Gln His Pro Asn Ile Leu Gln Cys Val Gly Gln Cys Val Glu Ala Ile
        195                 200                 205

Pro Tyr Leu Leu Val Phe Glu Phe Cys Asp Leu Gly Asp Leu Lys Ala
    210                 215                 220

Tyr Leu Arg Ser Glu Gln Glu His Met Arg Gly Asp Ser Gln Thr Met
225                 230                 235                 240
```

-continued

```
Leu Leu Gln Arg Met Ala Cys Glu Val Ala Ala Gly Leu Ala Ala Met
            245                 250                 255

His Lys Leu His Phe Leu His Ser Asp Leu Ala Leu Arg Asn Cys Phe
        260                 265                 270

Leu Thr Ser Asp Leu Asn Val Lys Val Gly Asp Tyr Gly Ile Gly Phe
    275                 280                 285

Ser Arg Tyr Lys Glu Asp Tyr Ile Glu Thr Asp Lys Lys Val Phe
290                 295                 300

Pro Leu Arg Trp Thr Ala Pro Glu Leu Val Thr Ser Phe Gln Asp Arg
305                 310                 315                 320

Leu Leu Thr Ala Asp Gln Thr Lys Tyr Ser Asn Ile Trp Ser Leu Gly
                325                 330                 335

Val Thr Leu Trp Glu Leu Phe Asp Asn Ala Ala Gln Pro Tyr Ser Asn
            340                 345                 350

Leu Ser Asn Leu Asp Val Leu Asn Gln Val Ile Arg Glu Arg Asp Thr
        355                 360                 365

Lys Leu Pro Lys Pro Gln Leu Glu Gln Pro Tyr Ser Asp Arg Trp Tyr
    370                 375                 380

Glu Val Leu Gln Phe Cys Trp Leu Ser Pro Glu Lys Arg Pro Ala Ala
385                 390                 395                 400

Glu Asp Val His Arg Leu Leu Thr Tyr Leu Arg Leu Gln Ser Gln Arg
                405                 410                 415

Asp Ser Glu Val Asp Phe Glu Gln Gln Trp Asn Ala Leu Lys Pro Asn
            420                 425                 430

Thr Asn Ser Arg Asp Ser Ser Asn Asn Ala Ala Phe Pro Ile Leu Asp
        435                 440                 445

His Phe Ala Arg Asp Arg Leu Gly Arg Glu Met Glu Glu Val Leu Thr
    450                 455                 460

Val Thr Glu Thr Ser Gln Gly Leu Ser Phe Glu Tyr Val Trp Glu Ala
465                 470                 475                 480

Ala Lys His Asp His Phe Asp Glu Arg Ser Arg Gly His Leu Asp Glu
                485                 490                 495

Gly Leu Ser Tyr Thr Ser Ile Phe Tyr Pro Val Glu Val Phe Glu Ser
            500                 505                 510

Ser Leu Ser Asp Pro Gly Pro Gly Lys Gln Asp Ser Gly Gln Asp
        515                 520                 525

Val Pro Leu Arg Val Pro Gly Val Val Pro Val Phe Asp Ala His Asn
530                 535                 540

Leu Ser Val Gly Ser Asp Tyr Tyr Ile Gln Leu Glu Glu Lys Ser Gly
545                 550                 555                 560

Ser Asn Leu Glu Leu Asp Tyr Pro Pro Ala Leu Leu Thr Thr Asp Met
                565                 570                 575

Asp Asn Pro Glu Arg Thr Gly Pro Glu Leu Ser Gln Leu Thr Ala Leu
            580                 585                 590

Arg Ser Val Glu Leu Glu Glu Ser Thr Asp Glu Asp Phe Phe Gln
        595                 600                 605

Ser Ser Thr Asp Pro Lys Asp Ser Ser Leu Pro Gly Asp Leu His Val
    610                 615                 620

Thr Ser Gly Pro Glu Ser Pro Phe Asn Asn Ile Phe Asn Asp Val Asp
625                 630                 635                 640

Lys Ser Glu Asp Leu Pro Ser His Gln Lys Ile Phe Asp Leu Met Glu
                645                 650                 655

Leu Asn Gly Val Gln Ala Asp Phe Lys Pro Ala Thr Leu Ser Ser Ser
```

-continued

```
                660                 665                 670
Leu Asp Asn Pro Lys Glu Ser Val Ile Thr Gly His Phe Glu Lys Glu
            675                 680                 685
Lys Pro Arg Lys Ile Phe Asp Ser Glu Pro Leu Cys Leu Ser Asp Asn
        690                 695                 700
Leu Met His Gln Asp Asn Phe Asp Pro Leu Asn Val Gln Glu Leu Ser
705                 710                 715                 720
Glu Asn Phe Leu Phe Leu Gln Glu Lys Asn Leu Leu Lys Gly Ser Leu
                725                 730                 735
Ser Ser Lys Glu His Ile Asn Asp Leu Gln Thr Glu Leu Lys Asn Ala
            740                 745                 750
Gly Phe Thr Glu Ala Met Leu Glu Thr Ser Cys Arg Asn Ser Leu Asp
        755                 760                 765
Thr Glu Leu Gln Phe Ala Glu Asn Lys Pro Gly Leu Ser Leu Leu Gln
    770                 775                 780
Glu Asn Val Ser Thr Lys Gly Asp Asp Thr Asp Val Met Leu Thr Gly
785                 790                 795                 800
Asp Thr Leu Ser Thr Ser Leu Gln Ser Ser Pro Glu Val Gln Val Pro
                805                 810                 815
Pro Thr Ser Phe Glu Thr Glu Glu Thr Pro Arg Arg Val Pro Pro Asp
            820                 825                 830
Ser Leu Pro Thr Gln Gly Glu Thr Gln Pro Thr Cys Leu Asp Val Ile
        835                 840                 845
Val Pro Glu Asp Cys Leu His Gln Asp Ile Ser Pro Asp Ala Val Thr
    850                 855                 860
Val Pro Val Glu Ile Leu Ser Thr Asp Ala Arg Thr His Ser Leu Asp
865                 870                 875                 880
Asn Arg Ser Gln Asp Ser Pro Gly Glu Ser Glu Glu Thr Leu Arg Leu
                885                 890                 895
Thr Glu Ser Asp Ser Val Leu Ala Asp Asp Ile Leu Ala Ser Arg Val
            900                 905                 910
Ser Val Gly Ser Ser Leu Pro Glu Leu Gly Gln Glu Leu His Asn Lys
        915                 920                 925
Pro Phe Ser Glu Asp His His Ser His Arg Arg Leu Glu Lys Asn Leu
    930                 935                 940
Glu Ala Val Glu Thr Leu Asn Gln Leu Asn Ser Lys Asp Ala Ala Lys
945                 950                 955                 960
Glu Ala Gly Leu Val Ser Ala Leu Ser Ser Asp Ser Thr Ser Gln Asp
                965                 970                 975
Ser Leu Leu Glu Asp Ser Leu Ser Ala Pro Phe Pro Ala Ser Glu Pro
            980                 985                 990
Ser Leu Glu Thr Pro Asp Ser Leu Glu Ser Val Asp Val His Glu Ala
        995                 1000                1005
Leu Leu Asp Ser Leu Gly Ser His Thr Pro Gln Lys Leu Val Pro Pro
    1010                1015                1020
Asp Lys Pro Ala Asp Ser Gly Tyr Glu Thr Glu Asn Leu Glu Ser Pro
1025                1030                1035                1040
Glu Trp Thr Leu His Pro Ala Pro Glu Gly Thr Ala Asp Ser Glu Pro
                1045                1050                1055
Ala Thr Thr Gly Asp Gly Gly His Ser Gly Leu Pro Pro Asn Pro Val
            1060                1065                1070
Ile Val Ile Ser Asp Ala Gly Asp Gly His Arg Gly Thr Glu Val Thr
        1075                1080                1085
```

-continued

```
Pro Glu Thr Phe Thr Ala Gly Ser Gln Gly Ser Tyr Arg Asp Ser Ala
    1090                1095                1100

Tyr Phe Ser Asp Asn Asp Ser Glu Pro Glu Lys Arg Ser Glu Val
1105                1110                1115                1120

Pro Gly Thr Ser Pro Ser Ala Leu Val Leu Val Gln Glu Gln Pro Leu
            1125                1130                1135

Pro Glu Pro Val Leu Pro Glu Gln Ser Pro Ala Ala Gln Asp Ser Cys
            1140                1145                1150

Leu Glu Ala Arg Lys Ser Gln Pro Asp Glu Ser Cys Leu Ser Ala Leu
        1155                1160                1165

His Asn Ser Ser Asp Leu Glu Leu Arg Ala Thr Pro Glu Pro Ala Gln
    1170                1175                1180

Thr Gly Val Pro Gln Gln Val His Pro Thr Glu Asp Glu Ala Ser Ser
1185                1190                1195                1200

Pro Trp Ser Val Leu Asn Ala Glu Leu Ser Ser Gly Asp Asp Phe Glu
            1205                1210                1215

Thr Gln Asp Asp Arg Pro Cys Thr Leu Ala Ser Thr Gly Thr Asn Thr
            1220                1225                1230

Asn Glu Leu Leu Ala Tyr Thr Asn Ser Ala Leu Asp Lys Ser Leu Ser
    1235                1240                1245

Ser His Ser Glu Gly Pro Lys Leu Lys Glu Pro Asp Ile Glu Gly Lys
    1250                1255                1260

Tyr Leu Gly Lys Leu Gly Val Ser Gly Met Leu Asp Leu Ser Glu Asp
1265                1270                1275                1280

Gly Met Asp Ala Asp Glu Glu Asp Glu Asn Ser Asp Asp Ser Asp Glu
            1285                1290                1295

Asp Leu Arg Ala Phe Asn Leu His Ser Leu Ser Ser Glu Ser Glu Asp
            1300                1305                1310

Glu Thr Glu His Pro Val Pro Ile Ile Leu Ser Asn Glu Asp Gly Arg
        1315                1320                1325

His Leu Arg Ser Leu Leu Lys Pro Thr Ala Ala Asn Ala Pro Asp Pro
    1330                1335                1340

Leu Pro Glu Asp Trp Lys Lys Glu Lys Lys Ala Val Thr Phe Phe Asp
1345                1350                1355                1360

Asp Val Thr Val Tyr Leu Phe Asp Gln Glu Thr Pro Thr Lys Glu Leu
                1365                1370                1375

Gly Pro Cys Gly Gly Glu Ala Cys Gly Pro Asp Leu Ser Gly Pro Ala
            1380                1385                1390

Pro Ala Ser Gly Ser Pro Tyr Leu Ser Arg Cys Ile Asn Ser Glu Ser
        1395                1400                1405

Ser Thr Asp Glu Glu Gly Gly Gly Phe Glu Trp Asp Asp Phe Ser
    1410                1415                1420

Pro Asp Pro Phe Met Ser Lys Thr Thr Ser Asn Leu Leu Ser Ser Lys
1425                1430                1435                1440

Pro Ser Leu Gln Thr Ser Lys Tyr Phe Ser Pro Pro Pro Ala Arg
            1445                1450                1455

Ser Thr Glu Gln Ser Trp Pro His Ser Ala Pro Tyr Ser Arg Phe Ser
    1460                1465                1470

Ile Ser Pro Ala Asn Ile Ala Ser Phe Ser Leu Thr His Leu Thr Asp
        1475                1480                1485

Ser Asp Ile Glu Gln Gly Gly Ser Ser Glu Asp Gly Glu Lys Asp
    1490                1495                1500
```

(2) INFORMATION FOR SEQ ID NO: 15:

(i) SEQUENCE CHARACTERISTICS:
        (A) LENGTH:        80 amino acids
        (B) TYPE:          amino acid
        (C) STRANDEDNESS:  single
        (D) TOPOLOGY:     linear (ii) MOLECULE TYPE:      Protein (xi) SEQUENCE DESCRIPTION: SEQ ID NO: 15:

```
Gly His Gly Trp Phe Gly Lys Val Phe Leu Gly Glu Thr Tyr Thr Gly
 1               5                  10                  15

Thr Ser Val Ala Arg Val Ile Val Lys Glu Leu Lys Val Ser Ala Ser
            20                  25                  30

Pro Lys Glu Gln Asp Thr Phe Leu Lys Ser Gly Glu Pro Tyr Tyr Ile
        35                  40                  45

Leu Gln His Pro Asn Val Leu Gln Cys Val Gly Gln Cys Val Glu Ala
    50                  55                  60

Ile Pro Tyr Leu Leu Val Phe Glu Phe Cys Pro Phe Gly Asp Leu Lys
65                  70                  75                  80
```

(2) INFORMATION FOR SEQ ID NO: 16:

(i) SEQUENCE CHARACTERISTICS:
        (A) LENGTH:        275 amino acids
        (B) TYPE:          amino acid
        (C) STRANDEDNESS:  single
        (D) TOPOLOGY:     linear (ii) MOLECULE TYPE:      Protein (xi) SEQUENCE DESCRIPTION: SEQ ID NO: 16:

```
Glu Ile Gly Phe Lys Glu Phe Glu Asn Pro Glu Gly Glu Asp Cys Ser
 1               5                  10                  15

Gly Glu Tyr Thr Pro Pro Ala Glu Glu Thr Ser Ser Ser Gln Ser Leu
            20                  25                  30

Pro Asp Val Tyr Ile Leu Pro Leu Ala Glu Val Ser Leu Pro Met Pro
        35                  40                  45

Ala Pro Gln Pro Ala His Ser Asp Ile Ser Thr Pro Leu Gly Leu Ser
    50                  55                  60

Arg Gln His Leu Ser Tyr Leu Gln Glu Ile Gly Ser Gly Trp Phe Gly
65                  70                  75                  80

Lys Val Ile Leu Gly Glu Val Phe Ser Asp Tyr Ser Pro Ala Gln Val
                85                  90                  95

Val Val Lys Glu Leu Arg Ala Ser Ala Gly Pro Leu Glu Gln Arg Lys
            100                 105                 110

Phe Ile Ser Glu Ala Gln Pro Tyr Arg Ser Leu Gln His Pro Asn Val
        115                 120                 125

Leu Gln Cys Leu Gly Val Cys Val Glu Thr Leu Pro Phe Leu Leu Ile
    130                 135                 140

Met Glu Phe Cys Gln Leu Gly Asp Leu Lys Arg Tyr Leu Arg Ala Gln
145                 150                 155                 160

Arg Pro Pro Glu Gly Met Ser Pro Glu Leu Pro Pro Arg Asp Leu Arg
                165                 170                 175

Thr Leu Gln Arg Met Gly Leu Glu Ile Ala Arg Gly Leu Ala His Leu
            180                 185                 190

His Ser His Asn Tyr Val His Ser Asp Leu Ala Leu Arg Asn Cys Leu
        195                 200                 205
```

```
Leu Thr Ser Asp Leu Thr Val Arg Ile Gly Asp Tyr Gly Leu Ala His
    210                 215                 220

Ser Asn Tyr Lys Glu Asp Tyr Tyr Leu Thr Pro Glu Arg Leu Trp Val
225                 230                 235                 240

Pro Leu Arg Trp Ala Ala Pro Glu Leu Leu Gly Glu Leu His Gly Ser
                245                 250                 255

Phe Val Leu Val Asp Gln Ser Arg Glu Ser Asn Ile Trp Thr Leu Gly
                260                 265                 270

Val Thr Ile
        275

(2) INFORMATION FOR SEQ ID NO: 17:

(i) SEQUENCE CHARACTERISTICS:
        (A) LENGTH:              472 amino acids
        (B) TYPE:                amino acid
        (C) STRANDEDNESS:        single
        (D) TOPOLOGY:            linear (ii) MOLECULE TYPE:          Protein (xi) SEQUENCE DESCRIPTION: SEQ ID NO: 17:

Met Pro Ala Pro Gly Ala Leu Ile Leu Leu Ala Ala Val Ser Ala Ser
1                   5                   10                  15

Gly Cys Leu Ala Ser Pro Ala His Pro Asp Gly Phe Ala Leu Gly Arg
                20                  25                  30

Ala Pro Leu Ala Pro Pro Tyr Ala Val Val Leu Ile Ser Cys Ser Gly
            35                  40                  45

Leu Leu Ala Phe Ile Phe Leu Leu Leu Thr Cys Leu Cys Cys Lys Arg
    50                  55                  60

Gly Asp Val Gly Phe Lys Glu Phe Glu Asn Pro Glu Gly Glu Asp Cys
65                  70                  75                  80

Ser Gly Glu Tyr Thr Pro Pro Ala Glu Glu Thr Ser Ser Ser Gln Ser
                85                  90                  95

Leu Pro Asp Val Tyr Ile Leu Pro Leu Ala Glu Val Ser Leu Pro Met
                100                 105                 110

Pro Ala Pro Gln Pro Ser His Ser Asp Met Thr Thr Pro Leu Gly Leu
            115                 120                 125

Ser Arg Gln His Leu Ser Tyr Leu Gln Glu Ile Gly Ser Gly Trp Phe
130                 135                 140

Gly Lys Val Ile Leu Gly Glu Ile Phe Ser Asp Tyr Thr Pro Ala Gln
145                 150                 155                 160

Val Val Val Lys Glu Leu Arg Ala Ser Ala Gly Pro Leu Glu Gln Arg
                165                 170                 175

Lys Phe Ile Ser Glu Ala Gln Pro Tyr Arg Ser Leu Gln His Pro Asn
            180                 185                 190

Val Leu Gln Cys Leu Gly Leu Cys Val Glu Thr Leu Pro Phe Leu Leu
            195                 200                 205

Ile Met Glu Phe Cys Gln Leu Gly Asp Leu Lys Arg Tyr Leu Arg Ala
    210                 215                 220

Gln Arg Pro Pro Glu Gly Leu Ser Pro Glu Leu Pro Pro Arg Asp Leu
225                 230                 235                 240

Arg Thr Leu Gln Arg Met Gly Leu Glu Ile Ala Arg Gly Leu Ala His
                245                 250                 255

Leu His Ser His Asn Tyr Val His Ser Asp Leu Ala Leu Arg Asn Cys
                260                 265                 270
```

```
Leu Leu Thr Ser Asp Leu Thr Val Arg Ile Gly Asp Tyr Gly Leu Ala
            275                 280                 285

His Ser Asn Tyr Lys Glu Asp Tyr Tyr Leu Thr Pro Glu Arg Leu Trp
        290                 295                 300

Ile Pro Leu Arg Trp Ala Ala Pro Glu Leu Leu Gly Glu Leu His Gly
305                 310                 315                 320

Thr Phe Met Val Met Asp Gln Ser Arg Glu Ser Asn Ile Trp Ser Leu
                325                 330                 335

Gly Val Thr Leu Trp Glu Leu Phe Glu Phe Gly Ala Gln Pro Tyr Arg
            340                 345                 350

His Leu Ser Asp Glu Glu Val Leu Ala Phe Val Val Arg Gln Gln His
        355                 360                 365

Val Lys Leu Ala Arg Pro Lys Leu Lys Leu Pro Tyr Ala Asp Tyr Trp
    370                 375                 380

Tyr Asp Ile Leu Gln Ser Cys Trp Arg Pro Ala Gln Arg Pro Ser
385                 390                 395                 400

Ala Ser Asp Leu Gln Leu Gln Leu Thr Tyr Leu Leu Ser Glu Arg Pro
                405                 410                 415

Pro Arg Pro Pro Pro Pro Pro Pro Arg Asp Gly Pro Phe Pro
            420                 425                 430

Trp Pro Trp Pro Pro Ala His Ser Ala Pro Arg Pro Gly Thr Leu Ser
            435                 440                 445

Ser Pro Phe Pro Leu Leu Asp Gly Phe Pro Gly Ala Asp Pro Asp Asp
        450                 455                 460

Val Leu Thr Val Thr Glu Ser Ser
465                 470

(2) INFORMATION FOR SEQ ID NO: 18:

(i) SEQUENCE CHARACTERISTICS:
        (A) LENGTH:         178 amino acids
        (B) TYPE:           amino acid
        (C) STRANDEDNESS:   single
        (D) TOPOLOGY:       linear (ii) MOLECULE TYPE:        Protein (xi) SEQUENCE DESCRIPTION: SEQ ID NO: 18:

Arg Glu Phe Arg Ser Gly Ala Gly Pro Leu Glu Gln Arg Lys Phe Ile
1               5                   10                  15

Ser Glu Ala Gln Pro Tyr Arg Ser Leu Gln Arg Pro Asn Val Leu Gln
            20                  25                  30

Cys Leu Gly Val Cys Val Glu Thr Leu Pro Phe Leu Leu Ile Met Glu
        35                  40                  45

Phe Cys Gln Leu Gly Asp Leu Lys Arg Tyr Leu Arg Ala Gln Arg Pro
50              55                  60

Pro Glu Gly Met Ser Pro Glu Leu Pro Pro Arg Asp Leu Arg Thr Leu
65              70                  75                  80

Gln Arg Met Gly Leu Glu Ile Ala Arg Gly Leu Ala His Leu His Ser
            85                  90                  95

His Asn Tyr Val His Ser Asp Leu Ala Leu Arg Asn Cys Leu Leu Thr
        100                 105                 110

Ser Asp Leu Thr Val Arg Ile Gly Asp Tyr Gly Leu Ala His Ser Asn
            115                 120                 125

Tyr Lys Glu Asp Tyr Tyr Leu Thr Pro Glu Arg Leu Trp Val Pro Leu
        130                 135                 140
```

```
Arg Trp Ala Ala Pro Glu Leu Leu Gly Glu Leu His Gly Ser Phe Val
145                 150                 155                 160

Leu Val Asp Gln Ser Arg Glu Ser Asn Val Trp Ser Leu Gly Val Thr
                165                 170                 175

Ile Ile
```

(2) INFORMATION FOR SEQ ID NO: 19:

(i) SEQUENCE CHARACTERISTICS:
        (A) LENGTH:          16 amino acids
        (B) TYPE:            amino acid
        (C) STRANDEDNESS:   single
        (D) TOPOLOGY:        linear (ii) MOLECULE TYPE:        Protein (xi) SEQUENCE DESCRIPTION: SEQ ID NO: 19:

```
Asp Ser Asp Ile Glu Gln Gly Gly Ser Ser Glu Asp Gly Glu Lys Asp
1               5                   10                  15
```

(2) INFORMATION FOR SEQ ID NO: 20:

(i) SEQUENCE CHARACTERISTICS:
        (A) LENGTH:          15 amino acids
        (B) TYPE:            amino acid
        (C) STRANDEDNESS:   single
        (D) TOPOLOGY:        linear (ii) MOLECULE TYPE:        Protein (xi) SEQUENCE DESCRIPTION: SEQ ID NO: 20:

```
Asp Asp Glu Ile Asp Phe Thr Pro Pro Ala Glu Asp Thr Pro Ser
1               5                   10                  15
```

(2) INFORMATION FOR SEQ ID NO: 21:

(i) SEQUENCE CHARACTERISTICS:
        (A) LENGTH:          15 amino acids
        (B) TYPE:            amino acid
        (C) STRANDEDNESS:   single
        (D) TOPOLOGY:        linear (ii) MOLECULE TYPE:        Protein (xi) SEQUENCE DESCRIPTION: SEQ ID NO: 21:

```
His Phe Glu Lys Glu Lys Pro Arg Lys Ile Phe Asp Ser Glu Pro
1               5                   10                  15
```

(2) INFORMATION FOR SEQ ID NO: 22:

(i) SEQUENCE CHARACTERISTICS:
        (A) LENGTH:          16 amino acids
        (B) TYPE:            amino acid
        (C) STRANDEDNESS:   single
        (D) TOPOLOGY:        linear (ii) MOLECULE TYPE:        Protein (xi) SEQUENCE DESCRIPTION: SEQ ID NO: 22:

```
Gly Ser Tyr Arg Asp Ser Ala Tyr Phe Ser Asp Asn Asp Ser Glu Pro
1               5                   10                  15
```

(2) INFORMATION FOR SEQ ID NO: 23:

(i) SEQUENCE CHARACTERISTICS:
        (A) LENGTH:          23 base pairs
        (B) TYPE:            nucleic acid

```
          (C) STRANDEDNESS:       single
          (D) TOPOLOGY:           linear (xi) SEQUENCE DESCRIPTION: SEQ ID NO: 23:

TGAAAGTGGG AGATTACGGA ATA                                              23

(2) INFORMATION FOR SEQ ID NO: 24:

(i) SEQUENCE CHARACTERISTICS:
          (A) LENGTH:            24 base pairs
          (B) TYPE:              nucleic acid
          (C) STRANDEDNESS:      single
          (D) TOPOLOGY:          linear (xi) SEQUENCE DESCRIPTION: SEQ ID NO: 24:

GTTACTATAC TTAGTCTGAT CTGC                                             24

(2) INFORMATION FOR SEQ ID NO: 25:

(i) SEQUENCE CHARACTERISTICS:
          (A) LENGTH:            18 amino acids
          (B) TYPE:              amino acid
          (C) STRANDEDNESS:      single
          (D) TOPOLOGY:          linear (ii) MOLECULE TYPE:          Protein (xi) SEQUENCE DESCRIPTION: SEQ ID NO: 25:

Ala Phe Ser Ser His Phe Asp Pro Asp Gly Ala Pro Leu Ser Glu Leu
 1               5                  10                  15

Ser Trp (2) INFORMATION FOR SEQ ID NO: 26:

(i) SEQUENCE CHARACTERISTICS:
          (A) LENGTH:            12 amino acids
          (B) TYPE:              amino acid
          (C) STRANDEDNESS:      single
          (D) TOPOLOGY:          linear (ii) MOLECULE TYPE:          Protein (xi) SEQUENCE DESCRIPTION: SEQ ID NO: 26:

Ala Pro Leu Pro Gln Thr Gly Ala Gly Glu Ala Pro
 1               5                  10

(2) INFORMATION FOR SEQ ID NO: 27:

(i) SEQUENCE CHARACTERISTICS:
          (A) LENGTH:            14 amino acids
          (B) TYPE:              amino acid
          (C) STRANDEDNESS:      single
          (D) TOPOLOGY:          linear (ii) MOLECULE TYPE:          Protein (xi) SEQUENCE DESCRIPTION: SEQ ID NO: 27:

Ser Pro Ala His Pro Asp Gly Phe Ala Leu Gly Arg Ala Pro
 1               5                  10

(2) INFORMATION FOR SEQ ID NO: 28:

(i) SEQUENCE CHARACTERISTICS:
          (A) LENGTH:            4 amino acids
          (B) TYPE:              amino acid
          (C) STRANDEDNESS:      single
          (D) TOPOLOGY:          linear
```

```
        (ii) MOLECULE TYPE:           Protein (xi) SEQUENCE DESCRIPTION: SEQ ID NO: 28:

Val Ala Val Lys
1

(2) INFORMATION FOR SEQ ID NO: 29:

(i) SEQUENCE CHARACTERISTICS:
            (A) LENGTH:               4 amino acids
            (B) TYPE:                 amino acid
            (C) STRANDEDNESS:         single
            (D) TOPOLOGY:             linear (ii) MOLECULE TYPE:           Protein (ix) FEATURE:
            (D) OTHER INFORMATION:    "Xaa" stands for Val or Ile.

(xi) SEQUENCE DESCRIPTION: SEQ ID NO: 29:

Val Xaa Val Lys
1

(2) INFORMATION FOR SEQ ID NO: 30:

(i) SEQUENCE CHARACTERISTICS:
            (A) LENGTH:               4 amino acids
            (B) TYPE:                 amino acid
            (C) STRANDEDNESS:         single
            (D) TOPOLOGY:             linear (ii) MOLECULE TYPE:           Protein (xi) SEQUENCE DESCRIPTION: SEQ ID NO: 30:

Asp Val Trp Ser
1

(2) INFORMATION FOR SEQ ID NO: 31:

(i) SEQUENCE CHARACTERISTICS:
            (A) LENGTH:               4 amino acids
            (B) TYPE:                 amino acid
            (C) STRANDEDNESS:         single
            (D) TOPOLOGY:             linear (ii) MOLECULE TYPE:           Protein (xi) SEQUENCE DESCRIPTION: SEQ ID NO: 31:

Asn Val Trp Ser
1

(2) INFORMATION FOR SEQ ID NO: 32:

(i) SEQUENCE CHARACTERISTICS:
            (A) LENGTH:               25 base pairs
            (B) TYPE:                 nucleic acid
            (C) STRANDEDNESS:         single
            (D) TOPOLOGY:             linear (ix) FEATURE:
            (D) OTHER INFORMATION:    "N" stands for A, C, G or T.
                "Y" stands for C or T.
                "R" stands for A or G.

(xi) SEQUENCE DESCRIPTION: SEQ ID NO: 32:

GAAAGCTTGG NGCNTTYGGN AARGT                                              25

(2) INFORMATION FOR SEQ ID NO: 33:
```

```
        (i) SEQUENCE CHARACTERISTICS:
             (A) LENGTH:          24 base pairs
             (B) TYPE:            nucleic acid
             (C) STRANDEDNESS:    single
             (D) TOPOLOGY:        linear (ix) FEATURE:
             (D) OTHER INFORMATION:  "Y" stands for C or T.
                 "N" stands for A, C, G or T.

(xi) SEQUENCE DESCRIPTION: SEQ ID NO: 33:

GCCAAGCTTY TCNGGNGGCA TCCA                                          24

(2) INFORMATION FOR SEQ ID NO: 34:

(i) SEQUENCE CHARACTERISTICS:
             (A) LENGTH:          31 base pairs
             (B) TYPE:            nucleic acid
             (C) STRANDEDNESS:    single
             (D) TOPOLOGY:        linear (ix) FEATURE:
             (D) OTHER INFORMATION:  "N" stands for A, C, G or T.
                 "R" stands for A or G.
                 "Y" stands for C or T.

(xi) SEQUENCE DESCRIPTION: SEQ ID NO: 34:

CTGAATTCGG NGARGGNAAY TTYGGNCARG T                                  31

(2) INFORMATION FOR SEQ ID NO: 35:

(i) SEQUENCE CHARACTERISTICS:
             (A) LENGTH:          23 base pairs
             (B) TYPE:            nucleic acid
             (C) STRANDEDNESS:    single
             (D) TOPOLOGY:        linear (ix) FEATURE:
             (D) OTHER INFORMATION:  "N" stands for A, C, G or T.
                 "Y" stands for C or T.
                 "R" stands for A or G.

(xi) SEQUENCE DESCRIPTION: SEQ ID NO: 35:

GCNTTYGGNG ARGTNTAYGA RGG                                           23

(2) INFORMATION FOR SEQ ID NO: 36:

(i) SEQUENCE CHARACTERISTICS:
             (A) LENGTH:          36 base pairs
             (B) TYPE:            nucleic acid
             (C) STRANDEDNESS:    single
             (D) TOPOLOGY:        linear (ix) FEATURE:
             (D) OTHER INFORMATION:  "N" stands for A, C, G or T.
                 "Y" stands for C or T.
                 "M" stands for A or C.
                 "R" stands for A or G.

(xi) SEQUENCE DESCRIPTION: SEQ ID NO: 36:

CCGGGATCCA CAAGCTTCCC TNCAYMRDGA YNTNGC                             36

(2) INFORMATION FOR SEQ ID NO: 37:

(i) SEQUENCE CHARACTERISTICS:
             (A) LENGTH:          26 base pairs
             (B) TYPE:            nucleic acid
             (C) STRANDEDNESS:    single
             (D) TOPOLOGY:        linear (ix) FEATURE:
```

```
            (D) OTHER INFORMATION:   "Y" stands for C or T.
                "N" stands for A, C, G or T.
                "R" stands for A or G.

(xi) SEQUENCE DESCRIPTION: SEQ ID NO: 37:

GGCCACGGCT GGTTYGGNAA RGTNTT                                          26

(2) INFORMATION FOR SEQ ID NO: 38:

(i) SEQUENCE CHARACTERISTICS:
        (A) LENGTH:             24 base pairs
        (B) TYPE:               nucleic acid
        (C) STRANDEDNESS:       single
        (D) TOPOLOGY:           linear (ix) FEATURE:
        (D) OTHER INFORMATION:   "R" stands for A or G.
            "Y" stands for C or T.
            "N" stands for A, C, G or T.

(xi) SEQUENCE DESCRIPTION: SEQ ID NO: 38:

ATGCARTTYC TGGARGARGC NCAY                                            24

(2) INFORMATION FOR SEQ ID NO: 39:

(i) SEQUENCE CHARACTERISTICS:
        (A) LENGTH:             24 base pairs
        (B) TYPE:               nucleic acid
        (C) STRANDEDNESS:       single
        (D) TOPOLOGY:           linear (ix) FEATURE:
        (D) OTHER INFORMATION:   "R" stands for A or G.
            "N" stands for A, C, G or T.
            "Y" stands for C or T.

(xi) SEQUENCE DESCRIPTION: SEQ ID NO: 39:

ATGTAGRTRC ARNAYNCCRC ANGC                                            24

(2) INFORMATION FOR SEQ ID NO: 40:

(i) SEQUENCE CHARACTERISTICS:
        (A) LENGTH:             27 base pairs
        (B) TYPE:               nucleic acid
        (C) STRANDEDNESS:       single
        (D) TOPOLOGY:           linear (ix) FEATURE:
        (D) OTHER INFORMATION:   "R" stands for A or G.
            "N" stands for A, C, G or T.
            "Y" stands for C or T.

(xi) SEQUENCE DESCRIPTION: SEQ ID NO: 40:

GCTCCGTAGR TANCCYTTNA RRTCNCC                                         27

(2) INFORMATION FOR SEQ ID NO: 41:

(i) SEQUENCE CHARACTERISTICS:
        (A) LENGTH:             27 base pairs
        (B) TYPE:               nucleic acid
        (C) STRANDEDNESS:       single
        (D) TOPOLOGY:           linear (ix) FEATURE:
        (D) OTHER INFORMATION:   "N" stands for A, C, G or T.
            "R" stands for A or G.
            "S" stands for C or G.
            "W" stands for A or T.

(xi) SEQUENCE DESCRIPTION: SEQ ID NO: 41:
```

```
GATTGTNACN CCNARNSWCC ANACRTT                                              27

(2) INFORMATION FOR SEQ ID NO: 42:

(i) SEQUENCE CHARACTERISTICS:
          (A) LENGTH:           26 base pairs
          (B) TYPE:             nucleic acid
          (C) STRANDEDNESS:     single
          (D) TOPOLOGY:         linear (ix) FEATURE:
          (D) OTHER INFORMATION:   "R" stands for A or G.
               "N" stands for A, C, G or T.
               "Y" stands for C or T.

(xi) SEQUENCE DESCRIPTION: SEQ ID NO: 42:

TTCAGRTCNC CNARNGGRCA RAAYTC                                               26

(2) INFORMATION FOR SEQ ID NO: 43:

(i) SEQUENCE CHARACTERISTICS:
          (A) LENGTH:           6 amino acids
          (B) TYPE:             amino acid
          (C) STRANDEDNESS:     single
          (D) TOPOLOGY:         linear (ii) MOLECULE TYPE:        Protein (xi) SEQUENCE DESCRIPTION: SEQ ID NO: 43:

Gly Ala Phe Gly Lys Val
1               5

(2) INFORMATION FOR SEQ ID NO: 44:

(i) SEQUENCE CHARACTERISTICS:
          (A) LENGTH:           5 amino acids
          (B) TYPE:             amino acid
          (C) STRANDEDNESS:     single
          (D) TOPOLOGY:         linear (ii) MOLECULE TYPE:        Protein (xi) SEQUENCE DESCRIPTION: SEQ ID NO: 44:

Trp Met Pro Pro Glu
1               5

(2) INFORMATION FOR SEQ ID NO: 45:

(i) SEQUENCE CHARACTERISTICS:
          (A) LENGTH:           8 amino acids
          (B) TYPE:             amino acid
          (C) STRANDEDNESS:     single
          (D) TOPOLOGY:         linear (ii) MOLECULE TYPE:        Protein (xi) SEQUENCE DESCRIPTION: SEQ ID NO: 45:

Gly Glu Gly Asn Phe Gly Gln Val
1               5

(2) INFORMATION FOR SEQ ID NO: 46:

(i) SEQUENCE CHARACTERISTICS:
          (A) LENGTH:           8 amino acids
          (B) TYPE:             amino acid
          (C) STRANDEDNESS:     single
          (D) TOPOLOGY:         linear (ii) MOLECULE TYPE:             Protein
```

(xi) SEQUENCE DESCRIPTION: SEQ ID NO: 46:

Ala Phe Gly Glu Val Tyr Glu Gly
1               5

(2) INFORMATION FOR SEQ ID NO: 47:

(i) SEQUENCE CHARACTERISTICS:
            (A) LENGTH:         5 amino acids
            (B) TYPE:           amino acid
            (C) STRANDEDNESS:   single
            (D) TOPOLOGY:       linear (ii) MOLECULE TYPE:     Protein (ix) FEATURE:
            (D) OTHER INFORMATION:  "Xaa" stands for Leu, Ile or Val.

(xi) SEQUENCE DESCRIPTION: SEQ ID NO: 47:

His Arg Asp Xaa Ala
1               5

(2) INFORMATION FOR SEQ ID NO: 48:

(i) SEQUENCE CHARACTERISTICS:
            (A) LENGTH:         8 amino acids
            (B) TYPE:           amino acid
            (C) STRANDEDNESS:   single
            (D) TOPOLOGY:       linear (ii) MOLECULE TYPE:     Protein (xi) SEQUENCE DESCRIPTION: SEQ ID NO: 48:

Gly His Gly Trp Phe Gly Lys Val
1               5

(2) INFORMATION FOR SEQ ID NO: 49:

(i) SEQUENCE CHARACTERISTICS:
            (A) LENGTH:         5 amino acids
            (B) TYPE:           amino acid
            (C) STRANDEDNESS:   single
            (D) TOPOLOGY:       linear (ii) MOLECULE TYPE:     Protein (xi) SEQUENCE DESCRIPTION: SEQ ID NO: 49:

Trp Tyr Ala Pro Glu
1               5

(2) INFORMATION FOR SEQ ID NO: 50:

(i) SEQUENCE CHARACTERISTICS:
            (A) LENGTH:         5 amino acids
            (B) TYPE:           amino acid
            (C) STRANDEDNESS:   single
            (D) TOPOLOGY:       linear (ii) MOLECULE TYPE:     Protein (xi) SEQUENCE DESCRIPTION: SEQ ID NO: 50:

Trp Thr Ala Pro Glu
1               5

(2) INFORMATION FOR SEQ ID NO: 51:

(i) SEQUENCE CHARACTERISTICS:
            (A) LENGTH:         8 amino acids
            (B) TYPE:           amino acid
            (C) STRANDEDNESS:   single

```
                (D)  TOPOLOGY:            linear (ii) MOLECULE TYPE:               Protein (ix) FEATURE:
                (D)  OTHER INFORMATION:   "Xaa" in position 4 stands
                     for Met or Val.
                     "Xaa" in position 6 stands
                     for Tyr or His.

(xi) SEQUENCE DESCRIPTION: SEQ ID NO: 51:

Ala Cys Gly Xaa Leu Xaa Leu His
1               5

(2) INFORMATION FOR SEQ ID NO: 52:

(i) SEQUENCE CHARACTERISTICS:
                (A)  LENGTH:              9 amino acids
                (B)  TYPE:                amino acid
                (C)  STRANDEDNESS:        single
                (D)  TOPOLOGY:            linear (ii) MOLECULE TYPE:               Protein (ix) FEATURE:
                (D)  OTHER INFORMATION:   "Xaa" stands for any amino acid.

(xi) SEQUENCE DESCRIPTION: SEQ ID NO: 52:

Asn Val Trp Xaa Xaa Gly Val Thr Ile
1               5

(2) INFORMATION FOR SEQ ID NO: 53:

(i) SEQUENCE CHARACTERISTICS:
                (A)  LENGTH:              8 amino acids
                (B)  TYPE:                amino acid
                (C)  STRANDEDNESS:        single
                (D)  TOPOLOGY:            linear (ii) MOLECULE TYPE:               Protein (ix) FEATURE:
                (D)  OTHER INFORMATION:   "Xaa" stands for any amino acid.

(xi) SEQUENCE DESCRIPTION: SEQ ID NO: 53:

Glu Phe Cys Pro Xaa Gly Asp Leu
1               5
```